US009528997B2

(12) United States Patent
Rogé et al.

(10) Patent No.: US 9,528,997 B2
(45) Date of Patent: Dec. 27, 2016

(54) **METHOD FOR DIAGNOSING *PROPIONIBACTERIUM* BACTERIAL INFECTIONS**

(71) Applicant: DIAXONHIT, Paris (FR)

(72) Inventors: Julie Rogé, Montrouge (FR); Hélène Nuyttens, Ivry sur Seine (FR); Karine Mignon Godefroy, Paris (FR); Damien Thomas, Chilly Mazarin (FR); Virginie Pinchot, Evry (FR)

(73) Assignee: Diaxonhit, Paris (FR)

( * ) Notice: Subject to any disclaimer, the term of this patent is extended or adjusted under 35 U.S.C. 154(b) by 0 days.

(21) Appl. No.: 13/676,597

(22) Filed: Nov. 14, 2012

(65) Prior Publication Data

US 2013/0123132 A1 May 16, 2013

Related U.S. Application Data

(60) Provisional application No. 61/559,959, filed on Nov. 15, 2011.

(30) Foreign Application Priority Data

Nov. 15, 2011 (EP) .................................... 11306495

(51) Int. Cl.
*G01N 33/68* (2006.01)
*C07K 14/195* (2006.01)
*G01N 33/569* (2006.01)

(52) U.S. Cl.
CPC ......... *G01N 33/6854* (2013.01); *C07K 14/195* (2013.01); *G01N 33/56911* (2013.01)

(58) Field of Classification Search
None
See application file for complete search history.

(56) References Cited

FOREIGN PATENT DOCUMENTS

WO WO 03033515 A1 * 4/2003
WO 2010128232 A2 11/2010

OTHER PUBLICATIONS

Greenspan et al. Nature Biotechnology 17: 936-937, 1999.*
Skolnick et al. Trends in Biotechnology 18: 34-39, 2000.*
McGuinness et al. Mol. Microbiol. 7: 505-514, 1993.*
McGuinness et al. Lancet 337: 514-517, 1991.*
Nusbaum et al. Skin Therapy Lett. 2005-2012.*
Berthelot et al., "Outbreak of Postoperative Shoulder Arthritis Due to Propionibacterium Acnes Infection in Nondebilitated Patients", Infection Control and Hospital Epidemiology, Sep. 2006, pp. 987-990, vol. 27 No. 9.
Bock et al., "Selection of Single-Stranded DNA Molecules that Bind and Inhibit Human Thrombin", Nature, Feb. 6, 1992, pp. 564-566, vol. 355.
Brook et al., "Infections Caused by *Propionibacterium* Species", Reviews of Infectious Diseases, Sep.-Oct. 1991, pp. 819-822, vol. 13 No. 5.
Brook et al., "Anaerobic Osteomyelitis and Arthritis in a Military Hospital: A 10-Year Experience", The American Journal of Medicine, Jan. 1993, pp. 21-28, vol. 94.
Ellington et al., "In Vitro Selection of RNA Molecules that Bind Specific Ligands", Nature, Aug. 30, 1990, pp. 818-822, vol. 346.
Franta et al., "The Complex Characteristics of 282 Unsatisfactory Shoulder Arthroplasties", Journal of Shoulder and Elbow Surgery, Sep.-Oct. 2007, pp. 555-562, vol. 16 No. 5.
Gehse et al., "Propionibacteria in Patients with Acne Vulgaris and in Healthy Persons", Archives of Dermatological Research, 1983, pp. 100-104, vol. 275.
Hoppe-Seyler et al., "Peptide Aptamers: Powerful New Tools for Molecular Medicine", Journal of Molecular Medicine, 2000, pp. 466-470, vol. 78.
Jakab et al., "Severe Infections Caused by Propionibacterium Acnes: An Underestimated Pathogen in Late Postoperative Infections", Yale Journal of Biology and Medicine, 1996, pp. 477-482, vol. 69.
Lavallie, "Production of Recombinant Proteins in *Escherichia coli*", Current Protocols in Protein Science, 1995, pp. 5.1.1-5.1.8.
Lutz et al., "Arthroplastic and Osteosynthetic Infections Due to Propionibacterium Acnes: A Retrospective Study of 52 cases, 1995-2002", European Journal of Clinical Microbiology & Infectious Diseases, 2005, pp. 739-744, vol. 24.
Marks et al., "By-Passing Immunization Human Antibodies from V-Gene Libraries Displayed on Phage", Journal of Molecular Biology, 1991, pp. 581-597. vol. 222.
Needleman et al., "A General Method Applicable to the Search for Similarities in the Amino Acid Sequence of Two Proteins", Journal of Molecular Biology, 1970, pp. 443-453, vol. 48.
Creighton, "Chapter 2.4 Posttranslational Covalent Modifications of Polypeptide Chains"; Proteins Structure and Molecular Properties—2nd Edition, 1993, pp. 78-100, W.H. Freeman and Company, New York.
Scopes, "Strategies for Protein Purification", Current Protocols in Protein Science, 1995, pp. 1.2.1-1.2.4.
Scott et al., "Searching for Peptide Ligands with an Epitope Library", Science, Jul. 27, 1990, pp. 386-390, vol. 249.
Seifter et al., "Analysis for Protein Modifications and Nonprotein Cofactors", Methods in Enzymology, 1990, pp. 626-646, vol. 182.
Sperling et al., "Infection After Shoulder Arthroplasty", Clinical Orthopaedics and Related Research, Jan. 2001, pp. 206-216, No. 382.
Wild, "The Immunoassay Handbook", 2005, pp. 31-40, Elsevier Ltd.
Winter et al., "Making Antibodies by Phage Display Technology", Annual Review of Immunology, 1994, pp. 433-455, vol. 12.

(Continued)

*Primary Examiner* — S. Devi
(74) *Attorney, Agent, or Firm* — Thompson Coburn LLP

(57) ABSTRACT

The invention concerns an in vitro method for determining if an individual is infected by a bacterium of the *Propionibacterium* genus comprising: (i) detecting antibodies directed against at least one protein of sequence SEQ ID NO: 2, SEQ ID NO: 4, SEQ ID NO: 6 or SEQ ID NO: 8, in a biological sample of the individual, and (ii) deducing therefrom that the individual is infected by a bacterium of the *Propionibacterium* genus. The invention further concerns the kit for diagnosing of such an infection.

8 Claims, No Drawings

(56) References Cited

OTHER PUBLICATIONS

Rattan et al., "Protein Synthesis, Posttranslational Modifications, and Aging", Annals of the New York Academy of Sciences, Nov. 21, 1992, pp. 48-62, vol. 663.

Van Oss, "Chapter 23—Nature of Specific Ligand—Receptor Bonds, in Particular the Antigen—Antibody Bond", Immunochemistry, 1994, pp. 581-614, edited by van Oss and van Regenmortel, Marcel Dekker, Inc., New York, NY, USA.

Wold, "Posttranslational Protein Modifications: Perspectives and Prospectives", Posttranslational Covalent Modifications of Proteins, 1983, pp. 1-17, edited by Johnson, Academic Press, Inc., New York, NY, USA.

Wild (ed.), "The Immunoassay Handbook (3rd Edition)", 2005, pp. 31-40, Elsevier Ltd.

Baldi et al., "Detection of Antibodies to *Brucella* Cytoplasmic Proteins in the Cerebrospinal Fluid of Patients with Neurobrucellosis", Clinical and Diagnostic Laboratory Immunology, Sep. 1999, pp. 756-759, vol. 6 No. 5.

Genetet, "Les Immunoglobulines", Immunologie—3rd Edition, 1997, 3 pages, Technique & Documentation.

* cited by examiner

SEQUENCE LISTING

```
<160> NUMBER OF SEQ ID NOS: 56

<210> SEQ ID NO 1
<211> LENGTH: 984
<212> TYPE: DNA
<213> ORGANISM: Propionibacterium acnes

<400> SEQUENCE: 1

ggtgacgacg ccaagaggtc atccgaagtt accttgacca actgtggaaa caaggtgacg     60

tatcccaagg ttgcccagcg tctctatgtc aatgacggca acatcatcgc catggctctc    120

agcgcggggg ccgctaagca gatcgctgct gtaagttcac tgggtgatga caaaacgatt    180

cttgctgcca agtacggctc gcatgtcatc gacaacctgc atgaggccgt caaggggtat    240

ccgacgctgg aatcgatcat cgccaacaag cccgatgtcg ttgtcgcggg ctggaattat    300

gggttctccg aagagggcaa tctgaccccg gacaagctcc atgagcgggg cattggcagt    360

tatctgctca gcgaatcctg tcggcagaag ggcagtgaga aggcccgtgg tgtcatgcag    420

ccgtgggacg ccgttcgcac agatctgagt aacctggcta agctcaccgg caatgaaccg    480

accgggaaga aggcggtcaa ggacctcgac gaccggcttg acgctcttaa caaggctccg    540

aaggctgcga aaacccctgt ggttttgctg ttcgactcag ccaaggacac cgtcctcact    600

agcggaaata agggcggacc gcaggccatc atcaatgctg cgggtggaca gaatgcagcc    660

cacgatgtca acgatacgtg ggtaaggatc agctgggaga aagtggcgac actcaagccc    720

gacgccatcg ccttcgttga ttacgatgcc cagccctact ccgagaaggt aaagatcctg    780

caatccaacc cggcgaccaa aaatcttgct gcagtgcaga agaagcgctt cctgaacctt    840

ccctacgcca tgtggacctc tggccctctc aacattgatg ctgctgagca cctgcgggtc    900

agcttggaga agtgggggtt ggagcctaag tcgtcgatca agccgcaact caccattcct    960

gcatccgtgc cggggcacga gggc                                           984

<210> SEQ ID NO 2
<211> LENGTH: 328
<212> TYPE: PRT
<213> ORGANISM: Propionibacterium acnes

<400> SEQUENCE: 2

Gly Asp Asp Ala Lys Arg Ser Ser Glu Val Thr Leu Thr Asn Cys Gly
1               5                   10                  15

Asn Lys Val Thr Tyr Pro Lys Val Ala Gln Arg Leu Tyr Val Asn Asp
            20                  25                  30

Gly Asn Ile Ile Ala Met Ala Leu Ser Ala Gly Ala Ala Lys Gln Ile
        35                  40                  45

Ala Ala Val Ser Ser Leu Gly Asp Asp Lys Thr Ile Leu Ala Ala Lys
    50                  55                  60

Tyr Gly Ser His Val Ile Asp Asn Leu His Glu Ala Val Lys Gly Tyr
```

```
65                  70                  75                  80

Pro Thr Leu Glu Ser Ile Ile Ala Asn Lys Pro Asp Val Val Val Ala
                85                  90                  95

Gly Trp Asn Tyr Gly Phe Ser Glu Glu Gly Asn Leu Thr Pro Asp Lys
            100                 105                 110

Leu His Glu Arg Gly Ile Gly Ser Tyr Leu Leu Ser Glu Ser Cys Arg
        115                 120                 125

Gln Lys Gly Ser Glu Lys Ala Arg Gly Val Met Gln Pro Trp Asp Ala
    130                 135                 140

Val Arg Thr Asp Leu Ser Asn Leu Ala Lys Leu Thr Gly Asn Glu Pro
145                 150                 155                 160

Thr Gly Lys Lys Ala Val Lys Asp Leu Asp Asp Arg Leu Asp Ala Leu
                165                 170                 175

Asn Lys Ala Pro Lys Ala Ala Lys Thr Pro Val Val Leu Leu Phe Asp
            180                 185                 190

Ser Ala Lys Asp Thr Val Leu Thr Ser Gly Asn Lys Gly Gly Pro Gln
        195                 200                 205

Ala Ile Ile Asn Ala Ala Gly Gly Gln Asn Ala Ala His Asp Val Asn
    210                 215                 220

Asp Thr Trp Val Arg Ile Ser Trp Glu Lys Val Ala Thr Leu Lys Pro
225                 230                 235                 240

Asp Ala Ile Ala Phe Val Asp Tyr Asp Ala Gln Pro Tyr Ser Glu Lys
                245                 250                 255

Val Lys Ile Leu Gln Ser Asn Pro Ala Thr Lys Asn Leu Ala Ala Val
            260                 265                 270

Gln Lys Lys Arg Phe Leu Asn Leu Pro Tyr Ala Met Trp Thr Ser Gly
        275                 280                 285

Pro Leu Asn Ile Asp Ala Ala Glu His Leu Arg Val Ser Leu Glu Lys
    290                 295                 300

Trp Gly Leu Glu Pro Lys Ser Ser Ile Lys Pro Gln Leu Thr Ile Pro
305                 310                 315                 320

Ala Ser Val Pro Gly His Glu Gly
                325
```

<210> SEQ ID NO 3
<211> LENGTH: 1452
<212> TYPE: DNA
<213> ORGANISM: Propionibacterium acnes

<400> SEQUENCE: 3

```
ggggcaacga gaccaatcga caccttgact atcgactcct gttcgggcga tactgtacta     60

aatcgtatta gttcagcagg aaccggcgcc aatggtggcc cagaacctgc tcaggcctca    120

cctctcgaag gaagaagcaa gatcatggga aacctcacca tcggtcgacg tcaactgctt    180

ggcggcaccg ccgcactcgc gacagtgctc gctgcgagcg catgtggcat gagtggttca    240

ggcgacaaac cgtcgaggca ggcatctgtt aacccgtccg ccaagctcga aggcagcatc    300

cagttccaaa cctggtcgct caagaacgaa aagttcacgc cctacttcaa gaagctcgtt    360

aagtcctttg agaaggaaca tcccggaaca acgatcaagt gggttgacca gccaggcgag    420

ggctatgagg agaaagtcca gcagcaagcc accgctggac agctgccgga tgtcattaac    480

ataccgccga acttcgcgtg gcagctcctc aaagccaaca aggtcatgga cctcaagaag    540

gctgacgcgg cagccaccaa cacatatatc aagggcggca ttgacgccta cacctacgac    600

ggttacgacg gcgtctacgg gtacccgtgg tacctcggca ccgacctgaa ctggtggaac    660
```

```
accgaagcct tcgagaagta cggtctcgat cccaagaagc tgccgaccac acttgatgag    720

ctttatgccc aagcgattac gatggccgag aagtcccacg gcacaatgcc cctcatctcc    780

atcgcaccag ctctcggtga ccttgccgcc cagggcgtca aggtctacaa ggacggaaaa    840

ttcactttca acaccgacca ggccgtcgag atcatccaga agtacgtcga gctttacgcc    900

aagaaggcta tgccgccgga ggtgttgcag aacaattacc tcggtaactc gaagctgttc    960

ctccagggca aggttgcgtg gaccactggc tcggcctcct tccctgtcga cctcaagaag   1020

agcgcaccga aactcctccc ccacgtcgcc atgaccacac gcatcggcgt tcccccccctg   1080

tttgtgcagg gcatctgcgt ctccgcagac tcgaagaacc ctaatctggc cctagcattc   1140

gcccaatatg tcaccaataa cgccaaccag gttgacttcg tcaagcttgc ccagggcttc   1200

ctgccgggaa ctaaggacgc caacgagaac acagactcct ttacctccgt catctccgat   1260

ccgcagatga agaaggccgc cgaggcccctt gccggcgaga tgaagtccgc caagatcggt   1320

gagcctatgg cctataccga cgccatgaaa gcgtacgtcg gtcagcagat ctcttcggca   1380

atgcgaggcg atatctccgc taaggacgca ctcgacaggg ccgtcaagta ctgcaacgac   1440

cacgtcacca ag                                                      1452
```

```
<210> SEQ ID NO 4
<211> LENGTH: 484
<212> TYPE: PRT
<213> ORGANISM: Propionibacterium acnes

<400> SEQUENCE: 4

Gly Ala Thr Arg Pro Ile Asp Thr Leu Thr Ile Asp Ser Cys Ser Gly
1               5                   10                  15

Asp Thr Val Leu Asn Arg Ile Ser Ser Ala Gly Thr Gly Ala Asn Gly
            20                  25                  30

Gly Pro Glu Pro Ala Gln Ala Ser Pro Leu Glu Gly Arg Ser Lys Ile
        35                  40                  45

Met Gly Asn Leu Thr Ile Gly Arg Arg Gln Leu Leu Gly Gly Thr Ala
    50                  55                  60

Ala Leu Ala Thr Val Leu Ala Ala Ser Ala Cys Gly Met Ser Gly Ser
65                  70                  75                  80

Gly Asp Lys Pro Ser Arg Gln Ala Ser Val Asn Pro Ser Ala Lys Leu
                85                  90                  95

Glu Gly Ser Ile Gln Phe Gln Thr Trp Ser Leu Lys Asn Glu Lys Phe
            100                 105                 110

Thr Pro Tyr Phe Lys Lys Leu Val Lys Ser Phe Glu Lys Glu His Pro
        115                 120                 125

Gly Thr Thr Ile Lys Trp Val Asp Gln Pro Gly Glu Gly Tyr Glu Glu
    130                 135                 140

Lys Val Gln Gln Gln Ala Thr Ala Gly Gln Leu Pro Asp Val Ile Asn
145                 150                 155                 160

Ile Pro Pro Asn Phe Ala Trp Gln Leu Leu Lys Ala Asn Lys Val Met
                165                 170                 175

Asp Leu Lys Lys Ala Asp Ala Ala Ala Thr Asn Thr Tyr Ile Lys Gly
            180                 185                 190

Gly Ile Asp Ala Tyr Thr Tyr Asp Gly Tyr Asp Gly Val Tyr Gly Tyr
        195                 200                 205

Pro Trp Tyr Leu Gly Thr Asp Leu Asn Trp Trp Asn Thr Glu Ala Phe
    210                 215                 220
```

```
Glu Lys Tyr Gly Leu Asp Pro Lys Lys Leu Pro Thr Thr Leu Asp Glu
225                 230                 235                 240

Leu Tyr Ala Gln Ala Ile Thr Met Ala Glu Lys Ser His Gly Thr Met
                245                 250                 255

Pro Leu Ile Ser Ile Ala Pro Ala Leu Gly Asp Leu Ala Ala Gln Gly
            260                 265                 270

Val Lys Val Tyr Lys Asp Gly Lys Phe Thr Phe Asn Thr Asp Gln Ala
        275                 280                 285

Val Glu Ile Ile Gln Lys Tyr Val Glu Leu Tyr Ala Lys Lys Ala Met
    290                 295                 300

Pro Pro Glu Val Leu Gln Asn Asn Tyr Leu Gly Asn Ser Lys Leu Phe
305                 310                 315                 320

Leu Gln Gly Lys Val Ala Trp Thr Thr Gly Ser Ala Ser Phe Pro Val
                325                 330                 335

Asp Leu Lys Lys Ser Ala Pro Lys Leu Leu Pro His Val Ala Met Thr
            340                 345                 350

Thr Arg Ile Gly Val Pro Pro Leu Phe Val Gln Gly Ile Cys Val Ser
        355                 360                 365

Ala Asp Ser Lys Asn Pro Asn Leu Ala Leu Ala Phe Ala Gln Tyr Val
    370                 375                 380

Thr Asn Asn Ala Asn Gln Val Asp Phe Val Lys Leu Ala Gln Gly Phe
385                 390                 395                 400

Leu Pro Gly Thr Lys Asp Ala Asn Glu Asn Thr Asp Ser Phe Thr Ser
                405                 410                 415

Val Ile Ser Asp Pro Gln Met Lys Lys Ala Ala Glu Ala Leu Ala Gly
            420                 425                 430

Glu Met Lys Ser Ala Lys Ile Gly Glu Pro Met Ala Tyr Thr Asp Ala
        435                 440                 445

Met Lys Ala Tyr Val Gly Gln Gln Ile Ser Ser Ala Met Arg Gly Asp
    450                 455                 460

Ile Ser Ala Lys Asp Ala Leu Asp Arg Ala Val Lys Tyr Cys Asn Asp
465                 470                 475                 480

His Val Thr Lys


<210> SEQ ID NO 5
<211> LENGTH: 903
<212> TYPE: DNA
<213> ORGANISM: Propionibacterium acnes

<400> SEQUENCE: 5

acagccacta atgcgcgcgc tcagcagact gaacgcatgg gtactgcgcc cggattcatt      60

gcggccttgg accagtccgg cggttctacc ccgaaggccc tcaaggcata tggggtagaa     120

cctgaggttt atggagacga tcaggacaag atgttcgatc tcgtccacga gatgcggacc     180

aggatcatca ccagcccgtc ttttactagc gaccatattc tcgcggcgat cctgttcgag     240

atgacgatgg atcgcaagat cgagggaatc cccaccggtg attacctgtg ggagaagaag     300

ggcattgttc ccattctcaa gattgataag ggcctggctg acgaagaccg ccacgttcgt     360

ctcatgaagc cgattcccgg cctcgacgag ttgctgcatc gcgccgtcga ggacaagcac     420

atcttcggta ccaaagagcg ctctgttatc ctggatgatg acaaagctgg cattgaaaag     480

attgtcgacc agcagttcga actggccgaa caggtgcgcg ctgcgggtct tgtgccgatc     540

ctcgaacccg aggtcgacat ccacgctcta cataaggaga aggctgagga aaggctgcac     600

aacctcatcc gcgcccacat cgactctctg ccgctcgatg ccaaaatcat gttgaagctg     660
```

```
acgatcccga gttccgaaga cctgtatgcc gacctcattg cggatccgaa ggtcctgcgc    720

gttgtcgccc tgtctggtgg gtactcccgt gaggaggcca acaagaagct ggcctgcaac    780

aggggactca tcgcgagctt ctctcgtgct ttggccgagg ggctaaacgt cgcacagtcg    840

cagcaggagt tcgatcagac tctgcgtgcc tctatcgact cgatttacgc cgcatcggtg    900

tcc                                                                  903


<210> SEQ ID NO 6
<211> LENGTH: 301
<212> TYPE: PRT
<213> ORGANISM: Propionibacterium acnes

<400> SEQUENCE: 6

Thr Ala Thr Asn Ala Arg Ala Gln Gln Thr Glu Arg Met Gly Thr Ala
1               5                   10                  15

Pro Gly Phe Ile Ala Ala Leu Asp Gln Ser Gly Gly Ser Thr Pro Lys
            20                  25                  30

Ala Leu Lys Ala Tyr Gly Val Glu Pro Glu Val Tyr Gly Asp Asp Gln
        35                  40                  45

Asp Lys Met Phe Asp Leu Val His Glu Met Arg Thr Arg Ile Ile Thr
    50                  55                  60

Ser Pro Ser Phe Thr Ser Asp His Ile Leu Ala Ala Ile Leu Phe Glu
65                  70                  75                  80

Met Thr Met Asp Arg Lys Ile Glu Gly Ile Pro Thr Gly Asp Tyr Leu
                85                  90                  95

Trp Glu Lys Lys Gly Ile Val Pro Ile Leu Lys Ile Asp Lys Gly Leu
            100                 105                 110

Ala Asp Glu Asp Arg His Val Arg Leu Met Lys Pro Ile Pro Gly Leu
        115                 120                 125

Asp Glu Leu Leu His Arg Ala Val Glu Asp Lys His Ile Phe Gly Thr
    130                 135                 140

Lys Glu Arg Ser Val Ile Leu Asp Asp Asp Lys Ala Gly Ile Glu Lys
145                 150                 155                 160

Ile Val Asp Gln Gln Phe Glu Leu Ala Glu Gln Val Arg Ala Ala Gly
                165                 170                 175

Leu Val Pro Ile Leu Glu Pro Glu Val Asp Ile His Ala Leu His Lys
            180                 185                 190

Glu Lys Ala Glu Glu Arg Leu His Asn Leu Ile Arg Ala His Ile Asp
        195                 200                 205

Ser Leu Pro Leu Asp Ala Lys Ile Met Leu Lys Leu Thr Ile Pro Ser
    210                 215                 220

Ser Glu Asp Leu Tyr Ala Asp Leu Ile Ala Asp Pro Lys Val Leu Arg
225                 230                 235                 240

Val Val Ala Leu Ser Gly Gly Tyr Ser Arg Glu Glu Ala Asn Lys Lys
                245                 250                 255

Leu Ala Cys Asn Arg Gly Leu Ile Ala Ser Phe Ser Arg Ala Leu Ala
            260                 265                 270

Glu Gly Leu Asn Val Ala Gln Ser Gln Gln Glu Phe Asp Gln Thr Leu
        275                 280                 285

Arg Ala Ser Ile Asp Ser Ile Tyr Ala Ala Ser Val Ser
    290                 295                 300


<210> SEQ ID NO 7
<211> LENGTH: 1194
```

```
<212> TYPE: DNA
<213> ORGANISM: Propionibacterium acnes

<400> SEQUENCE: 7

gcgcaccttg cccgcagggg gctgcatgtc accctgctgg agaaggtgac gttcccccgc      60

gacaaggttt gcggtgatgg cctgactccg cgcgccgtca agcagctcat ccggctgggt     120

atcgacgtct ccgaagaggc tggctggaaa cacacggagg ggctgcggat ccacggtgga     180

cgtatcgccc ccttcgttct tccctggccc gagttggccg actaccccaa tttcggcatg     240

gtgtgtcgac gcacggttct tgacgagcgt ttggctcgcc acgccgagtc gcagggagtc     300

gccctcgttg agggtgccaa tgtcactgat ccgatcctcg atctcagcgg ccgcattcgc     360

ggcgtccgga cctccgatgg caccgagtat tccgcccccg ttgtcgtcgc ggctgatggc     420

aactcttcgc gcctcggctt agcgatgggc ctgcataagc gtgacgaccg tccgatgggc     480

gtggcggtac gcgcctatta ccgctctgtg ctgtctgagt cgcgtaattt ggagagctgg     540

ctagaactgt gggacggtgc ccgcgcacaaa tctgaccttt tgccgggtta tggctgggcc    600

ttccctgagg gggatggaac ggtcaatatc ggtttgggaa tgcttgattc ctctgccgcg     660

tttggtcgca ctgattaccg ctcccttatg aaacgttggc tgtctcatct gcctgctgaa     720

tggaccctcg acgaagaaca ccgggagggg ccgatccgcg gtgccgccct gccgatggct     780

ttcaatcgtc aaccccatta tcgcgacggt ttgctactcg tgggggatgc cggtggcatg     840

gtcaacccat ttaatggcga gggcatcgac tacgccatgg aggccggtga gatggcggct     900

gatgctatcg ctgaggctca ttaccgtggt caccggactc cggctgctga gaaggcactc     960

cagggatatt cgcgcgctct gcaatgccac ttcggtggtt attaccggct ggggacgatc    1020

ttcgtgcggc tcatcggcga tccgcgtgtc atgaaggtgt gcacgacgta cgggctccct    1080

cgtcgtcgac tcatgaggtt tgtcaacaaa ttgttggcaa accttactga tgctaaagct    1140

ggagatcttg atgaccgtat tatcaacatt ctgacgagga ttgccccgtc ggtg          1194


<210> SEQ ID NO 8
<211> LENGTH: 398
<212> TYPE: PRT
<213> ORGANISM: Propionibacterium acnes

<400> SEQUENCE: 8

Ala His Leu Ala Arg Arg Gly Leu His Val Thr Leu Leu Glu Lys Val
1               5                   10                  15

Thr Phe Pro Arg Asp Lys Val Cys Gly Asp Gly Leu Thr Pro Arg Ala
            20                  25                  30

Val Lys Gln Leu Ile Arg Leu Gly Ile Asp Val Ser Glu Glu Ala Gly
        35                  40                  45

Trp Lys His Thr Glu Gly Leu Arg Ile His Gly Gly Arg Ile Ala Pro
    50                  55                  60

Phe Val Leu Pro Trp Pro Glu Leu Ala Asp Tyr Pro Asn Phe Gly Met
65                  70                  75                  80

Val Cys Arg Arg Thr Val Leu Asp Glu Arg Leu Ala Arg His Ala Glu
                85                  90                  95

Ser Gln Gly Val Ala Leu Val Glu Gly Ala Asn Val Thr Asp Pro Ile
            100                 105                 110

Leu Asp Leu Ser Gly Arg Ile Arg Gly Val Arg Thr Ser Asp Gly Thr
        115                 120                 125

Glu Tyr Ser Ala Pro Val Val Val Ala Ala Asp Gly Asn Ser Ser Arg
    130                 135                 140
```

```
Leu Gly Leu Ala Met Gly Leu His Lys Arg Asp Asp Arg Pro Met Gly
145                 150                 155                 160

Val Ala Val Arg Ala Tyr Tyr Arg Ser Val Leu Ser Glu Ser Arg Asn
                165                 170                 175

Leu Glu Ser Trp Leu Glu Leu Trp Asp Gly Ala Pro His Lys Ser Asp
            180                 185                 190

Leu Leu Pro Gly Tyr Gly Trp Ala Phe Pro Glu Gly Asp Gly Thr Val
        195                 200                 205

Asn Ile Gly Leu Gly Met Leu Asp Ser Ser Ala Ala Phe Gly Arg Thr
    210                 215                 220

Asp Tyr Arg Ser Leu Met Lys Arg Trp Leu Ser His Leu Pro Ala Glu
225                 230                 235                 240

Trp Thr Leu Asp Glu Glu His Arg Glu Gly Pro Ile Arg Gly Ala Ala
                245                 250                 255

Leu Pro Met Ala Phe Asn Arg Gln Pro His Tyr Arg Asp Gly Leu Leu
            260                 265                 270

Leu Val Gly Asp Ala Gly Gly Met Val Asn Pro Phe Asn Gly Glu Gly
        275                 280                 285

Ile Asp Tyr Ala Met Glu Ala Gly Glu Met Ala Ala Asp Ala Ile Ala
    290                 295                 300

Glu Ala His Tyr Arg Gly His Arg Thr Pro Ala Ala Glu Lys Ala Leu
305                 310                 315                 320

Gln Gly Tyr Ser Arg Ala Leu Gln Cys His Phe Gly Gly Tyr Tyr Arg
                325                 330                 335

Leu Gly Thr Ile Phe Val Arg Leu Ile Gly Asp Pro Arg Val Met Lys
            340                 345                 350

Val Cys Thr Thr Tyr Gly Leu Pro Arg Arg Arg Leu Met Arg Phe Val
        355                 360                 365

Asn Lys Leu Leu Ala Asn Leu Thr Asp Ala Lys Ala Gly Asp Leu Asp
    370                 375                 380

Asp Arg Ile Ile Asn Ile Leu Thr Arg Ile Ala Pro Ser Val
385                 390                 395
```

<210> SEQ ID NO 9
<211> LENGTH: 1407
<212> TYPE: DNA
<213> ORGANISM: Propionibacterium acnes

<400> SEQUENCE: 9

```
agcgatgtga agaaccccag ccagtccggc agttcctcca ctgctggcgt atcaaacgcc      60

accttggcga agattccagc cgctcaggcc ggggcaacgg acatcacctt caatgccgcc     120

cccgagaagg tcaaggccat cttcccgcgc ttcgcaaagg cgcggaacct cagcaccgca     180

gtagaggtcg tcaaagggcg catgctgcgc gattcctggc agcaaaacgc ttctgacgtc     240

aacgtcacct cccagatcat tgcctccaat gacgccgcat tgggcgtgct ggtgaccaac     300

cagaccacta tcgccggtaa gaagcagacg attccggcca ccatctggta ctcgaccgca     360

gcccagcagt catactcctc tcccgccctc gtcaagcccg acaaatgggc tgacctgacg     420

acagcgctgc aggatgctgg caaggatcag tccctcgacg gcggaaaaat tgccgcggcc     480

gtcaaggcga aatcggcccc gtatggcagc ggccccgccc tcggttttag ccacaacggt     540

gacctcttgg ccagctttgc ctcgggagtc gtcaccgata aggccgtcac cctcgtcgtt     600

cccagcgaca aaacgaaggg aatgctcagc aacttcggca cccaggctca gaaagcctca     660
```

```
acaaatcccg gcacgttcac tggaactacc tcccagcccg tagatgagtc cctcaaagcc     720

acggacacga gtggtcgccc accaacagcc gtcggcccgg actgtcgggt actgcactgc     780

gtcgcagtca cctatgacga tggccccagc gccatgaccc cagaacttct caacaccatc     840

aagaagttca agttgtcgat caccttcttc gagatgggca acagcatcat ggccttccca     900

aatacggccc agaaggtggc tgccgccggc atggagatcg gcaaccacac agtcacccac     960

ccgaatcttc cggcgaagac cccggatcgc atccgtcgtg aactggagca caactcgcag    1020

ctcattaagc agttcaccgg ggccactccg ctgttgttcc gcccacccta tggcgctcac    1080

aacgacactg ttgacaaggt cgccaaggac aatggcatgg caatcattca gtggcagatt    1140

gacagcgaag actggaagaa ccgcaaccct gagatgacgt ataagaacgt catgaccgcg    1200

ctgccgtaca ccgcacctat cgtccttgaa cacgacatcc agaaggcatc aatcgacgcc    1260

gccccgcaga tctataagga tcttgaagca aagggcaaga ccatcgtcag cgtcagtgaa    1320

ctgtccctca acaccggggg ttaccaggcc ggtcacgctt actgcaatgg aacggtcaag    1380

ccacaaagcg gctataactg caaagga                                        1407
```

```
<210> SEQ ID NO 10
<211> LENGTH: 469
<212> TYPE: PRT
<213> ORGANISM: Propionibacterium acnes

<400> SEQUENCE: 10

Ser Asp Val Lys Asn Pro Ser Gln Ser Gly Ser Ser Ser Thr Ala Gly
1               5                   10                  15

Val Ser Asn Ala Thr Leu Ala Lys Ile Pro Ala Ala Gln Ala Gly Ala
            20                  25                  30

Thr Asp Ile Thr Phe Asn Ala Ala Pro Glu Lys Val Lys Ala Ile Phe
        35                  40                  45

Pro Arg Phe Ala Lys Ala Arg Asn Leu Ser Thr Ala Val Glu Val Val
    50                  55                  60

Lys Gly Arg Met Leu Arg Asp Ser Trp Gln Gln Asn Ala Ser Asp Val
65                  70                  75                  80

Asn Val Thr Ser Gln Ile Ile Ala Ser Asn Asp Ala Ala Leu Gly Val
                85                  90                  95

Leu Val Thr Asn Gln Thr Thr Ile Ala Gly Lys Lys Gln Thr Ile Pro
            100                 105                 110

Ala Thr Ile Trp Tyr Ser Thr Ala Ala Gln Gln Ser Tyr Ser Ser Pro
        115                 120                 125

Ala Leu Val Lys Pro Asp Lys Trp Ala Asp Leu Thr Thr Ala Leu Gln
    130                 135                 140

Asp Ala Gly Lys Asp Gln Ser Leu Asp Gly Gly Lys Ile Ala Ala Ala
145                 150                 155                 160

Val Lys Ala Lys Ser Ala Pro Tyr Gly Ser Gly Pro Ala Leu Gly Phe
                165                 170                 175

Ser His Asn Gly Asp Leu Leu Ala Ser Phe Ala Ser Gly Val Val Thr
            180                 185                 190

Asp Lys Ala Val Thr Leu Val Val Pro Ser Asp Lys Thr Lys Gly Met
        195                 200                 205

Leu Ser Asn Phe Gly Thr Gln Ala Gln Lys Ala Ser Thr Asn Pro Gly
    210                 215                 220

Thr Phe Thr Gly Thr Thr Ser Gln Pro Val Asp Glu Ser Leu Lys Ala
225                 230                 235                 240
```

```
Thr Asp Thr Ser Gly Arg Pro Pro Thr Ala Val Gly Pro Asp Cys Arg
            245                 250                 255

Val Leu His Cys Val Ala Val Thr Tyr Asp Asp Gly Pro Ser Ala Met
        260                 265                 270

Thr Pro Glu Leu Leu Asn Thr Ile Lys Lys Phe Lys Leu Ser Ile Thr
    275                 280                 285

Phe Phe Glu Met Gly Asn Ser Ile Met Ala Phe Pro Asn Thr Ala Gln
    290                 295                 300

Lys Val Ala Ala Ala Gly Met Glu Ile Gly Asn His Thr Val Thr His
305                 310                 315                 320

Pro Asn Leu Pro Ala Lys Thr Pro Asp Arg Ile Arg Arg Glu Leu Glu
            325                 330                 335

His Asn Ser Gln Leu Ile Lys Gln Phe Thr Gly Ala Thr Pro Leu Leu
        340                 345                 350

Phe Arg Pro Pro Tyr Gly Ala His Asn Asp Thr Val Asp Lys Val Ala
    355                 360                 365

Lys Asp Asn Gly Met Ala Ile Ile Gln Trp Gln Ile Asp Ser Glu Asp
    370                 375                 380

Trp Lys Asn Arg Asn Pro Glu Met Thr Tyr Lys Asn Val Met Thr Ala
385                 390                 395                 400

Leu Pro Tyr Thr Ala Pro Ile Val Leu Glu His Asp Ile Gln Lys Ala
            405                 410                 415

Ser Ile Asp Ala Ala Pro Gln Ile Tyr Lys Asp Leu Glu Ala Lys Gly
        420                 425                 430

Lys Thr Ile Val Ser Val Ser Glu Leu Ser Leu Asn Thr Gly Gly Tyr
    435                 440                 445

Gln Ala Gly His Ala Tyr Cys Asn Gly Thr Val Lys Pro Gln Ser Gly
    450                 455                 460

Tyr Asn Cys Lys Gly
465
```

<210> SEQ ID NO 11
<211> LENGTH: 1212
<212> TYPE: DNA
<213> ORGANISM: Propionibacterium acnes

<400> SEQUENCE: 11

```
gtgaccacac cagcgctgga atccggtgaa aagccggagc tgacgcgcag cggtatgact      60

gatccgcccc gacttgaacc actggcgcca tgcgcactgg gaaggcgccg ggaacggaga     120

cgaagtcgag cccgaagacc acctgacgac gccctgttgt tgcccggccg cgcacgccga     180

tcacagaaag ctagtttcgc catgcctgcc accccgaaat tccttcgccg agctgtcgcg     240

gtctcgatgc tccccgtcat catgcttgcc ggatgtgctg gcgcccccaa ggactcgtca     300

gcttcttctt cagcgtcggc gtcccagtcc aacgctggac ctatcaccat caccaactgt     360

ggccagaagg ttaccctcga caagccggcg acccgggccg tgactcttaa tcaaggggcc     420

accgaggatg tgctggctat cggtggtgag tccaagctcg cggggaccgc gtatcttgac     480

agtgggattc cgaagaaatg gaagaaggct tacgactcgg tcaaggtgct cgccaaagag     540

tacccgtcta aggagacctt cctatctgcc aaacccgatc tggcggtgtc ctcgtattcg     600

agtgctttca ccgacaaggc ggtgggaaca cgtgaggaat tgaagaagca gggaatcgcc     660

acatatatca gccccttttgg atgccctaaa ggcaccccgt cagctgaggc cacgtgggag     720

aatgtgtgga aggagatgcg agaggttgga acccttatcg ggcagaaaga tgccgccgac     780
```

```
aaggtcatcg ctgaacagcg catgtccctc aaagaggtct ccggtaacaa acacggcaac    840

gggacctcga tagtgtggtt cgactcgggt gacaaggttc cgttcatcgg cgctggccat    900

ggcggcccac agctgctcat ggacgctgtt ggggccaaga atctgtttgc gaacctcgat    960

gggggctggg ctgacggttc gtgggagaag atcgttggtt ccaaccccga tgtcatcgtc   1020

gttgcagacg ccgactggtc gacagctaag gacaagatcg cctatctgaa gaaggacccc   1080

gttctcagcc agatgaaggc ggttaaagac aacaaattcg tcaccgtgcc attttcccag   1140

actacccctg gcgccgagct ggttgacgga gcaaagactc tcaacgacgg cctggccagg   1200

gttaccggga ag                                                       1212


<210> SEQ ID NO 12
<211> LENGTH: 404
<212> TYPE: PRT
<213> ORGANISM: Propionibacterium acnes

<400> SEQUENCE: 12

Val Thr Thr Pro Ala Leu Glu Ser Gly Glu Lys Pro Glu Leu Thr Arg
1               5                   10                  15

Ser Gly Met Thr Asp Pro Pro Arg Leu Glu Pro Leu Ala Pro Cys Ala
            20                  25                  30

Leu Gly Arg Arg Arg Glu Arg Arg Arg Ser Arg Ala Arg Arg Pro Pro
        35                  40                  45

Asp Asp Ala Leu Leu Leu Pro Gly Arg Ala Arg Arg Ser Gln Lys Ala
    50                  55                  60

Ser Phe Ala Met Pro Ala Thr Pro Lys Phe Leu Arg Arg Ala Val Ala
65                  70                  75                  80

Val Ser Met Leu Pro Val Ile Met Leu Ala Gly Cys Ala Gly Ala Pro
                85                  90                  95

Lys Asp Ser Ser Ala Ser Ser Ser Ala Ser Ala Ser Gln Ser Asn Ala
            100                 105                 110

Gly Pro Ile Thr Ile Thr Asn Cys Gly Gln Lys Val Thr Leu Asp Lys
        115                 120                 125

Pro Ala Thr Arg Ala Val Thr Leu Asn Gln Gly Ala Thr Glu Asp Val
    130                 135                 140

Leu Ala Ile Gly Gly Glu Ser Lys Leu Ala Gly Thr Ala Tyr Leu Asp
145                 150                 155                 160

Ser Gly Ile Pro Lys Lys Trp Lys Lys Ala Tyr Asp Ser Val Lys Val
                165                 170                 175

Leu Ala Lys Glu Tyr Pro Ser Lys Glu Thr Phe Leu Ser Ala Lys Pro
            180                 185                 190

Asp Leu Ala Val Ser Ser Tyr Ser Ser Ala Phe Thr Asp Lys Ala Val
        195                 200                 205

Gly Thr Arg Glu Glu Leu Lys Lys Gln Gly Ile Ala Thr Tyr Ile Ser
    210                 215                 220

Pro Phe Gly Cys Pro Lys Gly Thr Pro Ser Ala Glu Ala Thr Trp Glu
225                 230                 235                 240

Asn Val Trp Lys Glu Met Arg Glu Val Gly Thr Leu Ile Gly Gln Lys
                245                 250                 255

Asp Ala Ala Asp Lys Val Ile Ala Glu Gln Arg Met Ser Leu Lys Glu
            260                 265                 270

Val Ser Gly Asn Lys His Gly Asn Gly Thr Ser Ile Val Trp Phe Asp
        275                 280                 285

Ser Gly Asp Lys Val Pro Phe Ile Gly Ala Gly His Gly Gly Pro Gln
```

```
    290                 295                 300

Leu Leu Met Asp Ala Val Gly Ala Lys Asn Leu Phe Ala Asn Leu Asp
305                 310                 315                 320

Gly Gly Trp Ala Asp Gly Ser Trp Glu Lys Ile Val Gly Ser Asn Pro
                325                 330                 335

Asp Val Ile Val Val Ala Asp Ala Asp Trp Ser Thr Ala Lys Asp Lys
            340                 345                 350

Ile Ala Tyr Leu Lys Lys Asp Pro Val Leu Ser Gln Met Lys Ala Val
        355                 360                 365

Lys Asp Asn Lys Phe Val Thr Val Pro Phe Ser Gln Thr Thr Pro Gly
    370                 375                 380

Ala Glu Leu Val Asp Gly Ala Lys Thr Leu Asn Asp Gly Leu Ala Arg
385                 390                 395                 400

Val Thr Gly Lys


<210> SEQ ID NO 13
<211> LENGTH: 1494
<212> TYPE: DNA
<213> ORGANISM: Propionibacterium acnes

<400> SEQUENCE: 13

atgacctcct ccactgaggc ctccacctcg aacccggtcg acactgacca gcagaatgtc      60

gccaacaccg ccgatggatc cgtggcggtt gacgaccttg gtagcccgga ggcctttctg     120

gccgctgtgg acgccaccat caagtacttc aatgacggcg acatcgtctc tgggaccgtc     180

gtcaaggtgg accgcgacga ggtcctcctt gacatcggtt acaagaccga gggtgtcatc     240

ccgtccaaag agttgtcgat caagcacgac gtggacccct ttgaggtagt caacgtcggt     300

gatgagatcg aggccctcgt tcagcagaag gaggacaagg aaggtcgtct gatcctgtcc     360

aagaagcgtg cccagtatga gcgcgcctgg ggcacgattg agcagatcaa ggaagaagac     420

ggcgtcgtca ccggtaccgt catcgaggtc gtcaagggtg gacttattgt cgacatcggc     480

ctgcgtggct tccttcccgc ctcccttgtt gagatgcgcc gagtccgtga cctccagccc     540

tacgtgggtc aggagatcga ggccaagatc atcgagctcg acaagaaccg caacaacgtt     600

gtgctgtcgc gtcgtgcgtg gctcgagcag actcagtctg aggttcgtca gaacttcctg     660

catcagctgc agaagggtca gatccgcaag ggcgtcgtct cctcgatcgt caacttcggt     720

gcctttgttg acctgggcgg tgtggacggc ttagtccacg tctccgagct gtcctggaag     780

catatcgacc acccgagcga ggtcgtcgag gttggtcagc ctgtcactgt cgaggtgctg     840

gacgtcgaca tggatcgtga gcgcgtctcg ctgtctctca aggcgaccca ggaggatccg     900

tggcaggcgt tcgcccgtct gcaccagatt ggtcagattg ttcctggcaa ggtcaccaag     960

ctcgttccgt tcggcgcttt cgttcgcgtc gaggacggca ttgagggtct ggtccacgtg    1020

tccgagctgg ccgagcgcca cgtcgaaatc cctgagcagg tcgttagcgt caacgacgat    1080

gtcatggtca agatcatcga catcgacctc gaccgtcgcc gcatctcgct gtcccttaag    1140

caggccaacg agggtatcga cgtggagtct gacgagttcg atccgtcgct gtacgggatg    1200

gctgcctcct atgatgagga cggtaactac atctaccccg agggctttga tccggagacc    1260

aatgagtgga agccgggtta cgacgagcag cgcatcgctt gggagcagca gtacgccgag    1320

gctcaggctc gctgggaggc tcaccgcaag caggtcatcg aggccgagca ggccgatcag    1380

gaagccgctc ttaccgatgg tggcgcccag tcgtcctaca ccagtggccc ggctgagggt    1440

tcgctggcgt ccgacgaggc tctgcaggct cttcgtgaca agttgaccca taac          1494
```

<210> SEQ ID NO 14
<211> LENGTH: 498
<212> TYPE: PRT
<213> ORGANISM: Propionibacterium acnes

<400> SEQUENCE: 14

Met Thr Ser Ser Thr Glu Ala Ser Thr Ser Asn Pro Val Asp Thr Asp
1 5 10 15

Gln Gln Asn Val Ala Asn Thr Ala Asp Gly Ser Val Ala Val Asp Asp
20 25 30

Leu Gly Ser Pro Glu Ala Phe Leu Ala Ala Val Asp Ala Thr Ile Lys
35 40 45

Tyr Phe Asn Asp Gly Asp Ile Val Ser Gly Thr Val Val Lys Val Asp
50 55 60

Arg Asp Glu Val Leu Leu Asp Ile Gly Tyr Lys Thr Glu Gly Val Ile
65 70 75 80

Pro Ser Lys Glu Leu Ser Ile Lys His Asp Val Asp Pro Phe Glu Val
85 90 95

Val Asn Val Gly Asp Glu Ile Glu Ala Leu Val Gln Gln Lys Glu Asp
100 105 110

Lys Glu Gly Arg Leu Ile Leu Ser Lys Lys Arg Ala Gln Tyr Glu Arg
115 120 125

Ala Trp Gly Thr Ile Glu Gln Ile Lys Glu Glu Asp Gly Val Val Thr
130 135 140

Gly Thr Val Ile Glu Val Val Lys Gly Gly Leu Ile Val Asp Ile Gly
145 150 155 160

Leu Arg Gly Phe Leu Pro Ala Ser Leu Val Glu Met Arg Arg Val Arg
165 170 175

Asp Leu Gln Pro Tyr Val Gly Gln Glu Ile Glu Ala Lys Ile Ile Glu
180 185 190

Leu Asp Lys Asn Arg Asn Asn Val Val Leu Ser Arg Arg Ala Trp Leu
195 200 205

Glu Gln Thr Gln Ser Glu Val Arg Gln Asn Phe Leu His Gln Leu Gln
210 215 220

Lys Gly Gln Ile Arg Lys Gly Val Val Ser Ser Ile Val Asn Phe Gly
225 230 235 240

Ala Phe Val Asp Leu Gly Gly Val Asp Gly Leu Val His Val Ser Glu
245 250 255

Leu Ser Trp Lys His Ile Asp His Pro Ser Glu Val Val Glu Val Gly
260 265 270

Gln Pro Val Thr Val Glu Val Leu Asp Val Asp Met Asp Arg Glu Arg
275 280 285

Val Ser Leu Ser Leu Lys Ala Thr Gln Glu Asp Pro Trp Gln Ala Phe
290 295 300

Ala Arg Leu His Gln Ile Gly Gln Ile Val Pro Gly Lys Val Thr Lys
305 310 315 320

Leu Val Pro Phe Gly Ala Phe Val Arg Val Glu Asp Gly Ile Glu Gly
325 330 335

Leu Val His Val Ser Glu Leu Ala Glu Arg His Val Glu Ile Pro Glu
340 345 350

Gln Val Val Ser Val Asn Asp Asp Val Met Val Lys Ile Ile Asp Ile
355 360 365

Asp Leu Asp Arg Arg Arg Ile Ser Leu Ser Leu Lys Gln Ala Asn Glu

```
    370                 375                 380

Gly Ile Asp Val Glu Ser Asp Glu Phe Asp Pro Ser Leu Tyr Gly Met
385                 390                 395                 400

Ala Ala Ser Tyr Asp Glu Asp Gly Asn Tyr Ile Tyr Pro Glu Gly Phe
                405                 410                 415

Asp Pro Glu Thr Asn Glu Trp Lys Pro Gly Tyr Asp Glu Gln Arg Ile
            420                 425                 430

Ala Trp Glu Gln Gln Tyr Ala Glu Ala Gln Ala Arg Trp Glu Ala His
        435                 440                 445

Arg Lys Gln Val Ile Glu Ala Glu Gln Ala Asp Gln Glu Ala Ala Leu
    450                 455                 460

Thr Asp Gly Gly Ala Gln Ser Ser Tyr Thr Ser Gly Pro Ala Glu Gly
465                 470                 475                 480

Ser Leu Ala Ser Asp Glu Ala Leu Gln Ala Leu Arg Asp Lys Leu Thr
                485                 490                 495

His Asn
```

<210> SEQ ID NO 15
<211> LENGTH: 1086
<212> TYPE: DNA
<213> ORGANISM: Propionibacterium acnes

<400> SEQUENCE: 15

```
gctatcgata tcgacgctga gcgggtcgat atggtcaaca accggcatac caccatcgtt      60

gatcccctca tagcggagta cttggcccat cacaacctgg acctgcgcgc caccaccgac     120

ccgcaggaag cgtaccgggg agcagacttc gtcgtcatcg ccaccccgac caactatgac     180

cctggccaaa actacttcga cacctcaagc gtcgacgagg tccttgatct ggtccaggaa     240

ctcgcccctc acacgacgac cgtcattaaa tcaacaatcc cggtgggctt cgtcgagggc     300

gttcgcaagg agcgctccgg gcttgacgtc atcttctccc ccgagttcct gcgagaaggt     360

aaggctctgt tcgataacct tcacccctcg cggatcgtcg tcggggcgga ctcccccaaa     420

gcccacctct tcgccgacct catggctgcc ggggccgttg acaccaatgt cccggtgctc     480

ttcgtcggtg ccaccgaggc cgaggccatc aagctcttcg ccaacaccta cctggcgatg     540

cgggtgtcct tcttcaacga gctcgacacc tatgcctccc agcgcgggct gtctacccgt     600

caagtcattg acggggtctg cctcgatcct cgcattggca accactacaa caacccgtcc     660

ttcgggtacg gcggttactg cctgcctaaa gacacccgtc aactattagc caattaccag     720

gacgtgccac agaccctcat ccaggccatc gtcgactcca acaccgtgcg caaagacttt     780

atcgcctctg acatcattgc cagggacccg aaacgggtgg ggatcttccg tctggtcatg     840

aaggcaggtt cggacaactt ccgttcctcc tcgatccaag gcgtcatgaa gcgcatcaag     900

gcgaagggca tcgaggtggt cgtctacgag ccgacctttg acggcgacga gtttttccac     960

tcggaggtca ccaagaacct tgccttcttc aaagctaact gcgacgtcat cattgccaac    1020

cggatgtcac cggatttatc cgatgtcgct gacaaggtct acacccggga tctcttcggt    1080

ggggac                                                               1086
```

<210> SEQ ID NO 16
<211> LENGTH: 362
<212> TYPE: PRT
<213> ORGANISM: Propionibacterium acnes

<400> SEQUENCE: 16

```
Ala Ile Asp Ile Asp Ala Glu Arg Val Asp Met Val Asn Asn Arg His
1               5                   10                  15

Thr Thr Ile Val Asp Pro Leu Ile Ala Glu Tyr Leu Ala His His Asn
            20                  25                  30

Leu Asp Leu Arg Ala Thr Thr Asp Pro Gln Glu Ala Tyr Arg Gly Ala
        35                  40                  45

Asp Phe Val Val Ile Ala Thr Pro Thr Asn Tyr Asp Pro Gly Gln Asn
    50                  55                  60

Tyr Phe Asp Thr Ser Ser Val Asp Glu Val Leu Asp Leu Val Gln Glu
65                  70                  75                  80

Leu Ala Pro His Thr Thr Thr Val Ile Lys Ser Thr Ile Pro Val Gly
                85                  90                  95

Phe Val Glu Gly Val Arg Lys Glu Arg Ser Gly Leu Asp Val Ile Phe
            100                 105                 110

Ser Pro Glu Phe Leu Arg Glu Gly Lys Ala Leu Phe Asp Asn Leu His
        115                 120                 125

Pro Ser Arg Ile Val Val Gly Ala Asp Ser Pro Lys Ala His Leu Phe
    130                 135                 140

Ala Asp Leu Met Ala Ala Gly Ala Val Asp Thr Asn Val Pro Val Leu
145                 150                 155                 160

Phe Val Gly Ala Thr Glu Ala Glu Ala Ile Lys Leu Phe Ala Asn Thr
                165                 170                 175

Tyr Leu Ala Met Arg Val Ser Phe Phe Asn Glu Leu Asp Thr Tyr Ala
            180                 185                 190

Ser Gln Arg Gly Leu Ser Thr Arg Gln Val Ile Asp Gly Val Cys Leu
        195                 200                 205

Asp Pro Arg Ile Gly Asn His Tyr Asn Asn Pro Ser Phe Gly Tyr Gly
    210                 215                 220

Gly Tyr Cys Leu Pro Lys Asp Thr Arg Gln Leu Leu Ala Asn Tyr Gln
225                 230                 235                 240

Asp Val Pro Gln Thr Leu Ile Gln Ala Ile Val Asp Ser Asn Thr Val
                245                 250                 255

Arg Lys Asp Phe Ile Ala Ser Asp Ile Ile Ala Arg Asp Pro Lys Arg
            260                 265                 270

Val Gly Ile Phe Arg Leu Val Met Lys Ala Gly Ser Asp Asn Phe Arg
        275                 280                 285

Ser Ser Ser Ile Gln Gly Val Met Lys Arg Ile Lys Ala Lys Gly Ile
    290                 295                 300

Glu Val Val Val Tyr Glu Pro Thr Phe Asp Gly Asp Glu Phe Phe His
305                 310                 315                 320

Ser Glu Val Thr Lys Asn Leu Ala Phe Phe Lys Ala Asn Cys Asp Val
                325                 330                 335

Ile Ile Ala Asn Arg Met Ser Pro Asp Leu Ser Asp Val Ala Asp Lys
            340                 345                 350

Val Tyr Thr Arg Asp Leu Phe Gly Gly Asp
        355                 360

<210> SEQ ID NO 17
<211> LENGTH: 1002
<212> TYPE: DNA
<213> ORGANISM: Propionibacterium acnes

<400> SEQUENCE: 17

accgtcaagg ttggtatcaa cggttttggc cgcattggcc gtaacttctt ccgcgccctt     60
```

```
gctgagcagg gcgccgacct cgaggtggtc gctgtcaacg acctcaccga caccaagacg    120

ctggcccacc tcctgaagta cgactcgatc atgggtcgtt tctccggtga ggtcagctac    180

gacgatgact ccatcaccgt tgacggcaag accatcaagg ttctcgccga gcgcaacccc    240

gctgacctgc cctggaagga gctcggcgcc gaaatcgtcg tcgagtccac tggactcttc    300

actgatggcg agaaggccaa ggcccacttt gaggccggcg ccaagaaggt catcatctcc    360

gctcccggca agaacgtcga cggcaccttc gtcatgggcg tcaacgatgg cgactacgac    420

aacgcgaagc acaacatcat ctcgaacgct tcttgcacca ccaactgcct cgctccgctt    480

gccaaagtcc tcaatgacgc cttcggtatc gagcgcggca tcatgactac cgtccacgcc    540

tacaccggtg atcagcgtct gcaggatgct cctcacaagg atctgcgtcg tgcccgcgcc    600

gctgccctca acatgatccc caccaagacc ggtgccgctc aggctgtggc cctggtcctc    660

ccggagctca agggcaagtt cgacggcctt gccgtccgcg ttccgacccc gaccggctct    720

ctgactgacc tgaccttcca gacctctaag gagaccaccg ttgaggaggt tcaggccgcc    780

gttaagaagg ctgccgaggg tccgctcaag ggcatcctgg cctacaccga ggacccgatc    840

gtgtcgaagg acatcgaggg cgacccgcac tcctcgatct tcgatgctac cgagaccaag    900

gtcatcggaa accttgttaa ggtcctctcc tggtacgaca acgagtgggg ctactccaac    960

cgtctggttg acctcaccaa gctcgtcgcc agcaagcttg cc                      1002


<210> SEQ ID NO 18
<211> LENGTH: 334
<212> TYPE: PRT
<213> ORGANISM: Propionibacterium acnes

<400> SEQUENCE: 18

Thr Val Lys Val Gly Ile Asn Gly Phe Gly Arg Ile Gly Arg Asn Phe
1               5                   10                  15

Phe Arg Ala Leu Ala Glu Gln Gly Ala Asp Leu Glu Val Val Ala Val
            20                  25                  30

Asn Asp Leu Thr Asp Thr Lys Thr Leu Ala His Leu Leu Lys Tyr Asp
        35                  40                  45

Ser Ile Met Gly Arg Phe Ser Gly Glu Val Ser Tyr Asp Asp Asp Ser
    50                  55                  60

Ile Thr Val Asp Gly Lys Thr Ile Lys Val Leu Ala Glu Arg Asn Pro
65                  70                  75                  80

Ala Asp Leu Pro Trp Lys Glu Leu Gly Ala Glu Ile Val Val Glu Ser
                85                  90                  95

Thr Gly Leu Phe Thr Asp Gly Glu Lys Ala Lys Ala His Phe Glu Ala
            100                 105                 110

Gly Ala Lys Lys Val Ile Ile Ser Ala Pro Gly Lys Asn Val Asp Gly
        115                 120                 125

Thr Phe Val Met Gly Val Asn Asp Gly Asp Tyr Asp Asn Ala Lys His
    130                 135                 140

Asn Ile Ile Ser Asn Ala Ser Cys Thr Thr Asn Cys Leu Ala Pro Leu
145                 150                 155                 160

Ala Lys Val Leu Asn Asp Ala Phe Gly Ile Glu Arg Gly Ile Met Thr
                165                 170                 175

Thr Val His Ala Tyr Thr Gly Asp Gln Arg Leu Gln Asp Ala Pro His
            180                 185                 190

Lys Asp Leu Arg Arg Ala Arg Ala Ala Ala Leu Asn Met Ile Pro Thr
        195                 200                 205
```

```
Lys Thr Gly Ala Ala Gln Ala Val Ala Leu Val Leu Pro Glu Leu Lys
    210                 215                 220

Gly Lys Phe Asp Gly Leu Ala Val Arg Val Pro Thr Pro Thr Gly Ser
225                 230                 235                 240

Leu Thr Asp Leu Thr Phe Gln Thr Ser Lys Glu Thr Thr Val Glu Glu
                245                 250                 255

Val Gln Ala Ala Val Lys Lys Ala Ala Glu Gly Pro Leu Lys Gly Ile
            260                 265                 270

Leu Ala Tyr Thr Glu Asp Pro Ile Val Ser Lys Asp Ile Glu Gly Asp
        275                 280                 285

Pro His Ser Ser Ile Phe Asp Ala Thr Glu Thr Lys Val Ile Gly Asn
    290                 295                 300

Leu Val Lys Val Leu Ser Trp Tyr Asp Asn Glu Trp Gly Tyr Ser Asn
305                 310                 315                 320

Arg Leu Val Asp Leu Thr Lys Leu Val Ala Ser Lys Leu Ala
                325                 330
```

<210> SEQ ID NO 19
<211> LENGTH: 891
<212> TYPE: DNA
<213> ORGANISM: Propionibacterium acnes

<400> SEQUENCE: 19

```
ggaatcgcag gcactggacg tatcgctcgc acgattctta aagacttcgc acatgtcccg     60

ggagcacgca tctgcgctat cgcgtcaagg tcggcagccc gcgccgatgc ttttgccgat    120

ctggttactc agaacctgag ttgtccccgc ccagacactc atgattccta tgtcgacatg    180

atcaccaacc ccacagtgga cgtcgtttac gtggcaaccc cgcaccctca gcatcgaccg    240

atcgccctgg ctgccattga cgccgggaag gctgttctcg tcgagaaatc cttcgccgca    300

actgcccatg cggctgccga aatagctgag gctgctcggg ctaaaagggt ctttgccatg    360

gaggggatgt ggacccggtt tttgcctgtc gttaccgaga tgatcgacgc cgtcaacaat    420

ggcgcgatcg gcgagccgac gggtatccag ggagatttgt tcgccctgcg cgattatgac    480

cctgacgacc gtctcttctc cccagctcta ggtggtggag taacccttga cctcggcgtc    540

tatgccctcg atttcgccat tcgcctcttt ggagagccca ctgaggtcat cgcccgtggc    600

aaccacttcc ccaatggggt ggattccgac gcttcgatgc tgctgacttt cccaaagaac    660

aaattcgcca cgctggccat ctcgttcacc tccgacggtc cgggacgcat gactattcaa    720

ggcaccgacg gctggataga ggtcgagcct aggttccacc accccagccg tatcctcatc    780

caccgccgcg gagtcatccc ggagatccac aacacccccg cgctgggccg cggctacgct    840

cacgaactca tggaggtctg ccaatgtctg cgagcggacg caccgagagc c             891
```

<210> SEQ ID NO 20
<211> LENGTH: 297
<212> TYPE: PRT
<213> ORGANISM: Propionibacterium acnes

<400> SEQUENCE: 20

```
Gly Ile Ala Gly Thr Gly Arg Ile Ala Arg Thr Ile Leu Lys Asp Phe
1               5                   10                  15

Ala His Val Pro Gly Ala Arg Ile Cys Ala Ile Ala Ser Arg Ser Ala
            20                  25                  30

Ala Arg Ala Asp Ala Phe Ala Asp Leu Val Thr Gln Asn Leu Ser Cys
        35                  40                  45
```

```
Pro Arg Pro Asp Thr His Asp Ser Tyr Val Asp Met Ile Thr Asn Pro
    50                  55                  60

Thr Val Asp Val Val Tyr Val Ala Thr Pro His Pro Gln His Arg Pro
65                  70                  75                  80

Ile Ala Leu Ala Ala Ile Asp Ala Gly Lys Ala Val Leu Val Glu Lys
                85                  90                  95

Ser Phe Ala Ala Thr Ala His Ala Ala Ala Glu Ile Ala Glu Ala Ala
            100                 105                 110

Arg Ala Lys Arg Val Phe Ala Met Glu Gly Met Trp Thr Arg Phe Leu
        115                 120                 125

Pro Val Val Thr Glu Met Ile Asp Ala Val Asn Asn Gly Ala Ile Gly
    130                 135                 140

Glu Pro Thr Gly Ile Gln Gly Asp Leu Phe Ala Leu Arg Asp Tyr Asp
145                 150                 155                 160

Pro Asp Asp Arg Leu Phe Ser Pro Ala Leu Gly Gly Gly Val Thr Leu
                165                 170                 175

Asp Leu Gly Val Tyr Ala Leu Asp Phe Ala Ile Arg Leu Phe Gly Glu
            180                 185                 190

Pro Thr Glu Val Ile Ala Arg Gly Asn His Phe Pro Asn Gly Val Asp
        195                 200                 205

Ser Asp Ala Ser Met Leu Leu Thr Phe Pro Lys Asn Lys Phe Ala Thr
    210                 215                 220

Leu Ala Ile Ser Phe Thr Ser Asp Gly Pro Gly Arg Met Thr Ile Gln
225                 230                 235                 240

Gly Thr Asp Gly Trp Ile Glu Val Glu Pro Arg Phe His His Pro Ser
                245                 250                 255

Arg Ile Leu Ile His Arg Arg Gly Val Ile Pro Glu Ile His Asn Thr
            260                 265                 270

Pro Ala Leu Gly Arg Gly Tyr Ala His Glu Leu Met Glu Val Cys Gln
        275                 280                 285

Cys Leu Arg Ala Asp Ala Pro Arg Ala
    290                 295


<210> SEQ ID NO 21
<211> LENGTH: 381
<212> TYPE: PRT
<213> ORGANISM: Artificial Sequence
<220> FEATURE:
<223> OTHER INFORMATION: His-Tag / Propionibacterium acnes

<400> SEQUENCE: 21

Met Ser Tyr Tyr His His His His His His Leu Glu Ser Thr Ser Leu
1               5                   10                  15

Tyr Lys Lys Ala Gly Leu Gly Asp Asp Ala Lys Arg Ser Ser Glu Val
            20                  25                  30

Thr Leu Thr Asn Cys Gly Asn Lys Val Thr Tyr Pro Lys Val Ala Gln
        35                  40                  45

Arg Leu Tyr Val Asn Asp Gly Asn Ile Ile Ala Met Ala Leu Ser Ala
    50                  55                  60

Gly Ala Ala Lys Gln Ile Ala Ala Val Ser Ser Leu Gly Asp Asp Lys
65                  70                  75                  80

Thr Ile Leu Ala Ala Lys Tyr Gly Ser His Val Ile Asp Asn Leu His
                85                  90                  95

Glu Ala Val Lys Gly Tyr Pro Thr Leu Glu Ser Ile Ile Ala Asn Lys
            100                 105                 110
```

```
Pro Asp Val Val Val Ala Gly Trp Asn Tyr Gly Phe Ser Glu Glu Gly
        115                 120                 125

Asn Leu Thr Pro Asp Lys Leu His Glu Arg Gly Ile Gly Ser Tyr Leu
    130                 135                 140

Leu Ser Glu Ser Cys Arg Gln Lys Gly Ser Glu Lys Ala Arg Gly Val
145                 150                 155                 160

Met Gln Pro Trp Asp Ala Val Arg Thr Asp Leu Ser Asn Leu Ala Lys
                165                 170                 175

Leu Thr Gly Asn Glu Pro Thr Gly Lys Lys Ala Val Lys Asp Leu Asp
            180                 185                 190

Asp Arg Leu Asp Ala Leu Asn Lys Ala Pro Lys Ala Ala Lys Thr Pro
        195                 200                 205

Val Val Leu Leu Phe Asp Ser Ala Lys Asp Thr Val Leu Thr Ser Gly
    210                 215                 220

Asn Lys Gly Gly Pro Gln Ala Ile Ile Asn Ala Ala Gly Gly Gln Asn
225                 230                 235                 240

Ala Ala His Asp Val Asn Asp Thr Trp Val Arg Ile Ser Trp Glu Lys
                245                 250                 255

Val Ala Thr Leu Lys Pro Asp Ala Ile Ala Phe Val Asp Tyr Asp Ala
            260                 265                 270

Gln Pro Tyr Ser Glu Lys Val Lys Ile Leu Gln Ser Asn Pro Ala Thr
        275                 280                 285

Lys Asn Leu Ala Ala Val Gln Lys Lys Arg Phe Leu Asn Leu Pro Tyr
    290                 295                 300

Ala Met Trp Thr Ser Gly Pro Leu Asn Ile Asp Ala Ala Glu His Leu
305                 310                 315                 320

Arg Val Ser Leu Glu Lys Trp Gly Leu Glu Pro Lys Ser Ser Ile Lys
                325                 330                 335

Pro Gln Leu Thr Ile Pro Ala Ser Val Pro Gly His Glu Gly Tyr Pro
            340                 345                 350

Ala Phe Leu Tyr Lys Val Val Asp Ser Arg Leu Leu Thr Lys Pro Glu
        355                 360                 365

Arg Lys Leu Ser Trp Leu Leu Pro Pro Leu Ser Asn Asn
    370                 375                 380


<210> SEQ ID NO 22
<211> LENGTH: 537
<212> TYPE: PRT
<213> ORGANISM: Artificial Sequence
<220> FEATURE:
<223> OTHER INFORMATION: His-Tag/Propionibacterium acnes

<400> SEQUENCE: 22

Met Ser Tyr Tyr His His His His His His Leu Glu Ser Thr Ser Leu
1               5                   10                  15

Tyr Lys Lys Ala Gly Leu Gly Ala Thr Arg Pro Ile Asp Thr Leu Thr
            20                  25                  30

Ile Asp Ser Cys Ser Gly Asp Thr Val Leu Asn Arg Ile Ser Ser Ala
        35                  40                  45

Gly Thr Gly Ala Asn Gly Gly Pro Glu Pro Ala Gln Ala Ser Pro Leu
    50                  55                  60

Glu Gly Arg Ser Lys Ile Met Gly Asn Leu Thr Ile Gly Arg Arg Gln
65                  70                  75                  80

Leu Leu Gly Gly Thr Ala Ala Leu Ala Thr Val Leu Ala Ala Ser Ala
                85                  90                  95
```

-continued

```
Cys Gly Met Ser Gly Ser Gly Asp Lys Pro Ser Arg Gln Ala Ser Val
            100                 105                 110

Asn Pro Ser Ala Lys Leu Glu Gly Ser Ile Gln Phe Gln Thr Trp Ser
        115                 120                 125

Leu Lys Asn Glu Lys Phe Thr Pro Tyr Phe Lys Lys Leu Val Lys Ser
    130                 135                 140

Phe Glu Lys Glu His Pro Gly Thr Thr Ile Lys Trp Val Asp Gln Pro
145                 150                 155                 160

Gly Glu Gly Tyr Glu Glu Lys Val Gln Gln Gln Ala Thr Ala Gly Gln
                165                 170                 175

Leu Pro Asp Val Ile Asn Ile Pro Pro Asn Phe Ala Trp Gln Leu Leu
            180                 185                 190

Lys Ala Asn Lys Val Met Asp Leu Lys Lys Ala Asp Ala Ala Ala Thr
        195                 200                 205

Asn Thr Tyr Ile Lys Gly Gly Ile Asp Ala Tyr Thr Tyr Asp Gly Tyr
    210                 215                 220

Asp Gly Val Tyr Gly Tyr Pro Trp Tyr Leu Gly Thr Asp Leu Asn Trp
225                 230                 235                 240

Trp Asn Thr Glu Ala Phe Glu Lys Tyr Gly Leu Asp Pro Lys Lys Leu
                245                 250                 255

Pro Thr Thr Leu Asp Glu Leu Tyr Ala Gln Ala Ile Thr Met Ala Glu
            260                 265                 270

Lys Ser His Gly Thr Met Pro Leu Ile Ser Ile Ala Pro Ala Leu Gly
        275                 280                 285

Asp Leu Ala Ala Gln Gly Val Lys Val Tyr Lys Asp Gly Lys Phe Thr
    290                 295                 300

Phe Asn Thr Asp Gln Ala Val Glu Ile Ile Gln Lys Tyr Val Glu Leu
305                 310                 315                 320

Tyr Ala Lys Lys Ala Met Pro Pro Glu Val Leu Gln Asn Asn Tyr Leu
                325                 330                 335

Gly Asn Ser Lys Leu Phe Leu Gln Gly Lys Val Ala Trp Thr Thr Gly
            340                 345                 350

Ser Ala Ser Phe Pro Val Asp Leu Lys Lys Ser Ala Pro Lys Leu Leu
        355                 360                 365

Pro His Val Ala Met Thr Thr Arg Ile Gly Val Pro Pro Leu Phe Val
    370                 375                 380

Gln Gly Ile Cys Val Ser Ala Asp Ser Lys Asn Pro Asn Leu Ala Leu
385                 390                 395                 400

Ala Phe Ala Gln Tyr Val Thr Asn Asn Ala Asn Gln Val Asp Phe Val
                405                 410                 415

Lys Leu Ala Gln Gly Phe Leu Pro Gly Thr Lys Asp Ala Asn Glu Asn
            420                 425                 430

Thr Asp Ser Phe Thr Ser Val Ile Ser Asp Pro Gln Met Lys Lys Ala
        435                 440                 445

Ala Glu Ala Leu Ala Gly Glu Met Lys Ser Ala Lys Ile Gly Glu Pro
    450                 455                 460

Met Ala Tyr Thr Asp Ala Met Lys Ala Tyr Val Gly Gln Gln Ile Ser
465                 470                 475                 480

Ser Ala Met Arg Gly Asp Ile Ser Ala Lys Asp Ala Leu Asp Arg Ala
                485                 490                 495

Val Lys Tyr Cys Asn Asp His Val Thr Lys Tyr Pro Ala Phe Leu Tyr
            500                 505                 510

Lys Val Val Asp Ser Arg Leu Leu Thr Lys Pro Glu Arg Lys Leu Ser
```

```
        515                 520                 525

Trp Leu Leu Pro Pro Leu Ser Asn Asn
    530                 535


<210> SEQ ID NO 23
<211> LENGTH: 354
<212> TYPE: PRT
<213> ORGANISM: Artificial Sequence
<220> FEATURE:
<223> OTHER INFORMATION: His-Tag/Propionibacterium acnes

<400> SEQUENCE: 23

Met Ser Tyr Tyr His His His His His His Leu Glu Ser Thr Ser Leu
1               5                   10                  15

Tyr Lys Lys Ala Gly Leu Thr Ala Thr Asn Ala Arg Ala Gln Gln Thr
            20                  25                  30

Glu Arg Met Gly Thr Ala Pro Gly Phe Ile Ala Ala Leu Asp Gln Ser
        35                  40                  45

Gly Gly Ser Thr Pro Lys Ala Leu Lys Ala Tyr Gly Val Glu Pro Glu
    50                  55                  60

Val Tyr Gly Asp Asp Gln Asp Lys Met Phe Asp Leu Val His Glu Met
65                  70                  75                  80

Arg Thr Arg Ile Ile Thr Ser Pro Ser Phe Thr Ser Asp His Ile Leu
                85                  90                  95

Ala Ala Ile Leu Phe Glu Met Thr Met Asp Arg Lys Ile Glu Gly Ile
            100                 105                 110

Pro Thr Gly Asp Tyr Leu Trp Glu Lys Lys Gly Ile Val Pro Ile Leu
        115                 120                 125

Lys Ile Asp Lys Gly Leu Ala Asp Glu Asp Arg His Val Arg Leu Met
    130                 135                 140

Lys Pro Ile Pro Gly Leu Asp Glu Leu Leu His Arg Ala Val Glu Asp
145                 150                 155                 160

Lys His Ile Phe Gly Thr Lys Glu Arg Ser Val Ile Leu Asp Asp Asp
                165                 170                 175

Lys Ala Gly Ile Glu Lys Ile Val Asp Gln Gln Phe Glu Leu Ala Glu
            180                 185                 190

Gln Val Arg Ala Ala Gly Leu Val Pro Ile Leu Glu Pro Glu Val Asp
        195                 200                 205

Ile His Ala Leu His Lys Glu Lys Ala Glu Glu Arg Leu His Asn Leu
    210                 215                 220

Ile Arg Ala His Ile Asp Ser Leu Pro Leu Asp Ala Lys Ile Met Leu
225                 230                 235                 240

Lys Leu Thr Ile Pro Ser Ser Glu Asp Leu Tyr Ala Asp Leu Ile Ala
                245                 250                 255

Asp Pro Lys Val Leu Arg Val Val Ala Leu Ser Gly Gly Tyr Ser Arg
            260                 265                 270

Glu Glu Ala Asn Lys Lys Leu Ala Cys Asn Arg Gly Leu Ile Ala Ser
        275                 280                 285

Phe Ser Arg Ala Leu Ala Glu Gly Leu Asn Val Ala Gln Ser Gln Gln
    290                 295                 300

Glu Phe Asp Gln Thr Leu Arg Ala Ser Ile Asp Ser Ile Tyr Ala Ala
305                 310                 315                 320

Ser Val Ser Tyr Pro Ala Phe Leu Tyr Lys Val Val Asp Ser Arg Leu
                325                 330                 335

Leu Thr Lys Pro Glu Arg Lys Leu Ser Trp Leu Leu Pro Pro Leu Ser
```

```
            340                 345                 350

Asn Asn


<210> SEQ ID NO 24
<211> LENGTH: 451
<212> TYPE: PRT
<213> ORGANISM: Artificial Sequence
<220> FEATURE:
<223> OTHER INFORMATION: His-Tag/Propionibacterium acnes

<400> SEQUENCE: 24

Met Ser Tyr Tyr His His His His His His Leu Glu Ser Thr Ser Leu
1               5                   10                  15

Tyr Lys Lys Ala Gly Leu Ala His Leu Ala Arg Arg Gly Leu His Val
            20                  25                  30

Thr Leu Leu Glu Lys Val Thr Phe Pro Arg Asp Lys Val Cys Gly Asp
        35                  40                  45

Gly Leu Thr Pro Arg Ala Val Lys Gln Leu Ile Arg Leu Gly Ile Asp
    50                  55                  60

Val Ser Glu Glu Ala Gly Trp Lys His Thr Glu Gly Leu Arg Ile His
65                  70                  75                  80

Gly Gly Arg Ile Ala Pro Phe Val Leu Pro Trp Pro Glu Leu Ala Asp
                85                  90                  95

Tyr Pro Asn Phe Gly Met Val Cys Arg Arg Thr Val Leu Asp Glu Arg
            100                 105                 110

Leu Ala Arg His Ala Glu Ser Gln Gly Val Ala Leu Val Glu Gly Ala
        115                 120                 125

Asn Val Thr Asp Pro Ile Leu Asp Leu Ser Gly Arg Ile Arg Gly Val
    130                 135                 140

Arg Thr Ser Asp Gly Thr Glu Tyr Ser Ala Pro Val Val Val Ala Ala
145                 150                 155                 160

Asp Gly Asn Ser Ser Arg Leu Gly Leu Ala Met Gly Leu His Lys Arg
                165                 170                 175

Asp Asp Arg Pro Met Gly Val Ala Val Arg Ala Tyr Tyr Arg Ser Val
            180                 185                 190

Leu Ser Glu Ser Arg Asn Leu Glu Ser Trp Leu Glu Leu Trp Asp Gly
        195                 200                 205

Ala Pro His Lys Ser Asp Leu Leu Pro Gly Tyr Gly Trp Ala Phe Pro
    210                 215                 220

Glu Gly Asp Gly Thr Val Asn Ile Gly Leu Gly Met Leu Asp Ser Ser
225                 230                 235                 240

Ala Ala Phe Gly Arg Thr Asp Tyr Arg Ser Leu Met Lys Arg Trp Leu
                245                 250                 255

Ser His Leu Pro Ala Glu Trp Thr Leu Asp Glu Glu His Arg Glu Gly
            260                 265                 270

Pro Ile Arg Gly Ala Ala Leu Pro Met Ala Phe Asn Arg Gln Pro His
        275                 280                 285

Tyr Arg Asp Gly Leu Leu Leu Val Gly Asp Ala Gly Gly Met Val Asn
    290                 295                 300

Pro Phe Asn Gly Glu Gly Ile Asp Tyr Ala Met Glu Ala Gly Glu Met
305                 310                 315                 320

Ala Ala Asp Ala Ile Ala Glu Ala His Tyr Arg Gly His Arg Thr Pro
                325                 330                 335

Ala Ala Glu Lys Ala Leu Gln Gly Tyr Ser Arg Ala Leu Gln Cys His
            340                 345                 350
```

```
Phe Gly Gly Tyr Tyr Arg Leu Gly Thr Ile Phe Val Arg Leu Ile Gly
        355                 360                 365

Asp Pro Arg Val Met Lys Val Cys Thr Thr Tyr Gly Leu Pro Arg Arg
    370                 375                 380

Arg Leu Met Arg Phe Val Asn Lys Leu Leu Ala Asn Leu Thr Asp Ala
385                 390                 395                 400

Lys Ala Gly Asp Leu Asp Asp Arg Ile Ile Asn Ile Leu Thr Arg Ile
                405                 410                 415

Ala Pro Ser Val Tyr Pro Ala Phe Leu Tyr Lys Val Val Asp Ser Arg
            420                 425                 430

Leu Leu Thr Lys Pro Glu Arg Lys Leu Ser Trp Leu Leu Pro Pro Leu
        435                 440                 445

Ser Asn Asn
    450


<210> SEQ ID NO 25
<211> LENGTH: 522
<212> TYPE: PRT
<213> ORGANISM: Artificial Sequence
<220> FEATURE:
<223> OTHER INFORMATION: His-Tag/Propionibacterium acnes

<400> SEQUENCE: 25

Met Ser Tyr Tyr His His His His His His Leu Glu Ser Thr Ser Leu
1               5                   10                  15

Tyr Lys Lys Ala Gly Leu Ser Asp Val Lys Asn Pro Ser Gln Ser Gly
            20                  25                  30

Ser Ser Ser Thr Ala Gly Val Ser Asn Ala Thr Leu Ala Lys Ile Pro
        35                  40                  45

Ala Ala Gln Ala Gly Ala Thr Asp Ile Thr Phe Asn Ala Ala Pro Glu
    50                  55                  60

Lys Val Lys Ala Ile Phe Pro Arg Phe Ala Lys Ala Arg Asn Leu Ser
65                  70                  75                  80

Thr Ala Val Glu Val Val Lys Gly Arg Met Leu Arg Asp Ser Trp Gln
                85                  90                  95

Gln Asn Ala Ser Asp Val Asn Val Thr Ser Gln Ile Ile Ala Ser Asn
            100                 105                 110

Asp Ala Ala Leu Gly Val Leu Val Thr Asn Gln Thr Thr Ile Ala Gly
        115                 120                 125

Lys Lys Gln Thr Ile Pro Ala Thr Ile Trp Tyr Ser Thr Ala Ala Gln
    130                 135                 140

Gln Ser Tyr Ser Ser Pro Ala Leu Val Lys Pro Asp Lys Trp Ala Asp
145                 150                 155                 160

Leu Thr Thr Ala Leu Gln Asp Ala Gly Lys Asp Gln Ser Leu Asp Gly
                165                 170                 175

Gly Lys Ile Ala Ala Ala Val Lys Ala Lys Ser Ala Pro Tyr Gly Ser
            180                 185                 190

Gly Pro Ala Leu Gly Phe Ser His Asn Gly Asp Leu Leu Ala Ser Phe
        195                 200                 205

Ala Ser Gly Val Val Thr Asp Lys Ala Val Thr Leu Val Val Pro Ser
    210                 215                 220

Asp Lys Thr Lys Gly Met Leu Ser Asn Phe Gly Thr Gln Ala Gln Lys
225                 230                 235                 240

Ala Ser Thr Asn Pro Gly Thr Phe Thr Gly Thr Thr Ser Gln Pro Val
                245                 250                 255
```

```
Asp Glu Ser Leu Lys Ala Thr Asp Thr Ser Gly Arg Pro Pro Thr Ala
            260                 265                 270

Val Gly Pro Asp Cys Arg Val Leu His Cys Val Ala Val Thr Tyr Asp
        275                 280                 285

Asp Gly Pro Ser Ala Met Thr Pro Glu Leu Leu Asn Thr Ile Lys Lys
    290                 295                 300

Phe Lys Leu Ser Ile Thr Phe Phe Glu Met Gly Asn Ser Ile Met Ala
305                 310                 315                 320

Phe Pro Asn Thr Ala Gln Lys Val Ala Ala Ala Gly Met Glu Ile Gly
                325                 330                 335

Asn His Thr Val Thr His Pro Asn Leu Pro Ala Lys Thr Pro Asp Arg
            340                 345                 350

Ile Arg Arg Glu Leu Glu His Asn Ser Gln Leu Ile Lys Gln Phe Thr
        355                 360                 365

Gly Ala Thr Pro Leu Leu Phe Arg Pro Pro Tyr Gly Ala His Asn Asp
    370                 375                 380

Thr Val Asp Lys Val Ala Lys Asp Asn Gly Met Ala Ile Ile Gln Trp
385                 390                 395                 400

Gln Ile Asp Ser Glu Asp Trp Lys Asn Arg Asn Pro Glu Met Thr Tyr
                405                 410                 415

Lys Asn Val Met Thr Ala Leu Pro Tyr Thr Ala Pro Ile Val Leu Glu
            420                 425                 430

His Asp Ile Gln Lys Ala Ser Ile Asp Ala Ala Pro Gln Ile Tyr Lys
        435                 440                 445

Asp Leu Glu Ala Lys Gly Lys Thr Ile Val Ser Val Ser Glu Leu Ser
    450                 455                 460

Leu Asn Thr Gly Gly Tyr Gln Ala Gly His Ala Tyr Cys Asn Gly Thr
465                 470                 475                 480

Val Lys Pro Gln Ser Gly Tyr Asn Cys Lys Gly Tyr Pro Ala Phe Leu
                485                 490                 495

Tyr Lys Val Val Asp Ser Arg Leu Leu Thr Lys Pro Glu Arg Lys Leu
            500                 505                 510

Ser Trp Leu Leu Pro Pro Leu Ser Asn Asn
        515                 520


<210> SEQ ID NO 26
<211> LENGTH: 457
<212> TYPE: PRT
<213> ORGANISM: Artificial Sequence
<220> FEATURE:
<223> OTHER INFORMATION: His-Tag/Propionibacterium acnes

<400> SEQUENCE: 26

Met Ser Tyr Tyr His His His His His His Leu Glu Ser Thr Ser Leu
1               5                   10                  15

Tyr Lys Lys Ala Gly Leu Val Thr Thr Pro Ala Leu Glu Ser Gly Glu
            20                  25                  30

Lys Pro Glu Leu Thr Arg Ser Gly Met Thr Asp Pro Pro Arg Leu Glu
        35                  40                  45

Pro Leu Ala Pro Cys Ala Leu Gly Arg Arg Arg Glu Arg Arg Arg Ser
    50                  55                  60

Arg Ala Arg Arg Pro Pro Asp Asp Ala Leu Leu Leu Pro Gly Arg Ala
65                  70                  75                  80

Arg Arg Ser Gln Lys Ala Ser Phe Ala Met Pro Ala Thr Pro Lys Phe
                85                  90                  95
```

```
Leu Arg Arg Ala Val Ala Val Ser Met Leu Pro Val Ile Met Leu Ala
            100                 105                 110

Gly Cys Ala Gly Ala Pro Lys Asp Ser Ser Ala Ser Ser Ser Ala Ser
        115                 120                 125

Ala Ser Gln Ser Asn Ala Gly Pro Ile Thr Ile Thr Asn Cys Gly Gln
    130                 135                 140

Lys Val Thr Leu Asp Lys Pro Ala Thr Arg Ala Val Thr Leu Asn Gln
145                 150                 155                 160

Gly Ala Thr Glu Asp Val Leu Ala Ile Gly Gly Glu Ser Lys Leu Ala
                165                 170                 175

Gly Thr Ala Tyr Leu Asp Ser Gly Ile Pro Lys Lys Trp Lys Lys Ala
            180                 185                 190

Tyr Asp Ser Val Lys Val Leu Ala Lys Glu Tyr Pro Ser Lys Glu Thr
        195                 200                 205

Phe Leu Ser Ala Lys Pro Asp Leu Ala Val Ser Ser Tyr Ser Ser Ala
    210                 215                 220

Phe Thr Asp Lys Ala Val Gly Thr Arg Glu Glu Leu Lys Lys Gln Gly
225                 230                 235                 240

Ile Ala Thr Tyr Ile Ser Pro Phe Gly Cys Pro Lys Gly Thr Pro Ser
                245                 250                 255

Ala Glu Ala Thr Trp Glu Asn Val Trp Lys Glu Met Arg Glu Val Gly
            260                 265                 270

Thr Leu Ile Gly Gln Lys Asp Ala Ala Asp Lys Val Ile Ala Glu Gln
        275                 280                 285

Arg Met Ser Leu Lys Glu Val Ser Gly Asn Lys His Gly Asn Gly Thr
    290                 295                 300

Ser Ile Val Trp Phe Asp Ser Gly Asp Lys Val Pro Phe Ile Gly Ala
305                 310                 315                 320

Gly His Gly Gly Pro Gln Leu Leu Met Asp Ala Val Gly Ala Lys Asn
                325                 330                 335

Leu Phe Ala Asn Leu Asp Gly Gly Trp Ala Asp Gly Ser Trp Glu Lys
            340                 345                 350

Ile Val Gly Ser Asn Pro Asp Val Ile Val Val Ala Asp Ala Asp Trp
        355                 360                 365

Ser Thr Ala Lys Asp Lys Ile Ala Tyr Leu Lys Lys Asp Pro Val Leu
    370                 375                 380

Ser Gln Met Lys Ala Val Lys Asp Asn Lys Phe Val Thr Val Pro Phe
385                 390                 395                 400

Ser Gln Thr Thr Pro Gly Ala Glu Leu Val Asp Gly Ala Lys Thr Leu
                405                 410                 415

Asn Asp Gly Leu Ala Arg Val Thr Gly Lys Tyr Pro Ala Phe Leu Tyr
            420                 425                 430

Lys Val Val Asp Ser Arg Leu Leu Thr Lys Pro Glu Arg Lys Leu Ser
        435                 440                 445

Trp Leu Leu Pro Pro Leu Ser Asn Asn
    450                 455
```

<210> SEQ ID NO 27
<211> LENGTH: 551
<212> TYPE: PRT
<213> ORGANISM: Artificial Sequence
<220> FEATURE:
<223> OTHER INFORMATION: His-Tag/Propionibacterium acnes

<400> SEQUENCE: 27

```
Met Ser Tyr Tyr His His His His His His Leu Glu Ser Thr Ser Leu
1               5                   10                  15

Tyr Lys Lys Ala Gly Leu Met Thr Ser Ser Thr Glu Ala Ser Thr Ser
            20                  25                  30

Asn Pro Val Asp Thr Asp Gln Gln Asn Val Ala Asn Thr Ala Asp Gly
        35                  40                  45

Ser Val Ala Val Asp Asp Leu Gly Ser Pro Glu Ala Phe Leu Ala Ala
    50                  55                  60

Val Asp Ala Thr Ile Lys Tyr Phe Asn Asp Gly Asp Ile Val Ser Gly
65                  70                  75                  80

Thr Val Val Lys Val Asp Arg Asp Glu Val Leu Leu Asp Ile Gly Tyr
                85                  90                  95

Lys Thr Glu Gly Val Ile Pro Ser Lys Glu Leu Ser Ile Lys His Asp
            100                 105                 110

Val Asp Pro Phe Glu Val Val Asn Val Gly Asp Glu Ile Glu Ala Leu
        115                 120                 125

Val Gln Gln Lys Glu Asp Lys Glu Gly Arg Leu Ile Leu Ser Lys Lys
    130                 135                 140

Arg Ala Gln Tyr Glu Arg Ala Trp Gly Thr Ile Glu Gln Ile Lys Glu
145                 150                 155                 160

Glu Asp Gly Val Val Thr Gly Thr Val Ile Glu Val Val Lys Gly Gly
                165                 170                 175

Leu Ile Val Asp Ile Gly Leu Arg Gly Phe Leu Pro Ala Ser Leu Val
            180                 185                 190

Glu Met Arg Arg Val Arg Asp Leu Gln Pro Tyr Val Gly Gln Glu Ile
        195                 200                 205

Glu Ala Lys Ile Ile Glu Leu Asp Lys Asn Arg Asn Asn Val Val Leu
    210                 215                 220

Ser Arg Arg Ala Trp Leu Glu Gln Thr Gln Ser Glu Val Arg Gln Asn
225                 230                 235                 240

Phe Leu His Gln Leu Gln Lys Gly Gln Ile Arg Lys Gly Val Val Ser
                245                 250                 255

Ser Ile Val Asn Phe Gly Ala Phe Val Asp Leu Gly Gly Val Asp Gly
            260                 265                 270

Leu Val His Val Ser Glu Leu Ser Trp Lys His Ile Asp His Pro Ser
        275                 280                 285

Glu Val Val Glu Val Gly Gln Pro Val Thr Val Glu Val Leu Asp Val
    290                 295                 300

Asp Met Asp Arg Glu Arg Val Ser Leu Ser Leu Lys Ala Thr Gln Glu
305                 310                 315                 320

Asp Pro Trp Gln Ala Phe Ala Arg Leu His Gln Ile Gly Gln Ile Val
                325                 330                 335

Pro Gly Lys Val Thr Lys Leu Val Pro Phe Gly Ala Phe Val Arg Val
            340                 345                 350

Glu Asp Gly Ile Glu Gly Leu Val His Val Ser Glu Leu Ala Glu Arg
        355                 360                 365

His Val Glu Ile Pro Glu Gln Val Val Ser Val Asn Asp Asp Val Met
    370                 375                 380

Val Lys Ile Ile Asp Ile Asp Leu Asp Arg Arg Arg Ile Ser Leu Ser
385                 390                 395                 400

Leu Lys Gln Ala Asn Glu Gly Ile Asp Val Glu Ser Asp Glu Phe Asp
                405                 410                 415
```

```
Pro Ser Leu Tyr Gly Met Ala Ala Ser Tyr Asp Glu Asp Gly Asn Tyr
            420                 425                 430

Ile Tyr Pro Glu Gly Phe Asp Pro Glu Thr Asn Glu Trp Lys Pro Gly
        435                 440                 445

Tyr Asp Glu Gln Arg Ile Ala Trp Glu Gln Gln Tyr Ala Glu Ala Gln
    450                 455                 460

Ala Arg Trp Glu Ala His Arg Lys Gln Val Ile Glu Ala Glu Gln Ala
465                 470                 475                 480

Asp Gln Glu Ala Ala Leu Thr Asp Gly Gly Ala Gln Ser Ser Tyr Thr
            485                 490                 495

Ser Gly Pro Ala Glu Gly Ser Leu Ala Ser Asp Glu Ala Leu Gln Ala
            500                 505                 510

Leu Arg Asp Lys Leu Thr His Asn Tyr Pro Ala Phe Leu Tyr Lys Val
        515                 520                 525

Val Asp Ser Arg Leu Leu Thr Lys Pro Glu Arg Lys Leu Ser Trp Leu
    530                 535                 540

Leu Pro Pro Leu Ser Asn Asn
545                 550


<210> SEQ ID NO 28
<211> LENGTH: 415
<212> TYPE: PRT
<213> ORGANISM: Artificial Sequence
<220> FEATURE:
<223> OTHER INFORMATION: His-Tag/Propionibacterium acnes

<400> SEQUENCE: 28

Met Ser Tyr Tyr His His His His His His Leu Glu Ser Thr Ser Leu
1               5                   10                  15

Tyr Lys Lys Ala Gly Leu Ala Ile Asp Ile Asp Ala Glu Arg Val Asp
            20                  25                  30

Met Val Asn Asn Arg His Thr Thr Ile Val Asp Pro Leu Ile Ala Glu
        35                  40                  45

Tyr Leu Ala His His Asn Leu Asp Leu Arg Ala Thr Thr Asp Pro Gln
    50                  55                  60

Glu Ala Tyr Arg Gly Ala Asp Phe Val Val Ile Ala Thr Pro Thr Asn
65                  70                  75                  80

Tyr Asp Pro Gly Gln Asn Tyr Phe Asp Thr Ser Ser Val Asp Glu Val
                85                  90                  95

Leu Asp Leu Val Gln Glu Leu Ala Pro His Thr Thr Thr Val Ile Lys
            100                 105                 110

Ser Thr Ile Pro Val Gly Phe Val Glu Gly Val Arg Lys Glu Arg Ser
        115                 120                 125

Gly Leu Asp Val Ile Phe Ser Pro Glu Phe Leu Arg Glu Gly Lys Ala
    130                 135                 140

Leu Phe Asp Asn Leu His Pro Ser Arg Ile Val Val Gly Ala Asp Ser
145                 150                 155                 160

Pro Lys Ala His Leu Phe Ala Asp Leu Met Ala Ala Gly Ala Val Asp
                165                 170                 175

Thr Asn Val Pro Val Leu Phe Val Gly Ala Thr Glu Ala Glu Ala Ile
            180                 185                 190

Lys Leu Phe Ala Asn Thr Tyr Leu Ala Met Arg Val Ser Phe Phe Asn
        195                 200                 205

Glu Leu Asp Thr Tyr Ala Ser Gln Arg Gly Leu Ser Thr Arg Gln Val
    210                 215                 220
```

-continued

```
Ile Asp Gly Val Cys Leu Asp Pro Arg Ile Gly Asn His Tyr Asn Asn
225                 230                 235                 240

Pro Ser Phe Gly Tyr Gly Gly Tyr Cys Leu Pro Lys Asp Thr Arg Gln
                245                 250                 255

Leu Leu Ala Asn Tyr Gln Asp Val Pro Gln Thr Leu Ile Gln Ala Ile
            260                 265                 270

Val Asp Ser Asn Thr Val Arg Lys Asp Phe Ile Ala Ser Asp Ile Ile
        275                 280                 285

Ala Arg Asp Pro Lys Arg Val Gly Ile Phe Arg Leu Val Met Lys Ala
    290                 295                 300

Gly Ser Asp Asn Phe Arg Ser Ser Ser Ile Gln Gly Val Met Lys Arg
305                 310                 315                 320

Ile Lys Ala Lys Gly Ile Glu Val Val Val Tyr Glu Pro Thr Phe Asp
                325                 330                 335

Gly Asp Glu Phe Phe His Ser Glu Val Thr Lys Asn Leu Ala Phe Phe
            340                 345                 350

Lys Ala Asn Cys Asp Val Ile Ile Ala Asn Arg Met Ser Pro Asp Leu
        355                 360                 365

Ser Asp Val Ala Asp Lys Val Tyr Thr Arg Asp Leu Phe Gly Gly Asp
    370                 375                 380

Tyr Pro Ala Phe Leu Tyr Lys Val Val Asp Ser Arg Leu Leu Thr Lys
385                 390                 395                 400

Pro Glu Arg Lys Leu Ser Trp Leu Leu Pro Pro Leu Ser Asn Asn
                405                 410                 415


<210> SEQ ID NO 29
<211> LENGTH: 387
<212> TYPE: PRT
<213> ORGANISM: Artificial Sequence
<220> FEATURE:
<223> OTHER INFORMATION: His-Tag/Propionibacterium acnes

<400> SEQUENCE: 29

Met Ser Tyr Tyr His His His His His His Leu Glu Ser Thr Ser Leu
1               5                   10                  15

Tyr Lys Lys Ala Gly Leu Thr Val Lys Val Gly Ile Asn Gly Phe Gly
            20                  25                  30

Arg Ile Gly Arg Asn Phe Phe Arg Ala Leu Ala Glu Gln Gly Ala Asp
        35                  40                  45

Leu Glu Val Val Ala Val Asn Asp Leu Thr Asp Thr Lys Thr Leu Ala
    50                  55                  60

His Leu Leu Lys Tyr Asp Ser Ile Met Gly Arg Phe Ser Gly Glu Val
65                  70                  75                  80

Ser Tyr Asp Asp Asp Ser Ile Thr Val Asp Gly Lys Thr Ile Lys Val
                85                  90                  95

Leu Ala Glu Arg Asn Pro Ala Asp Leu Pro Trp Lys Glu Leu Gly Ala
            100                 105                 110

Glu Ile Val Val Glu Ser Thr Gly Leu Phe Thr Asp Gly Glu Lys Ala
        115                 120                 125

Lys Ala His Phe Glu Ala Gly Ala Lys Lys Val Ile Ile Ser Ala Pro
    130                 135                 140

Gly Lys Asn Val Asp Gly Thr Phe Val Met Gly Val Asn Asp Gly Asp
145                 150                 155                 160

Tyr Asp Asn Ala Lys His Asn Ile Ile Ser Asn Ala Ser Cys Thr Thr
                165                 170                 175
```

```
Asn Cys Leu Ala Pro Leu Ala Lys Val Leu Asn Asp Ala Phe Gly Ile
            180                 185                 190

Glu Arg Gly Ile Met Thr Thr Val His Ala Tyr Thr Gly Asp Gln Arg
        195                 200                 205

Leu Gln Asp Ala Pro His Lys Asp Leu Arg Arg Ala Arg Ala Ala Ala
    210                 215                 220

Leu Asn Met Ile Pro Thr Lys Thr Gly Ala Ala Gln Ala Val Ala Leu
225                 230                 235                 240

Val Leu Pro Glu Leu Lys Gly Lys Phe Asp Gly Leu Ala Val Arg Val
                245                 250                 255

Pro Thr Pro Thr Gly Ser Leu Thr Asp Leu Thr Phe Gln Thr Ser Lys
            260                 265                 270

Glu Thr Thr Val Glu Glu Val Gln Ala Ala Val Lys Lys Ala Ala Glu
        275                 280                 285

Gly Pro Leu Lys Gly Ile Leu Ala Tyr Thr Glu Asp Pro Ile Val Ser
    290                 295                 300

Lys Asp Ile Glu Gly Asp Pro His Ser Ser Ile Phe Asp Ala Thr Glu
305                 310                 315                 320

Thr Lys Val Ile Gly Asn Leu Val Lys Val Leu Ser Trp Tyr Asp Asn
                325                 330                 335

Glu Trp Gly Tyr Ser Asn Arg Leu Val Asp Leu Thr Lys Leu Val Ala
            340                 345                 350

Ser Lys Leu Ala Tyr Pro Ala Phe Leu Tyr Lys Val Val Asp Ser Arg
        355                 360                 365

Leu Leu Thr Lys Pro Glu Arg Lys Leu Ser Trp Leu Leu Pro Pro Leu
    370                 375                 380

Ser Asn Asn
385


<210> SEQ ID NO 30
<211> LENGTH: 350
<212> TYPE: PRT
<213> ORGANISM: Artificial Sequence
<220> FEATURE:
<223> OTHER INFORMATION: His-Tag/Propionibacterium acnes

<400> SEQUENCE: 30

Met Ser Tyr Tyr His His His His His His Leu Glu Ser Thr Ser Leu
1               5                   10                  15

Tyr Lys Lys Ala Gly Leu Gly Ile Ala Gly Thr Gly Arg Ile Ala Arg
            20                  25                  30

Thr Ile Leu Lys Asp Phe Ala His Val Pro Gly Ala Arg Ile Cys Ala
        35                  40                  45

Ile Ala Ser Arg Ser Ala Ala Arg Ala Asp Ala Phe Ala Asp Leu Val
    50                  55                  60

Thr Gln Asn Leu Ser Cys Pro Arg Pro Asp Thr His Asp Ser Tyr Val
65                  70                  75                  80

Asp Met Ile Thr Asn Pro Thr Val Asp Val Val Tyr Val Ala Thr Pro
                85                  90                  95

His Pro Gln His Arg Pro Ile Ala Leu Ala Ala Ile Asp Ala Gly Lys
            100                 105                 110

Ala Val Leu Val Glu Lys Ser Phe Ala Ala Thr Ala His Ala Ala Ala
        115                 120                 125

Glu Ile Ala Glu Ala Ala Arg Ala Lys Arg Val Phe Ala Met Glu Gly
    130                 135                 140
```

```
Met Trp Thr Arg Phe Leu Pro Val Val Thr Glu Met Ile Asp Ala Val
145                 150                 155                 160

Asn Asn Gly Ala Ile Gly Glu Pro Thr Gly Ile Gln Gly Asp Leu Phe
                165                 170                 175

Ala Leu Arg Asp Tyr Asp Pro Asp Asp Arg Leu Phe Ser Pro Ala Leu
            180                 185                 190

Gly Gly Gly Val Thr Leu Asp Leu Gly Val Tyr Ala Leu Asp Phe Ala
        195                 200                 205

Ile Arg Leu Phe Gly Glu Pro Thr Glu Val Ile Ala Arg Gly Asn His
    210                 215                 220

Phe Pro Asn Gly Val Asp Ser Asp Ala Ser Met Leu Leu Thr Phe Pro
225                 230                 235                 240

Lys Asn Lys Phe Ala Thr Leu Ala Ile Ser Phe Thr Ser Asp Gly Pro
                245                 250                 255

Gly Arg Met Thr Ile Gln Gly Thr Asp Gly Trp Ile Glu Val Glu Pro
            260                 265                 270

Arg Phe His His Pro Ser Arg Ile Leu Ile His Arg Arg Gly Val Ile
        275                 280                 285

Pro Glu Ile His Asn Thr Pro Ala Leu Gly Arg Gly Tyr Ala His Glu
    290                 295                 300

Leu Met Glu Val Cys Gln Cys Leu Arg Ala Asp Ala Pro Arg Ala Tyr
305                 310                 315                 320

Pro Ala Phe Leu Tyr Lys Val Val Asp Ser Arg Leu Leu Thr Lys Pro
                325                 330                 335

Glu Arg Lys Leu Ser Trp Leu Leu Pro Pro Leu Ser Asn Asn
            340                 345                 350
```

<210> SEQ ID NO 31
<211> LENGTH: 561
<212> TYPE: DNA
<213> ORGANISM: Staphylococcus epidermidis

<400> SEQUENCE: 31

```
ggaactaata ataagttaac tgtgtctgct aatcgtggtg ttgctcaaat taaaccaaca     60

aataatggct tatatacaac tgtttatgac agtaaaggtc ataagactga tcaagtacaa    120

aaaaccctat ccgttactaa aactgcaaca ttaggaaata acaaattcta tttagttgaa    180

gactacaata gcggtaaaaa atacggttgg gttaaacaag gtggtgttgt ttataacact    240

gctaaggcac cagtaaaagt gaatcaaaca tataatgtta aagcagggtc aacactttac    300

acagttcctt ggggtacacc aaaacaagtt gctagcaaag tatctggtac tggaaatcaa    360

acatttaaag caactaaaca gcaacaaatt gataaagcaa cgtatcttta tggtacagtg    420

aatggtaaat ctggttggat tagtaaatat tacttaacta cagcatctaa acctagcaat    480

ccaactaaac cttcaacaaa caaccaatta acagtgacta acaatagtgg tgttgctcaa    540

atcaatgcaa aaaatagtgg c                                              561
```

<210> SEQ ID NO 32
<211> LENGTH: 187
<212> TYPE: PRT
<213> ORGANISM: Staphylococcus epidermidis

<400> SEQUENCE: 32

```
Gly Thr Asn Asn Lys Leu Thr Val Ser Ala Asn Arg Gly Val Ala Gln
1               5                   10                  15

Ile Lys Pro Thr Asn Asn Gly Leu Tyr Thr Thr Val Tyr Asp Ser Lys
```

```
            20                  25                  30

Gly His Lys Thr Asp Gln Val Gln Lys Thr Leu Ser Val Thr Lys Thr
        35                  40                  45

Ala Thr Leu Gly Asn Asn Lys Phe Tyr Leu Val Glu Asp Tyr Asn Ser
    50                  55                  60

Gly Lys Lys Tyr Gly Trp Val Lys Gln Gly Gly Val Val Tyr Asn Thr
65                  70                  75                  80

Ala Lys Ala Pro Val Lys Val Asn Gln Thr Tyr Asn Val Lys Ala Gly
                85                  90                  95

Ser Thr Leu Tyr Thr Val Pro Trp Gly Thr Pro Lys Gln Val Ala Ser
            100                 105                 110

Lys Val Ser Gly Thr Gly Asn Gln Thr Phe Lys Ala Thr Lys Gln Gln
        115                 120                 125

Gln Ile Asp Lys Ala Thr Tyr Leu Tyr Gly Thr Val Asn Gly Lys Ser
    130                 135                 140

Gly Trp Ile Ser Lys Tyr Tyr Leu Thr Thr Ala Ser Lys Pro Ser Asn
145                 150                 155                 160

Pro Thr Lys Pro Ser Thr Asn Asn Gln Leu Thr Val Thr Asn Asn Ser
                165                 170                 175

Gly Val Ala Gln Ile Asn Ala Lys Asn Ser Gly
            180                 185


<210> SEQ ID NO 33
<211> LENGTH: 876
<212> TYPE: DNA
<213> ORGANISM: Staphylococcus epidermidis

<400> SEQUENCE: 33

tgtgggaatc acagtaacca tgaacatcac tcacatgaag gaaaattaaa agttgtaact     60

acaaactcta ttctctatga catggttaaa cgtgtcggtg gaaataaggt cgatgttcat    120

agcatcgttc cagtaggaca agacccacat gaatatgagg ttaaacctaa agatattaaa    180

gcattaacag atgctgacgt tgtattttat aacggtttaa acctagaaac tggaaatggt    240

tggtttgaaa aagcacttga ccaagcagga aaatcaacaa aagataaaaa tgtgatagca    300

gcatcaaata atgttaaacc aatatactta aatggtgagg aaggtaacaa aaacaaacaa    360

gatccacatg catggttaag tttagagaat ggaattaaat acgtaaaaac agtacaaaaa    420

tcactagaac atcatgataa aaaagataag tctacatatg aaaaacaagg gaatgcatat    480

atatcaaaat tagaagaact taataaagat agtaaaaata aatttgatga catacccaaa    540

aatcaacgtg ccatgatgac aagtgaaggt gcatttaaat attttgctca acaattcgat    600

gttaaaccag gttatatttg ggagataaac acagaaaaac aaggtacacc tggtcaaatg    660

aaacaagcca ttaaatttgt taaagataat catttaaaac atttattagt cgaaacaagc    720

gtagataaaa aagctatgca aagtttatca gaagaaacta agaaagatat ttatggtgaa    780

gtatttaccg actctatagg taaggaaggt actaaaggtg gctcatacta taaaatgatg    840

aaatctaata ttgatacaat acatggtagt atgaaa                              876


<210> SEQ ID NO 34
<211> LENGTH: 294
<212> TYPE: PRT
<213> ORGANISM: Staphylococcus epidermidis

<400> SEQUENCE: 34

Cys Gly Asn His Ser Asn His Glu His His Ser His Glu Gly Lys Leu
```

-continued

```
1               5                   10                  15

Lys Val Val Thr Thr Asn Ser Ile Leu Tyr Asp Met Glu Thr Val Lys
            20                  25                  30

Arg Val Gly Gly Asn Lys Val Asp Val His Ser Ile Val Pro Val Gly
        35                  40                  45

Gln Asp Pro His Glu Tyr Glu Val Lys Pro Lys Asp Ile Lys Ala Leu
    50                  55                  60

Thr Asp Ala Asp Val Val Phe Tyr Asn Gly Leu Asn Leu Glu Thr Gly
65                  70                  75                  80

Asn Gly Trp Phe Glu Lys Ala Leu Asp Gln Ala Gly Lys Ser Thr Lys
                85                  90                  95

Asp Lys Asn Val Ile Ala Ala Ser Asn Asn Val Lys Pro Ile Tyr Leu
            100                 105                 110

Asn Gly Glu Glu Gly Asn Lys Asn Lys Gln Asp Pro His Ala Trp Leu
        115                 120                 125

Ser Leu Glu Asn Gly Ile Lys Tyr Val Lys Thr Val Gln Lys Ser Leu
    130                 135                 140

Glu His His Asp Lys Lys Asp Lys Ser Thr Tyr Glu Lys Gln Gly Asn
145                 150                 155                 160

Ala Tyr Ile Ser Lys Leu Glu Glu Leu Asn Lys Asp Ser Lys Asn Lys
                165                 170                 175

Phe Asp Asp Ile Pro Lys Asn Gln Arg Ala Met Met Thr Ser Glu Gly
            180                 185                 190

Ala Phe Lys Tyr Phe Ala Gln Gln Phe Asp Val Lys Pro Gly Tyr Ile
        195                 200                 205

Trp Glu Ile Asn Thr Glu Lys Gln Gly Thr Pro Gly Gln Met Lys Gln
    210                 215                 220

Ala Ile Lys Phe Val Lys Asp Asn His Leu Lys His Leu Leu Val Glu
225                 230                 235                 240

Thr Ser Val Asp Lys Lys Ala Met Gln Ser Leu Ser Glu Glu Thr Lys
                245                 250                 255

Lys Asp Ile Tyr Gly Glu Val Phe Thr Asp Ser Ile Gly Lys Glu Gly
            260                 265                 270

Thr Lys Gly Gly Ser Tyr Tyr Lys Met Met Lys Ser Asn Ile Asp Thr
        275                 280                 285

Ile His Gly Ser Met Lys
    290
```

<210> SEQ ID NO 35
<211> LENGTH: 834
<212> TYPE: DNA
<213> ORGANISM: Staphylococcus aureus

<400> SEQUENCE: 35

```
ttaaaagtag taacgacgaa ttcaatttta tatgatatgg ctaaaaatgt tggtggagac     60

aacgtcgata ttcatagtat tgtacctgtt ggtcaagatc ctcatgaata tgaagttaaa    120

cctaaagata ttaaaaagtt aactgacgct gacgttattt tatacaacgg attaaattta    180

gagactggta acggttggtt tgaaaaagcc ttagaacagg ctggtaaatc attaaaagat    240

aaaaaagtta tcgcagtatc aaaagatgtt aaacctatct atttaaacgg tgaagaaggc    300

aacaaagata aacaagatcc acacgcatgg ttaagtttag ataatggtat taaatacgta    360

aaaacaattc aacaaacatt tatcgataac gacaaaaaac ataaagcaga ttatgaaaag    420

caaggtaaca aatacattgc tcaattggaa aaattaaata atgacagtaa agacaaattt    480
```

```
aatgacattc caaaagaaca acgtgccatg attacaagtg aaggtgcctt caagtacttc    540

tcaaaacaat acggtattac accaggttat atttgggaaa ttaacactga aaaacaaggt    600

acacctgaac aaatgagaca agctattgag tttgttaaaa agcacaaatt aaaacactta    660

ttagtagaaa caagtgttga taagaaagca atggaaagtt tatctgaaga aacgaagaaa    720

gatatctttg gtgaagtgta cacagattca atcggtaaag aaggcactaa aggtgactct    780

tactacaaaa tgatgaaatc aaatattgaa actgtacacg gaagcatgaa ataa          834
```

<210> SEQ ID NO 36
<211> LENGTH: 277
<212> TYPE: PRT
<213> ORGANISM: Staphylococcus aureus

<400> SEQUENCE: 36

```
Leu Lys Val Val Thr Thr Asn Ser Ile Leu Tyr Asp Met Ala Lys Asn
1               5                   10                  15

Val Gly Gly Asp Asn Val Asp Ile His Ser Ile Val Pro Val Gly Gln
            20                  25                  30

Asp Pro His Glu Tyr Glu Val Lys Pro Lys Asp Ile Lys Lys Leu Thr
        35                  40                  45

Asp Ala Asp Val Ile Leu Tyr Asn Gly Leu Asn Leu Glu Thr Gly Asn
    50                  55                  60

Gly Trp Phe Glu Lys Ala Leu Glu Gln Ala Gly Lys Ser Leu Lys Asp
65                  70                  75                  80

Lys Lys Val Ile Ala Val Ser Lys Asp Val Lys Pro Ile Tyr Leu Asn
                85                  90                  95

Gly Glu Glu Gly Asn Lys Asp Lys Gln Asp Pro His Ala Trp Leu Ser
            100                 105                 110

Leu Asp Asn Gly Ile Lys Tyr Val Lys Thr Ile Gln Gln Thr Phe Ile
        115                 120                 125

Asp Asn Asp Lys Lys His Lys Ala Asp Tyr Glu Lys Gln Gly Asn Lys
    130                 135                 140

Tyr Ile Ala Gln Leu Glu Lys Leu Asn Asn Asp Ser Lys Asp Lys Phe
145                 150                 155                 160

Asn Asp Ile Pro Lys Glu Gln Arg Ala Met Ile Thr Ser Glu Gly Ala
                165                 170                 175

Phe Lys Tyr Phe Ser Lys Gln Tyr Gly Ile Thr Pro Gly Tyr Ile Trp
            180                 185                 190

Glu Ile Asn Thr Glu Lys Gln Gly Thr Pro Glu Gln Met Arg Gln Ala
        195                 200                 205

Ile Glu Phe Val Lys Lys His Lys Leu Lys His Leu Leu Val Glu Thr
    210                 215                 220

Ser Val Asp Lys Lys Ala Met Glu Ser Leu Ser Glu Glu Thr Lys Lys
225                 230                 235                 240

Asp Ile Phe Gly Glu Val Tyr Thr Asp Ser Ile Gly Lys Glu Gly Thr
                245                 250                 255

Lys Gly Asp Ser Tyr Tyr Lys Met Met Lys Ser Asn Ile Glu Thr Val
            260                 265                 270

His Gly Ser Met Lys
        275
```

<210> SEQ ID NO 37
<211> LENGTH: 696
<212> TYPE: DNA

<213> ORGANISM: Staphylococcus epidermidis

<400> SEQUENCE: 37

```
ggtaagccag gagttaaaaa tcctgataca ggcgaagtag tcacaccacc agtggatgat     60
gtgacaaaac atggtccagt tgatggagat ccgattacgt caacggaaga aattccgttt    120
gataaaaaac gcgaattaga tccaaactta gcgccaggta cagagaaagt cgttcaaaaa    180
ggtgaaccag gaacaaaaac aattacaacg ccaacaacta agaacccatt aacaggagaa    240
aaagttggcg aaggtgaacc aacagaaaaa ataacaaaac aaccagtgga tgagattgtt    300
cattatggtg gtgaacaaat accacaaggt cataaagatg aatttgatcc aaatgcacct    360
gtagatagta aaactgaagt tccaggtaaa ccaggagtta aaaatcctga tacaggtgaa    420
gttgttaccc caccagtgga tgatgtgaca aaatatggtc cgaaagttgg taatccaatc    480
acatcaacgg aagagattcc atttgataag aaacgtgtat ttaatcctga tttaaaacca    540
ggtgaagagc gcgttaaaca aaaaggtgaa ccaggaacaa aaacaattac aacaccaata    600
ttagttaatc ctattacagg agaaaaagtt ggcgaaggta aatcaacaga aaaagtcact    660
aaacaacctg ttgacgaaat tgttgagtat ggtcca                              696
```

<210> SEQ ID NO 38
<211> LENGTH: 232
<212> TYPE: PRT
<213> ORGANISM: Staphylococcus epidermidis

<400> SEQUENCE: 38

```
Gly Lys Pro Gly Val Lys Asn Pro Asp Thr Gly Glu Val Val Thr Pro
1               5                   10                  15

Pro Val Asp Asp Val Thr Lys His Gly Pro Val Asp Gly Asp Pro Ile
            20                  25                  30

Thr Ser Thr Glu Glu Ile Pro Phe Asp Lys Lys Arg Glu Leu Asp Pro
        35                  40                  45

Asn Leu Ala Pro Gly Thr Glu Lys Val Val Gln Lys Gly Glu Pro Gly
    50                  55                  60

Thr Lys Thr Ile Thr Thr Pro Thr Thr Lys Asn Pro Leu Thr Gly Glu
65                  70                  75                  80

Lys Val Gly Glu Gly Glu Pro Thr Glu Lys Ile Thr Lys Gln Pro Val
                85                  90                  95

Asp Glu Ile Val His Tyr Gly Gly Glu Gln Ile Pro Gln Gly His Lys
            100                 105                 110

Asp Glu Phe Asp Pro Asn Ala Pro Val Asp Ser Lys Thr Glu Val Pro
        115                 120                 125

Gly Lys Pro Gly Val Lys Asn Pro Asp Thr Gly Glu Val Val Thr Pro
    130                 135                 140

Pro Val Asp Asp Val Thr Lys Tyr Gly Pro Lys Val Gly Asn Pro Ile
145                 150                 155                 160

Thr Ser Thr Glu Glu Ile Pro Phe Asp Lys Lys Arg Val Phe Asn Pro
                165                 170                 175

Asp Leu Lys Pro Gly Glu Glu Arg Val Lys Gln Lys Gly Glu Pro Gly
            180                 185                 190

Thr Lys Thr Ile Thr Thr Pro Ile Leu Val Asn Pro Ile Thr Gly Glu
        195                 200                 205

Lys Val Gly Glu Gly Lys Ser Thr Glu Lys Val Thr Lys Gln Pro Val
    210                 215                 220

Asp Glu Ile Val Glu Tyr Gly Pro
```

225 230

<210> SEQ ID NO 39
<211> LENGTH: 339
<212> TYPE: DNA
<213> ORGANISM: Staphylococcus aureus

<400> SEQUENCE: 39
gaaaaggaca aactaccggc aactcaaaaa gctaaagaaa tgcaaaatgt tccatataca 60
attgcagtag atggcattat ggctttcaat caatcttact taaatttacc aaaagatagc 120
caattatcat atttagattt aggaaataaa gttaaagctt tattatatga tgaacgtggt 180
gtaacacctg agaagattcg aaatgcaaaa tctgccgttt acacgattac ttggaaagat 240
ggtagtaaaa aagaagtgga tcttaagaaa gatagctaca cagcaaactt gtttgattca 300
aattcaatta aacaaattga tattaatgta aaaactaaa 339

<210> SEQ ID NO 40
<211> LENGTH: 117
<212> TYPE: PRT
<213> ORGANISM: Staphylococcus aureus

<400> SEQUENCE: 40

Glu Lys Asp Lys Leu Pro Ala Thr Gln Lys Ala Lys Glu Met Glu Thr
1 5 10 15

Gln Asn Val Pro Tyr Thr Ile Ala Val Asp Gly Ile Met Glu Thr Ala
20 25 30

Phe Asn Gln Ser Tyr Leu Asn Leu Pro Lys Asp Ser Gln Leu Ser Tyr
35 40 45

Leu Asp Leu Gly Asn Lys Val Lys Ala Leu Leu Tyr Asp Glu Arg Gly
50 55 60

Val Thr Pro Glu Lys Ile Arg Asn Ala Lys Ser Ala Val Tyr Thr Ile
65 70 75 80

Thr Trp Lys Asp Gly Ser Lys Lys Glu Val Asp Leu Lys Lys Asp Ser
85 90 95

Tyr Thr Ala Asn Leu Phe Asp Ser Asn Ser Ile Lys Gln Ile Asp Ile
100 105 110

Asn Val Lys Thr Lys
115

<210> SEQ ID NO 41
<211> LENGTH: 1965
<212> TYPE: DNA
<213> ORGANISM: Staphylococcus aureus

<400> SEQUENCE: 41
tcggaaaaaa caccaacgtc caatgcagcg gcacaaaaag aaacactaaa tcaaccggga 60
gaacaaggga acgcgataac gtcacatcaa atgcagtcag gaaagcaatt agacgatatg 120
cataaagaga atggtaaaag tggaacagtg acagaaggta aagacacgct tcaatcatcg 180
aagcatcaat caacacaaaa tagtaaaaca atcagaacgc aaaatgataa tcaagtaaag 240
caagattctg aacgacaagg ttctaaacag tcacaccaaa ataatgcgac taataatact 300
gaacgtcaaa atgatcaggt tcaaaatacc catcatgctg aacgtaaggg atcacaatcg 360
acaacgtcac aatcgaatga tgttgataaa tcacaaccat ccattccggc acaaaaggta 420
ttacccaatc atgataaagc agcaccaact tcaactacac ccccgtctaa tgataaaact 480
gcacctaaat caacaaaagc acaagatgca accacggaca aacacccaaa tcaacaagat 540

```
acacatcaac ccgcgcatca aatcatagat gcaaagcaag atgatactgt tcgccaaagt    600
gaacagaaac cacaagttgg cgatttaagt aaacatatcg atggtcaaaa ttccccagag    660
aaaccgacag ataaaaatac tgataataaa caactaatca aagatgcgct tcaagcgcct    720
aaaacacgtt cgactacaaa tgcagcagca gatgctaaaa aggttcgacc acttaaagcg    780
aatcaagtac aaccacttaa caaatatcca gttgtttttg tacatggatt tttaggatta    840
gtaggcgata atgcacctgc tttatatcca aattattggg gtggaaataa atttaaagtt    900
atcgaggaat tgagaaagca aggctataat gtacatcaag caagtgtaag tgcatttggt    960
agtaactatg atcgcgctgt agaactttat tattacatta aaggtggtcg cgtagattat   1020
ggcgcagcac atgcagctaa atacggacat gagcgctatg gtaagactta taaaggaatc   1080
atgcctaatt gggaacctgg taaaaaggta catcttgtag ggcatagtat gggtggtcaa   1140
acaattcgtt taatggaaga gtttttaaga aatggtaaca aagaagaaat tgcctatcat   1200
aaagcgcatg gtggagaaat atcaccatta ttcactggtg gtcataacaa tatggttgca   1260
tcaatcacaa cattagcaac accacataat ggttcacaag cagctgataa gtttggaaat   1320
acagaagctg ttagaaaaat catgttcgct ttaaatcgat ttatgggtaa caagtattcg   1380
aatatcgatt taggattaac gcaatggggc tttaaacaat taccaaatga gagttacatt   1440
gactatataa aacgcgttag taaaagcaaa atttggacat cagacgataa tgctgcctat   1500
gatttaacgt tagatggctc tgcaaaattg aacaacatga caagtatgaa tcctaacatt   1560
acgtatacga cttatacagg tgtgtcttca catactggtc cattaggtta tgaaaatcct   1620
gatttaggta catttttctt aatggataca acgagtagaa ttattggtca tgatgcaaga   1680
gaagaatggc gtaaaaatga tggtgtcgta ccagtgattt cgtcgttaca tccatccaat   1740
caaccattta ttaatgttac gaatgatgaa cctgccacac gcagaggtat ctggcaagtt   1800
aaaccaatca tacaaggatg ggatcatgtc gattttatcg gtgtggactt cctggatttc   1860
aaacgtaaag gtgcagaact tgccaacttc tatacaggta ttataaatga cttgttgcgt   1920
gtggaagcga ctgaaagtaa aggaacacaa ttgaaagcaa gttaa                   1965
```

<210> SEQ ID NO 42
<211> LENGTH: 658
<212> TYPE: PRT
<213> ORGANISM: Staphylococcus aureus

<400> SEQUENCE: 42

```
Ser Glu Lys Thr Pro Thr Ser Asn Ala Ala Ala Gln Lys Glu Thr Leu
1               5                   10                  15

Asn Gln Pro Gly Glu Gln Gly Asn Ala Ile Thr Ser His Gln Met Glu
            20                  25                  30

Thr Gln Ser Gly Lys Gln Leu Asp Asp Met Glu Thr His Lys Glu Asn
        35                  40                  45

Gly Lys Ser Gly Thr Val Thr Glu Gly Lys Asp Thr Leu Gln Ser Ser
    50                  55                  60

Lys His Gln Ser Thr Gln Asn Ser Lys Thr Ile Arg Thr Gln Asn Asp
65                  70                  75                  80

Asn Gln Val Lys Gln Asp Ser Glu Arg Gln Gly Ser Lys Gln Ser His
                85                  90                  95

Gln Asn Asn Ala Thr Asn Asn Thr Glu Arg Gln Asn Asp Gln Val Gln
            100                 105                 110

Asn Thr His His Ala Glu Arg Lys Gly Ser Gln Ser Thr Thr Ser Gln
```

```
        115                 120                 125

Ser Asn Asp Val Asp Lys Ser Gln Pro Ser Ile Pro Ala Gln Lys Val
    130                 135                 140

Leu Pro Asn His Asp Lys Ala Ala Pro Thr Ser Thr Thr Pro Pro Ser
145                 150                 155                 160

Asn Asp Lys Thr Ala Pro Lys Ser Thr Lys Ala Gln Asp Ala Thr Thr
                165                 170                 175

Asp Lys His Pro Asn Gln Gln Asp Thr His Gln Pro Ala His Gln Ile
            180                 185                 190

Ile Asp Ala Lys Gln Asp Asp Thr Val Arg Gln Ser Glu Gln Lys Pro
        195                 200                 205

Gln Val Gly Asp Leu Ser Lys His Ile Asp Gly Gln Asn Ser Pro Glu
    210                 215                 220

Lys Pro Thr Asp Lys Asn Thr Asp Asn Lys Gln Leu Ile Lys Asp Ala
225                 230                 235                 240

Leu Gln Ala Pro Lys Thr Arg Ser Thr Thr Asn Ala Ala Ala Asp Ala
                245                 250                 255

Lys Lys Val Arg Pro Leu Lys Ala Asn Gln Val Gln Pro Leu Asn Lys
            260                 265                 270

Tyr Pro Val Val Phe Val His Gly Phe Leu Gly Leu Val Gly Asp Asn
        275                 280                 285

Ala Pro Ala Leu Tyr Pro Asn Tyr Trp Gly Gly Asn Lys Phe Lys Val
    290                 295                 300

Ile Glu Glu Leu Arg Lys Gln Gly Tyr Asn Val His Gln Ala Ser Val
305                 310                 315                 320

Ser Ala Phe Gly Ser Asn Tyr Asp Arg Ala Val Glu Leu Tyr Tyr Tyr
                325                 330                 335

Ile Lys Gly Gly Arg Val Asp Tyr Gly Ala Ala His Ala Ala Lys Tyr
            340                 345                 350

Gly His Glu Arg Tyr Gly Lys Thr Tyr Lys Gly Ile Met Pro Asn Trp
        355                 360                 365

Glu Pro Gly Lys Lys Val His Leu Val Gly His Ser Met Gly Gly Gln
    370                 375                 380

Thr Ile Arg Leu Met Glu Glu Phe Leu Arg Asn Gly Asn Lys Glu Glu
385                 390                 395                 400

Ile Ala Tyr His Lys Ala His Gly Gly Glu Ile Ser Pro Leu Phe Thr
                405                 410                 415

Gly Gly His Asn Asn Met Val Ala Ser Ile Thr Thr Leu Ala Thr Pro
            420                 425                 430

His Asn Gly Ser Gln Ala Ala Asp Lys Phe Gly Asn Thr Glu Ala Val
        435                 440                 445

Arg Lys Ile Met Phe Ala Leu Asn Arg Phe Met Gly Asn Lys Tyr Ser
    450                 455                 460

Asn Ile Asp Leu Gly Leu Thr Gln Trp Gly Phe Lys Gln Leu Pro Asn
465                 470                 475                 480

Glu Ser Tyr Ile Asp Tyr Ile Lys Arg Val Ser Lys Ser Lys Ile Trp
                485                 490                 495

Thr Ser Asp Asp Asn Ala Ala Tyr Asp Leu Thr Leu Asp Gly Ser Ala
            500                 505                 510

Lys Leu Asn Asn Met Thr Ser Met Asn Pro Asn Ile Thr Tyr Thr Thr
        515                 520                 525

Tyr Thr Gly Val Ser Ser His Thr Gly Pro Leu Gly Tyr Glu Asn Pro
    530                 535                 540
```

```
Asp Leu Gly Thr Phe Phe Leu Met Asp Thr Thr Ser Arg Ile Ile Gly
545                 550                 555                 560

His Asp Ala Arg Glu Glu Trp Arg Lys Asn Asp Gly Val Val Pro Val
                565                 570                 575

Ile Ser Ser Leu His Pro Ser Asn Gln Pro Phe Ile Asn Val Thr Asn
            580                 585                 590

Asp Glu Pro Ala Thr Arg Arg Gly Ile Trp Gln Val Lys Pro Ile Ile
        595                 600                 605

Gln Gly Trp Asp His Val Asp Phe Ile Gly Val Asp Phe Leu Asp Phe
    610                 615                 620

Lys Arg Lys Gly Ala Glu Leu Ala Asn Phe Tyr Thr Gly Ile Ile Asn
625                 630                 635                 640

Asp Leu Leu Arg Val Glu Ala Thr Glu Ser Lys Gly Thr Gln Leu Lys
                645                 650                 655

Ala Ser


<210> SEQ ID NO 43
<211> LENGTH: 609
<212> TYPE: DNA
<213> ORGANISM: Staphylococcus aureus

<400> SEQUENCE: 43

gaagtaaacg ttgatcaagc acacttagtt gacttagcgc ataatcacca agatcaatta     60

aatgcagctc caatcaaaga tggtgcatat gacatccact ttgtaaaaga tggtttccaa    120

tataacttta cttcaaatgg tactacatgg tcatggagct atgaagcagc taatggtcaa    180

actgctggtt tctcaaacgt tgcaggtgca gactacacta cttcatacaa ccaaggttca    240

gatgtacaat cagtaagcta caatgcacaa tcaagtaact caaacgttga agctgtttca    300

gctccaactt accataacta cagcacttca actacttcaa gttcagtgag attaagcaat    360

ggtaatactg caggtgctac tggttcatca gcagctcaaa tcatggctca acgtactggt    420

gtttcagctt ctacatgggc tgcaatcatc gctcgtgaat caaatggtca agtaaatgct    480

tacaacccat caggtgcttc aggtttattc caaactatgc caggttgggg tccgacaaac    540

actgttgacc aacaaatcaa cgcagctgtt aaagcataca aagcacaagg tttaggtgct    600

tggggattc                                                            609


<210> SEQ ID NO 44
<211> LENGTH: 203
<212> TYPE: PRT
<213> ORGANISM: Staphylococcus aureus

<400> SEQUENCE: 44

Glu Val Asn Val Asp Gln Ala His Leu Val Asp Leu Ala His Asn His
1               5                   10                  15

Gln Asp Gln Leu Asn Ala Ala Pro Ile Lys Asp Gly Ala Tyr Asp Ile
            20                  25                  30

His Phe Val Lys Asp Gly Phe Gln Tyr Asn Phe Thr Ser Asn Gly Thr
        35                  40                  45

Thr Trp Ser Trp Ser Tyr Glu Ala Ala Asn Gly Gln Thr Ala Gly Phe
    50                  55                  60

Ser Asn Val Ala Gly Ala Asp Tyr Thr Thr Ser Tyr Asn Gln Gly Ser
65                  70                  75                  80

Asp Val Gln Ser Val Ser Tyr Asn Ala Gln Ser Ser Asn Ser Asn Val
                85                  90                  95
```

```
Glu Ala Val Ser Ala Pro Thr Tyr His Asn Tyr Ser Thr Ser Thr Thr
            100                 105                 110

Ser Ser Ser Val Arg Leu Ser Asn Gly Asn Thr Ala Gly Ala Thr Gly
        115                 120                 125

Ser Ser Ala Ala Gln Ile Met Ala Gln Arg Thr Gly Val Ser Ala Ser
    130                 135                 140

Thr Trp Ala Ala Ile Ile Ala Arg Glu Ser Asn Gly Gln Val Asn Ala
145                 150                 155                 160

Tyr Asn Pro Ser Gly Ala Ser Gly Leu Phe Gln Thr Met Pro Gly Trp
                165                 170                 175

Gly Pro Thr Asn Thr Val Asp Gln Gln Ile Asn Ala Ala Val Lys Ala
            180                 185                 190

Tyr Lys Ala Gln Gly Leu Gly Ala Trp Gly Phe
        195                 200
```

<210> SEQ ID NO 45
<211> LENGTH: 1143
<212> TYPE: DNA
<213> ORGANISM: Streptococcus agalactiae

<400> SEQUENCE: 45

```
gcttcaaaaa caactatcaa actttgggtc ccaacagatt caaaagcgtc ttataaagca     60

attgttaaaa aattcgagaa ggaaaacaaa ggcgttactg taaaaatgat tgagtctaat    120

gactccaaag ctcaagaaaa cgtaaaaaaa gacccaagca aggcagccga tgtattctca    180

cttccacatg accaacttgg tcaattagta gaatctggtg ttatccaaga aattccagag    240

caatactcaa aagaaattgc taaaaacgac actaaacaat cacttactgg tgcacaatat    300

aaagggaaaa cttatgcatt cccatttggt attgaatctc aagttcttta ttataataaa    360

acaaagttaa ctgctgacga cgttaaatca tacgaaacaa ttacaagcaa agggaaattc    420

ggtcaacagc ttaaagcagc taactcatat gtaacaggtc ctcttttcct ttctgtaggc    480

gacactttat ttggtaaatc tggtgaagat gccaaaggca ctaactgggg taatgaagca    540

ggtgtttctg tccttaaatg gattgcagat caaaagaaaa atgatggttt tgtcaacttg    600

acagctgaaa atacaatgtc taaatttggc gatggttctg ttcatgcttt tgaaagtgga    660

ccatgggatt acgacgctgc taaaaaagct gtcggtgaag ataaaatcgg tgttgctgtt    720

tacccaacaa tgaaaatcgg tgacaaagaa gttcaacaaa aagcattctt gggcgttaaa    780

ctttatgccg ttaaccaagc acctgctggt tcaaacacta aacgaatctc agctagctac    840

aaactcgctg catatctaac taatgctgaa agtcaaaaaa ttcaattcga aaaacgtcat    900

atcgttcctg ctaactcatc aattcaatct tctgatagcg tccaaaaaga tgaacttgca    960

aaagcagtta tcgaaatggg tagctcagat aaatatacaa cggttatgcc taagttgagt   1020

caaatgtcaa cattctggac agaaagtgct gctattctta gcgatactta cagtggtaaa   1080

atcaaatcta gcgattacct taaacgtcta aaacaattcg ataaagacat cgctaaaaca   1140

aaa                                                                 1143
```

<210> SEQ ID NO 46
<211> LENGTH: 381
<212> TYPE: PRT
<213> ORGANISM: Streptococcus agalactiae

<400> SEQUENCE: 46

```
Ala Ser Lys Thr Thr Ile Lys Leu Trp Val Pro Thr Asp Ser Lys Ala
```

```
1               5                   10                  15

Ser Tyr Lys Ala Ile Val Lys Lys Phe Glu Lys Glu Asn Lys Gly Val
            20                  25                  30

Thr Val Lys Met Ile Glu Ser Asn Asp Ser Lys Ala Gln Glu Asn Val
        35                  40                  45

Lys Lys Asp Pro Ser Lys Ala Ala Asp Val Phe Ser Leu Pro His Asp
    50                  55                  60

Gln Leu Gly Gln Leu Val Glu Ser Gly Val Ile Gln Glu Ile Pro Glu
65                  70                  75                  80

Gln Tyr Ser Lys Glu Ile Ala Lys Asn Asp Thr Lys Gln Ser Leu Thr
                85                  90                  95

Gly Ala Gln Tyr Lys Gly Lys Thr Tyr Ala Phe Pro Phe Gly Ile Glu
            100                 105                 110

Ser Gln Val Leu Tyr Tyr Asn Lys Thr Lys Leu Thr Ala Asp Asp Val
        115                 120                 125

Lys Ser Tyr Glu Thr Ile Thr Ser Lys Gly Lys Phe Gly Gln Gln Leu
    130                 135                 140

Lys Ala Ala Asn Ser Tyr Val Thr Gly Pro Leu Phe Leu Ser Val Gly
145                 150                 155                 160

Asp Thr Leu Phe Gly Lys Ser Gly Glu Asp Ala Lys Gly Thr Asn Trp
                165                 170                 175

Gly Asn Glu Ala Gly Val Ser Val Leu Lys Trp Ile Ala Asp Gln Lys
            180                 185                 190

Lys Asn Asp Gly Phe Val Asn Leu Thr Ala Glu Asn Thr Met Ser Lys
        195                 200                 205

Phe Gly Asp Gly Ser Val His Ala Phe Glu Ser Gly Pro Trp Asp Tyr
    210                 215                 220

Asp Ala Ala Lys Lys Ala Val Gly Glu Asp Lys Ile Gly Val Ala Val
225                 230                 235                 240

Tyr Pro Thr Met Lys Ile Gly Asp Lys Glu Val Gln Gln Lys Ala Phe
                245                 250                 255

Leu Gly Val Lys Leu Tyr Ala Val Asn Gln Ala Pro Ala Gly Ser Asn
            260                 265                 270

Thr Lys Arg Ile Ser Ala Ser Tyr Lys Leu Ala Ala Tyr Leu Thr Asn
        275                 280                 285

Ala Glu Ser Gln Lys Ile Gln Phe Glu Lys Arg His Ile Val Pro Ala
    290                 295                 300

Asn Ser Ser Ile Gln Ser Ser Asp Ser Val Gln Lys Asp Glu Leu Ala
305                 310                 315                 320

Lys Ala Val Ile Glu Met Gly Ser Ser Asp Lys Tyr Thr Thr Val Met
                325                 330                 335

Pro Lys Leu Ser Gln Met Ser Thr Phe Trp Thr Glu Ser Ala Ala Ile
            340                 345                 350

Leu Ser Asp Thr Tyr Ser Gly Lys Ile Lys Ser Ser Asp Tyr Leu Lys
        355                 360                 365

Arg Leu Lys Gln Phe Asp Lys Asp Ile Ala Lys Thr Lys
    370                 375                 380
```

<210> SEQ ID NO 47
<211> LENGTH: 1458
<212> TYPE: DNA
<213> ORGANISM: Streptococcus agalactiae

<400> SEQUENCE: 47

```
gcagaaacta ttaatccaga aacaagcctg acaatggcaa cagcatcaac agaaagttct     60

tctgaagcag agaaacagga aaaaacacaa cctacagatt cagaaactgc ttcaccttca    120

gccgaaggaa gtatctcaac agaaaaaaca gagattggta cgacagagac atcatcaagc    180

aatgaatcat catcaagttc atcacatcaa tcttcttcca acgaagatgc taaaacatct    240

gattctgctt caacagcatc tactcctagc actaatacta caaacagtag tcaagcagac    300

agtaagccag gtcaatcaac aaagactgaa ttaaaacctg agcctacctt accattagta    360

gagcctaaaa taactcccgc tccgtctcag atagaaagtg ttcagacaaa tcagaatgct    420

tctgttcctg ctttatcctt tgatgataac ttattatcaa caccgatttc accagtgaca    480

gcaacgccat tctacgtaga acactggtct ggtcaggatg cctactctca ctatttattg    540

tcacatcgtt acggtatcaa agctgaacaa ttagatgggt acttaaaatc tttagggatt    600

caatatgatt ctaatcgtat caatggtgct aagttattac aatgggaaaa agatagtggt    660

ttagatgtcc gtgctattgt agctattgct gtccttgaaa gttcattggg aactcaaggg    720

gtggctaaga tgccaggtgc taatatgttt ggttatggtg cctttgatca tgactctagc    780

catgctagtg cttataatga tgaagaagca attatgttgt tgacaaaaaa tacaattatt    840

aaaaacaaca actctagctt tgaaatccaa gatttgaaag cacagaaatt atcttctgga    900

caacttaata cagttactga gggtggtgtt tattatacag ataactctgg aactggtaaa    960

cgtcgtgccc agattatgga agatttagac cgctggattg atcaacatgg agggacacca   1020

gaaattcctg ctgccttgaa agctttatcg acagcaagtt tagcagattt accaagtggt   1080

tttagcttat caacagcagt taacacagct agctatattg catcaactta tccatggggt   1140

gaatgtacat ggtatgtctt taaccgagct aaagagttag gttatacatt tgatccattt   1200

atgggtaatg gtggagattg gcaacataag gctggttttg aaacaacaca ttcaccaaaa   1260

gtaggctatg ctgtatcatt ttcaccagga caagctggtg ctgatggcac ttacggtcac   1320

gtagctattg ttgaagaagt taaaaaagat ggttcagttc ttatttcaga atctaatgca   1380

atgggacgtg gtattgtctc ttaccgtact tttagttcag cacaagctgc acaattaact   1440

tatgttattg gccataaa                                                  1458
```

<210> SEQ ID NO 48
<211> LENGTH: 486
<212> TYPE: PRT
<213> ORGANISM: Streptococcus agalactiae

<400> SEQUENCE: 48

```
Ala Glu Thr Ile Asn Pro Glu Thr Ser Leu Thr Met Ala Thr Ala Ser
1               5                   10                  15

Thr Glu Ser Ser Ser Glu Ala Glu Lys Gln Glu Lys Thr Gln Pro Thr
            20                  25                  30

Asp Ser Glu Thr Ala Ser Pro Ser Ala Glu Gly Ser Ile Ser Thr Glu
        35                  40                  45

Lys Thr Glu Ile Gly Thr Thr Glu Thr Ser Ser Ser Asn Glu Ser Ser
    50                  55                  60

Ser Ser Ser Ser His Gln Ser Ser Ser Asn Glu Asp Ala Lys Thr Ser
65                  70                  75                  80

Asp Ser Ala Ser Thr Ala Ser Thr Pro Ser Thr Asn Thr Thr Asn Ser
                85                  90                  95

Ser Gln Ala Asp Ser Lys Pro Gly Gln Ser Thr Lys Thr Glu Leu Lys
            100                 105                 110
```

```
Pro Glu Pro Thr Leu Pro Leu Val Glu Pro Lys Ile Thr Pro Ala Pro
        115                 120                 125

Ser Gln Ile Glu Ser Val Gln Thr Asn Gln Asn Ala Ser Val Pro Ala
    130                 135                 140

Leu Ser Phe Asp Asp Asn Leu Leu Ser Thr Pro Ile Ser Pro Val Thr
145                 150                 155                 160

Ala Thr Pro Phe Tyr Val Glu His Trp Ser Gly Gln Asp Ala Tyr Ser
                165                 170                 175

His Tyr Leu Leu Ser His Arg Tyr Gly Ile Lys Ala Glu Gln Leu Asp
            180                 185                 190

Gly Tyr Leu Lys Ser Leu Gly Ile Gln Tyr Asp Ser Asn Arg Ile Asn
        195                 200                 205

Gly Ala Lys Leu Leu Gln Trp Glu Lys Asp Ser Gly Leu Asp Val Arg
    210                 215                 220

Ala Ile Val Ala Ile Ala Val Leu Glu Ser Ser Leu Gly Thr Gln Gly
225                 230                 235                 240

Val Ala Lys Met Pro Gly Ala Asn Met Phe Gly Tyr Gly Ala Phe Asp
                245                 250                 255

His Asp Ser Ser His Ala Ser Ala Tyr Asn Asp Glu Glu Ala Ile Met
            260                 265                 270

Leu Leu Thr Lys Asn Thr Ile Ile Lys Asn Asn Asn Ser Ser Phe Glu
        275                 280                 285

Ile Gln Asp Leu Lys Ala Gln Lys Leu Ser Ser Gly Gln Leu Asn Thr
    290                 295                 300

Val Thr Glu Gly Gly Val Tyr Tyr Thr Asp Asn Ser Gly Thr Gly Lys
305                 310                 315                 320

Arg Arg Ala Gln Ile Met Glu Asp Leu Asp Arg Trp Ile Asp Gln His
                325                 330                 335

Gly Gly Thr Pro Glu Ile Pro Ala Ala Leu Lys Ala Leu Ser Thr Ala
            340                 345                 350

Ser Leu Ala Asp Leu Pro Ser Gly Phe Ser Leu Ser Thr Ala Val Asn
        355                 360                 365

Thr Ala Ser Tyr Ile Ala Ser Thr Tyr Pro Trp Gly Glu Cys Thr Trp
    370                 375                 380

Tyr Val Phe Asn Arg Ala Lys Glu Leu Gly Tyr Thr Phe Asp Pro Phe
385                 390                 395                 400

Met Gly Asn Gly Gly Asp Trp Gln His Lys Ala Gly Phe Glu Thr Thr
                405                 410                 415

His Ser Pro Lys Val Gly Tyr Ala Val Ser Phe Ser Pro Gly Gln Ala
            420                 425                 430

Gly Ala Asp Gly Thr Tyr Gly His Val Ala Ile Val Glu Glu Val Lys
        435                 440                 445

Lys Asp Gly Ser Val Leu Ile Ser Glu Ser Asn Ala Met Gly Arg Gly
    450                 455                 460

Ile Val Ser Tyr Arg Thr Phe Ser Ser Ala Gln Ala Ala Gln Leu Thr
465                 470                 475                 480

Tyr Val Ile Gly His Lys
                485
```

<210> SEQ ID NO 49
<211> LENGTH: 1230
<212> TYPE: DNA
<213> ORGANISM: Streptcococcus agalactiae

<400> SEQUENCE: 49

```
gcacaagaaa cagatacgac gtggacagca cgtactgttt cagaggtaaa ggctgatttg     60

gtaaagcaag acaataaatc atcatatact gtgaaatatg gtgatacact aagcgttatt    120

tcagaagcaa tgtcaattga tatgaatgtc ttagcaaaaa taaataacat tgcagatatc    180

aatcttattt atcctgagac aacactgaca gtaacttacg atcagaagag tcatactgcc    240

acttcaatga aaatagaaac accagcaaca aatgctgctg gtcaaacaac agctactgtg    300

gatttgaaaa ccaatcaagt ttctgttgca gaccaaaaag tttctctcaa tacaatttcg    360

gaaggtatga caccagaagc agcaacaacg attgtttcgc caatgaagac atattcttct    420

gcgccagctt tgaaatcaaa agaagtatta gcacaagagc aagctgttag tcaagcagca    480

gctaatgaac aggtatcacc agctcctgtg aagtcgatta cttcagaagt tccagcagct    540

aaagaggaag ttaaaccaac tcagacgtca gtcagtcagt caacaacagt atcaccagct    600

tctgttgccg ctgaaacacc agctccagta gctaaagtag caccggtaag aactgtagca    660

gcccctagag tggcaagtgt taaagtagtc actcctaaag tagaaactgg tgcatcacca    720

gagcatgtat cagctccagc agttcctgtg actacgactt caccagctac agacagtaag    780

ttacaagcga ctgaagttaa gagcgttccg gtagcacaaa aagctccaac agcaacaccg    840

gtagcacaac cagcttcaac aacaaatgca gtagctgcac atcctgaaaa tgcagggctc    900

caacctcatg ttgcagctta taaagaaaaa gtagcgtcaa cttatggagt taatgaattc    960

agtacatacc gtgcgggaga tccaggtgat catggtaaag gtttagcagt tgactttatt   1020

gtaggtacta atcaagcact tggtaataaa gttgcacagt actctacaca aaatatggca   1080

gcaaataaca tttcatatgt tatctggcaa caaaagtttt actcaaatac aaacagtatt   1140

tatggacctg ctaatacttg gaatgcaatg ccagatcgtg gtggcgttac tgccaaccac   1200

tatgaccacg ttcacgtatc atttaacaaa                                     1230
```

```
<210> SEQ ID NO 50
<211> LENGTH: 410
<212> TYPE: PRT
<213> ORGANISM: Streptococcus agalactiae

<400> SEQUENCE: 50

Ala Gln Glu Thr Asp Thr Thr Trp Thr Ala Arg Thr Val Ser Glu Val
1               5                   10                  15

Lys Ala Asp Leu Val Lys Gln Asp Asn Lys Ser Ser Tyr Thr Val Lys
            20                  25                  30

Tyr Gly Asp Thr Leu Ser Val Ile Ser Glu Ala Met Ser Ile Asp Met
        35                  40                  45

Asn Val Leu Ala Lys Ile Asn Asn Ile Ala Asp Ile Asn Leu Ile Tyr
    50                  55                  60

Pro Glu Thr Thr Leu Thr Val Thr Tyr Asp Gln Lys Ser His Thr Ala
65                  70                  75                  80

Thr Ser Met Lys Ile Glu Thr Pro Ala Thr Asn Ala Ala Gly Gln Thr
                85                  90                  95

Thr Ala Thr Val Asp Leu Lys Thr Asn Gln Val Ser Val Ala Asp Gln
            100                 105                 110

Lys Val Ser Leu Asn Thr Ile Ser Glu Gly Met Thr Pro Glu Ala Ala
        115                 120                 125

Thr Thr Ile Val Ser Pro Met Lys Thr Tyr Ser Ser Ala Pro Ala Leu
    130                 135                 140

Lys Ser Lys Glu Val Leu Ala Gln Glu Gln Ala Val Ser Gln Ala Ala
```

```
145                 150                 155                 160

Ala Asn Glu Gln Val Ser Pro Ala Pro Val Lys Ser Ile Thr Ser Glu
                165                 170                 175

Val Pro Ala Ala Lys Glu Glu Val Lys Pro Thr Gln Thr Ser Val Ser
            180                 185                 190

Gln Ser Thr Thr Val Ser Pro Ala Ser Val Ala Ala Glu Thr Pro Ala
        195                 200                 205

Pro Val Ala Lys Val Ala Pro Val Arg Thr Val Ala Ala Pro Arg Val
    210                 215                 220

Ala Ser Val Lys Val Val Thr Pro Lys Val Glu Thr Gly Ala Ser Pro
225                 230                 235                 240

Glu His Val Ser Ala Pro Ala Val Pro Val Thr Thr Thr Ser Pro Ala
                245                 250                 255

Thr Asp Ser Lys Leu Gln Ala Thr Glu Val Lys Ser Val Pro Val Ala
            260                 265                 270

Gln Lys Ala Pro Thr Ala Thr Pro Val Ala Gln Pro Ala Ser Thr Thr
        275                 280                 285

Asn Ala Val Ala Ala His Pro Glu Asn Ala Gly Leu Gln Pro His Val
    290                 295                 300

Ala Ala Tyr Lys Glu Lys Val Ala Ser Thr Tyr Gly Val Asn Glu Phe
305                 310                 315                 320

Ser Thr Tyr Arg Ala Gly Asp Pro Gly Asp His Gly Lys Gly Leu Ala
                325                 330                 335

Val Asp Phe Ile Val Gly Thr Asn Gln Ala Leu Gly Asn Lys Val Ala
            340                 345                 350

Gln Tyr Ser Thr Gln Asn Met Ala Ala Asn Asn Ile Ser Tyr Val Ile
        355                 360                 365

Trp Gln Gln Lys Phe Tyr Ser Asn Thr Asn Ser Ile Tyr Gly Pro Ala
    370                 375                 380

Asn Thr Trp Asn Ala Met Pro Asp Arg Gly Gly Val Thr Ala Asn His
385                 390                 395                 400

Tyr Asp His Val His Val Ser Phe Asn Lys
                405                 410
```

<210> SEQ ID NO 51
<211> LENGTH: 681
<212> TYPE: DNA
<213> ORGANISM: Streptococcus agalactiae

<400> SEQUENCE: 51

```
gctgatcaag tgacaactcc acaagtggta aatcatgtaa acagtaataa tcaagcccag     60

caaatggctc aaaagcttga tcaagatagc attcagttga gaaatatcaa agataatgtt    120

cagggaacag attatgaaaa aacggttaat gaggctatta ctagtgttga aaaattaaag    180

acttcattgc gtgccaaccc tgagacagtt tatgatttga attctattgg tagtcgtgta    240

gaagccttaa cagatgtgat tgaagcaatc acttttttcaa ctcaacattt agcaaataag    300

gttagtcaag caaatattga tatgggattt gggataacta agctggttat tcgcatttta    360

gatccatttg cttcagttga ttcaattaaa gctcaagtta acgatgtaaa ggcattagaa    420

caaaaggttt taacttatcc tgatttaaaa ccaactgata gagctaccat ctatacaaaa    480

tcaaaacttg ataaggaaat ctggaataca cgctttacta gagataaaaa agtacttaac    540

gtcaaagaat ttaaagttta caatacttta aataaagcaa tcacacatgc tgttggagtt    600

cagttgaatc caaatgttac ggtacaacaa gttgatcaag agattgtaac attacaagca    660
```

gcacttcaaa cagcattaaa a 681

<210> SEQ ID NO 52
<211> LENGTH: 227
<212> TYPE: PRT
<213> ORGANISM: Streptococcus agalactiae

<400> SEQUENCE: 52

```
Ala Asp Gln Val Thr Thr Pro Gln Val Val Asn His Val Asn Ser Asn
1               5                   10                  15

Asn Gln Ala Gln Gln Met Ala Gln Lys Leu Asp Gln Asp Ser Ile Gln
            20                  25                  30

Leu Arg Asn Ile Lys Asp Asn Val Gln Gly Thr Asp Tyr Glu Lys Thr
        35                  40                  45

Val Asn Glu Ala Ile Thr Ser Val Glu Lys Leu Lys Thr Ser Leu Arg
    50                  55                  60

Ala Asn Pro Glu Thr Val Tyr Asp Leu Asn Ser Ile Gly Ser Arg Val
65                  70                  75                  80

Glu Ala Leu Thr Asp Val Ile Glu Ala Ile Thr Phe Ser Thr Gln His
                85                  90                  95

Leu Ala Asn Lys Val Ser Gln Ala Asn Ile Asp Met Gly Phe Gly Ile
            100                 105                 110

Thr Lys Leu Val Ile Arg Ile Leu Asp Pro Phe Ala Ser Val Asp Ser
        115                 120                 125

Ile Lys Ala Gln Val Asn Asp Val Lys Ala Leu Glu Gln Lys Val Leu
    130                 135                 140

Thr Tyr Pro Asp Leu Lys Pro Thr Asp Arg Ala Thr Ile Tyr Thr Lys
145                 150                 155                 160

Ser Lys Leu Asp Lys Glu Ile Trp Asn Thr Arg Phe Thr Arg Asp Lys
                165                 170                 175

Lys Val Leu Asn Val Lys Glu Phe Lys Val Tyr Asn Thr Leu Asn Lys
            180                 185                 190

Ala Ile Thr His Ala Val Gly Val Gln Leu Asn Pro Asn Val Thr Val
        195                 200                 205

Gln Gln Val Asp Gln Glu Ile Val Thr Leu Gln Ala Ala Leu Gln Thr
    210                 215                 220

Ala Leu Lys
225
```

<210> SEQ ID NO 53
<211> LENGTH: 1098
<212> TYPE: DNA
<213> ORGANISM: Chlamydia pneumoniae

<400> SEQUENCE: 53

```
ctgcctgtag ggaacccttc tgatccaagc ttattaattg atggtacaat atgggaaggt     60

gctgcaggag atccttgcga tccttgcgct acttggtgcg acgctattag cttacgtgct    120

ggattttacg gagactatgt tttcgaccgt atcttaaaag tagatgcacc taaaacattt    180

tctatgggag ccaagcctac tggatccgct gctgcaaact atactactgc cgtagataga    240

cctaacccgg cctacaataa gcatttacac gatgcagagt ggttcactaa tgcaggcttc    300

attgccttaa acatttggga tcgctttgat gttttctgta ctttaggagc ttctaatggt    360

tacattagag gaaactctac agcgttcaat ctcgttggtt tattcggagt taaaggtact    420

actgtaaatg caaatgaact accaaacgtt tctttaagta acggagttgt tgaactttac    480
```

```
acagacacct ctttctcttg gagcgtaggc gctcgtggag ccttatggga atgcggttgt    540

gcaactttgg gagctgaatt ccaatatgca cagtccaaac ctaaagttga agaacttaat    600

gtgatctgta acgtatcgca attctctgta aacaaaccca agggctataa aggcgttgct    660

ttccccttgc caacagacgc tggcgtagca acagctactg gaacaaagtc tgcgaccatc    720

aattatcatg aatggcaagt aggagcctct ctatcttaca gactaaactc tttagtgcca    780

tacattggag tacaatggtc tcgagcaact tttgatgctg ataacatccg cattgctcag    840

ccaaaactac ctacagctgt tttaaactta actgcatgga acccttcttt actaggaaat    900

gccacagcat tgtctactac tgattcgttc tcagacttca tgcaaattgt ttcctgtcag    960

atcaacaagt ttaaatctag aaaagcttgt ggagttactg taggagctac tttagttgat   1020

gctgataaat ggtcacttac tgcagaagct cgtttaatta acgagagagc tgctcacgta   1080

tctggtcagt tcagattc                                                 1098
```

<210> SEQ ID NO 54
<211> LENGTH: 366
<212> TYPE: PRT
<213> ORGANISM: Chlamydia pneumoniae

<400> SEQUENCE: 54

```
Leu Pro Val Gly Asn Pro Ser Asp Pro Ser Leu Leu Ile Asp Gly Thr
1               5                   10                  15

Ile Trp Glu Gly Ala Ala Gly Asp Pro Cys Asp Pro Cys Ala Thr Trp
            20                  25                  30

Cys Asp Ala Ile Ser Leu Arg Ala Gly Phe Tyr Gly Asp Tyr Val Phe
        35                  40                  45

Asp Arg Ile Leu Lys Val Asp Ala Pro Lys Thr Phe Ser Met Gly Ala
    50                  55                  60

Lys Pro Thr Gly Ser Ala Ala Ala Asn Tyr Thr Thr Ala Val Asp Arg
65                  70                  75                  80

Pro Asn Pro Ala Tyr Asn Lys His Leu His Asp Ala Glu Trp Phe Thr
                85                  90                  95

Asn Ala Gly Phe Ile Ala Leu Asn Ile Trp Asp Arg Phe Asp Val Phe
            100                 105                 110

Cys Thr Leu Gly Ala Ser Asn Gly Tyr Ile Arg Gly Asn Ser Thr Ala
        115                 120                 125

Phe Asn Leu Val Gly Leu Phe Gly Val Lys Gly Thr Thr Val Asn Ala
    130                 135                 140

Asn Glu Leu Pro Asn Val Ser Leu Ser Asn Gly Val Val Glu Leu Tyr
145                 150                 155                 160

Thr Asp Thr Ser Phe Ser Trp Ser Val Gly Ala Arg Gly Ala Leu Trp
                165                 170                 175

Glu Cys Gly Cys Ala Thr Leu Gly Ala Glu Phe Gln Tyr Ala Gln Ser
            180                 185                 190

Lys Pro Lys Val Glu Glu Leu Asn Val Ile Cys Asn Val Ser Gln Phe
        195                 200                 205

Ser Val Asn Lys Pro Lys Gly Tyr Lys Gly Val Ala Phe Pro Leu Pro
    210                 215                 220

Thr Asp Ala Gly Val Ala Thr Ala Thr Gly Thr Lys Ser Ala Thr Ile
225                 230                 235                 240

Asn Tyr His Glu Trp Gln Val Gly Ala Ser Leu Ser Tyr Arg Leu Asn
                245                 250                 255
```

```
Ser Leu Val Pro Tyr Ile Gly Val Gln Trp Ser Arg Ala Thr Phe Asp
            260                 265                 270

Ala Asp Asn Ile Arg Ile Ala Gln Pro Lys Leu Pro Thr Ala Val Leu
        275                 280                 285

Asn Leu Thr Ala Trp Asn Pro Ser Leu Leu Gly Asn Ala Thr Ala Leu
    290                 295                 300

Ser Thr Thr Asp Ser Phe Ser Asp Phe Met Gln Ile Val Ser Cys Gln
305                 310                 315                 320

Ile Asn Lys Phe Lys Ser Arg Lys Ala Cys Gly Val Thr Val Gly Ala
                325                 330                 335

Thr Leu Val Asp Ala Asp Lys Trp Ser Leu Thr Ala Glu Ala Arg Leu
            340                 345                 350

Ile Asn Glu Arg Ala Ala His Val Ser Gly Gln Phe Arg Phe
        355                 360                 365


<210> SEQ ID NO 55
<211> LENGTH: 435
<212> TYPE: DNA
<213> ORGANISM: Legionella pneumophila

<400> SEQUENCE: 55

gattgggcaa agataggcgt agttgattta caaaaaatca tgcaaacctc aaatcaaatg      60

aaggaaatcc aacagaagtt ggaaaaagaa tttaagcctc gtcgagacaa gcttgtcgca     120

atggaagcaa gcttgaaaag cgacatggaa aaattcaagc gtgatagtgc tataatgagc     180

gcgagccaaa agaaagaatt ggaaaagaaa attgttgcgt cacaacaaca gtttgaacgt     240

gatggacaac aatatcagca agaattgagc acggctcaca atgaagctat ggaaggtctg     300

tataataagg ttcgtactgc cattaccaaa attgccaagg atgagaagta cgatattatt     360

gttcagaaag atgcagcgcc cttcagcagc gaatctcttg atgtaacaga taaagttatt     420

aaagcaatta attaa                                                      435


<210> SEQ ID NO 56
<211> LENGTH: 144
<212> TYPE: PRT
<213> ORGANISM: Legionella pneumophila

<400> SEQUENCE: 56

Asp Trp Ala Lys Ile Gly Val Val Asp Leu Gln Lys Ile Met Gln Thr
1               5                   10                  15

Ser Asn Gln Met Lys Glu Ile Gln Gln Lys Leu Glu Lys Glu Phe Lys
            20                  25                  30

Pro Arg Arg Asp Lys Leu Val Ala Met Glu Ala Ser Leu Lys Ser Asp
        35                  40                  45

Met Glu Lys Phe Lys Arg Asp Ser Ala Ile Met Ser Ala Ser Gln Lys
    50                  55                  60

Lys Glu Leu Glu Lys Lys Ile Val Ala Ser Gln Gln Gln Phe Glu Arg
65                  70                  75                  80

Asp Gly Gln Gln Tyr Gln Gln Glu Leu Ser Thr Ala His Asn Glu Ala
                85                  90                  95

Met Glu Gly Leu Tyr Asn Lys Val Arg Thr Ala Ile Thr Lys Ile Ala
            100                 105                 110
```

-continued

```
Lys Asp Glu Lys Tyr Asp Ile Ile Val Gln Lys Asp Ala Ala Pro Phe
        115                 120                 125

Ser Ser Glu Ser Leu Asp Val Thr Asp Lys Val Ile Lys Ala Ile Asn
    130                 135                 140
```

METHOD FOR DIAGNOSING *PROPIONIBACTERIUM* BACTERIAL INFECTIONS

CROSS-REFERENCE TO RELATED APPLICATIONS

This non-provisional U.S. patent application claims the benefit under 35 U.S.C. §119(e) of U.S. Provisional Patent Application No. 61/559,959, filed on Nov. 15, 2011 and also claims the benefit of European Patent Application No. 11306495.0, filed on Nov. 15, 2011, both of which are incorporated herein by reference in their entireties.

INCORPORATION OF SEQUENCE LISTING

A computer readable form of the Sequence Listing is provided herein, contained in the file named "BET12P3013SeqList.txt", which is 141,218 bytes (measured in operating system MS-Windows), created on Nov. 14, 2012, and incorporated herein by reference in its entirety. This Sequence Listing consists of SEQ ID NO: 1-56.

FIELD OF THE INVENTION

The present invention relates to a method of diagnosis of infections with *Propionibacterium* bacteria. More particularly, the invention concerns an in vitro method for determining if an individual is infected by a bacterium of the *Propionibacterium* genus comprising: (i) detecting antibodies directed against at least one protein of sequence SEQ ID NO: 2, SEQ ID NO: 4, SEQ ID NO: 6 or SEQ ID NO: 8, in a biological sample of the individual, and (ii) deducing therefrom that the individual is infected by a bacterium of the *Propionibacterium* genus. The invention further concerns the kit for diagnosing of such an infection.

TECHNICAL BACKGROUND

*Propionibacterium* spp. are part of the normal skin flora and often considered non pathogenic. Most published reports about *Propionibacterium* spp. have involved acne vulgaris and healthy persons (Gehse et al. (1983) Arch. Dermatol. Res. 275(2): 100-104). However, they may cause significant infections, particularly after implantation of a foreign body, such as a prosthetic valve, intraocular lense, ventriculoperitoneal shunt, or orthopedic implant (Jakab et al. (1996) Yale J. Biol. Med. 69(6): 477-482). In particular, Sperling et al. reported that *Propionibacterium* spp. account for 16% of prosthetic shoulder infections (Sperling et al. (2001) Clin. Orthop. Relat. Res. 382: 206-216). Franta et al. reported that among 31/282 patients (11%) with unsatisfactory shoulder arthroplasties, positive intraoperative cultures were found in 23 at the time of revision surgery, with the most common organisms isolated being coagulase-negative *Staphylococcus* spp., followed by *P. acnes* (Franta at al. (2007) J. Shoulder Elbow Surg. 16: 555-562). Indeed, *P. acnes* is emerging as an important pathogen in orthopedic implant infections (Brook et al. (1991) Rev. Infect. Dis. 13:168-172; Lutz et al., (2005) Eur. J. Clin. Microbiol. Infect. Dis. 24: 739-744) with persistent pain reported as the major symptom. *P. acnes* is a Gram-positive bacterium, developing in anaerobic conditions. This bacterium belongs to the natural human flora, commensale of the skin, the conjunctive tissue, the outer ear, the oral cavity, the high respiratory tractus and occasionally, the intestine and the vagina. *P acnes* is in particular associated with the inflammatory process in the acneic lesions. This bacterium is also at the origin of post-operative, in particular in the event of presence of implant, potentially severe infections. This bacterium was associated with other aerobic or anaerobic bacteria with dental infections, parodontites, conjunctivites, endophtalmies, cerebral abscesses, empyemes, lung infections, peritonites, osteomyelitis, septic arthritis and endocarditis in particular on prosthesis, and meningitidis on shunts. Development of prosthetic infections begins with colonization of the foreign material, followed by a complex metamorphosis by the microorganisms with resultant biofilm formation. When bacteria grew in matrix enclosed community, they became recalcitrant to antibiotic therapy and insensitive to host defense mechanisms because of some changes in their cellular characteristics. These infections generally occur (70% of the cases) among diabetes patients introducing an immunodepression, cancer patients having undergone a surgical operation or carrying prosthetic material or catheter.

It is estimated that 2, 8 to 12% of the osteo-articular infections result from infections of prosthesis from hip, knee, shoulder (Brook et al. (1991) Rev. Infect. Dis. 13:168-172). Another study showed that a third of arthritis with *P. acnes* might be due to infections on prosthesis (Brook et al. (1993) Am. J. Med. 94:21-28). The mechanisms of contamination of the operational wound are probably contaminations by the cutaneous flora of the patient, or an airborne contamination (patient or surgical team). It could be related to a hypothetical persistence on surfaces. Insufficiency of the treatment of air in intervention room has been shown as a factor of infection of the operational site in orthopedy. (Berthelot et al. (2006) Infect. Control. Hosp. Epidemiol. 27:987-990).

Clinical symptoms are rarely sufficient to ascertain the infection. In the vast majority of cases, patients are paucisymtomatic. The gold standard for diagnosing prosthesis infections remains bacteriological analysis, which involved isolation and culture of the infecting bacteria at the site of infection, from relevant samples. Bacteriological analysis is generally considered as significant if at least 2 samples taken during the surgery are positive for *P. acnes*. Ultrasound-guided needle aspiration or image-guided core-needle biopsy can also be carried.

Several drawbacks are however associated to bacteriological analysis. The culture is slow and difficult under anaerobic conditions, often requiring 48 hours before the appearance of the colonies. Thus, it is advised to preserve the cultures during 5 days, sometimes the culture can last 15 to 20 days. Other anaerobic bacteria are often found during the cultures. Indeed, the specificity is often insufficient, since contaminant microorganisms may be isolated, rending the diagnosis of *P. acnes* infections more difficult. The difficulty of diagnosis in the case of plurimicrobial infections lies in the fact that it is necessary to resort to various selective mediums. In addition, *P. acnes* is a common contaminant of hemocultures.

According to various studies (Brook et al. (1991) Rev. Infect. Dis. 13:168-172; Lutz et al. (2005) Eur. J. Clin. Microbiol. Infect. Dis. 24: 739-744), the contamination cases can go from 17 to 88%, which increases the risk of appearance of false-positive results. Thus in addition to clinical data, the number of positive cultures as well as the results of the direct examination of the patient must be taken into account for the diagnosis of *P. acnes* infection. The probability of infection increases with the number of positive samples.

There are currently no other methods for establishing the diagnosis of *P. acnes* prosthesis infection. Thus the object of this invention proposes an alternative technique for the diagnosis of the *P. acnes* infections. A serological approach based on the antibodies of anti-*P. acnes* could overcome the drawbacks associated to bacteriological analysis.

SUMMARY OF THE INVENTION

The present invention arises from the unexpected identification, by the inventors, that the proteins 26C4, 26F5, 15C2, 26D6 of *P. acnes* (represented respectively by SEQ ID NO: 2, SEQ ID NO: 4, SEQ ID NO: 6 or SEQ ID NO: 8) provide for efficient detection of *Propionibacterium* genus antibodies in biological samples.

Thus, the present invention relates to a method, in particular an in vitro method, for determining if an individual is infected by a bacterium of the *Propionibacterium* genus, preferably, selected from the group consisting of *P. acnes, P. avidum, P. granulosum* and *P. propionicum* comprising:

- detecting antibodies directed against at least one protein of sequence SEQ ID NO: 2, SEQ ID NO: 4, SEQ ID NO: 6 or SEQ ID NO: 8, in a biological sample of the individual, and
- deducing therefrom that the individual is infected by a bacterium of the *Propionibacterium* genus, preferably selected from the group consisting of *P. acnes, P. avidum, P. granulosum* and *P. propionicum*

According to said method, when antibodies directed against at least one protein of sequence SEQ ID NO: 2, SEQ ID NO: 4, SEQ ID NO: 6 or SEQ ID NO: 8 are detected in a biological sample of an individual, said individual is infected by a bacterium of the *Propionibacterium* genus. Inversely, if no antibody directed against at least one protein of sequence SEQ ID NO: 2, SEQ ID NO: 4, SEQ ID NO: 6 or SEQ ID NO: 8 is detected in a biological sample of an individual, said individual is not infected by a bacterium of the *Propionibacterium* genus.

Consequently and according to said method, when an individual is infected by a bacterium of the *Propionibacterium* genus, antibodies directed against a protein comprising a sequence. SEQ ID NO: 2 may be detected in a biological sample of said individual. Typically, detection of antibodies directed against a protein comprising sequence SEQ ID NO: 2 and antibodies directed against a protein comprising sequence SEQ ID NO: 4 or detection of antibodies directed against a protein comprising sequence SEQ ID NO: 2 and antibodies directed against a protein comprising sequence SEQ ID NO: 6, or detection of antibodies directed against a protein comprising sequence SEQ ID NO: 2 and antibodies directed against a protein comprising sequence SEQ ID NO: 8 or detection of antibodies directed against a protein comprising sequence SEQ ID NO: 4 and antibodies directed against a protein comprising sequence SEQ ID NO: 6 or detection of antibodies directed against a protein comprising sequence SEQ ID NO: 4 and antibodies directed against a protein comprising sequence SEQ ID NO: 8 or detection of antibodies directed against a protein comprising sequence SEQ ID NO: 6 and antibodies directed against a protein comprising sequence SEQ ID NO: 8 may be sufficient to deduce that an individual is infected by a bacterium of the *Propionibacterium* genus. Detection of antibodies directed against a protein comprising sequence SEQ ID NO: 2 and of antibodies directed against a protein comprising sequence SEQ ID NO: 4 and of antibodies directed against a protein comprising sequence SEQ ID NO: 6 or detection of antibodies directed against a protein comprising sequence SEQ ID NO: 4 and of antibodies directed against a protein comprising sequence SEQ ID NO: 6 and of antibodies directed against a protein comprising sequence SEQ ID NO: 8 or detection of antibodies directed against a protein comprising sequence SEQ ID NO: 2 and of antibodies directed against a protein comprising sequence SEQ ID NO: 6 and of antibodies directed against a protein comprising sequence SEQ ID NO: 8 may be sufficient to deduce that an individual is infected by a bacterium of the *Propionibacterium* genus. Similarly, detection of antibodies directed against a protein comprising sequence SEQ ID NO: 2 and of antibodies directed against a protein comprising sequence SEQ ID NO: 4 and of antibodies directed against a protein comprising sequence SEQ ID NO: 6 and of antibodies directed against a protein comprising sequence SEQ ID NO: 8 may be sufficient to deduce that an individual is infected by a bacterium of the *Propionibacterium* genus.

Preferably, said detection of antibodies directed against at least one protein of sequence SEQ ID NO: 2, SEQ ID NO: 4, SEQ ID NO: 6 or SEQ ID NO: 8, in a biological sample of the individual comprises contacting the biological sample with:

(i) at least one protein of sequence SEQ ID NO: 2, SEQ ID NO: 4, SEQ ID NO: 6 or SEQ ID NO: 8; and/or, (ii) at least one homologous protein comprising or consisting of a sequence having at least 90% identity with a sequence SEQ ID NO: 2, SEQ ID NO: 4, SEQ ID NO: 6 or SEQ ID NO: 8; and/or, (iii) at least one fragment of said protein defined in (i) or said homologous protein defined in (ii);

provided the homologous protein defined in (ii) or the fragment defined in (iii) can be bound by at least one antibody directed against a protein of sequence SEQ ID NO: 2, SEQ ID NO: 4, SEQ ID NO: 6 or SEQ ID NO: 8.

Preferably said fragment defined in (iii) may comprise 4 to 200 contiguous amino acids of said protein defined in (i) and/or of said homologous protein defined in (ii).

As appropriate, a protein sequence comprising or consisting of a sequence SEQ ID NO: 2, or an homologous protein comprising or consisting of a sequence having at least 90% identity with a sequence SEQ ID NO: 2 or a fragment of said protein or said homologous protein may be used for detection of antibodies directed against protein comprising a sequence SEQ ID NO: 2. Said method is applicable mutatis mutandis to SEQ ID NO: 4, SEQ ID NO: 6 and SEQ ID NO: 8.

The present invention also relates to the use of:

(i) at least one protein of sequence SEQ ID NO: 2, SEQ ID NO: 4, SEQ ID NO: 6 or SEQ ID NO: 8; and/or (ii) at least one homologous protein comprising a sequence having at least 90% identity with a sequence SEQ ID NO: 2, SEQ ID NO: 4, SEQ ID NO: 6 or SEQ ID NO: 8; and/or (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8, for in vitro diagnosis of infection with a bacterium of the *Propionibacterium* genus.

Preferably said fragment defined in (iii) may comprise 4 to 200 contiguous amino acids of said protein defined in (i) and/or of said homologous protein defined in (ii).

The present invention also relates to a kit for diagnosing an infection by a bacterium of the *Propionibacterium* genus, preferably, selected from the group consisting of *P. acnes, P.*

*avidum, P. granulosum* and *P. propionicum*, comprising antigens which can be bound by antibodies directed against at least two proteins selected from the group consisting of SEQ ID NO: 2, SEQ ID NO: 4, SEQ ID NO: 6 and SEQ ID NO: 8 wherein said antigens are:

(i) at least one protein of sequence SEQ ID NO: 2, SEQ ID NO: 4, SEQ ID NO: 6 or SEQ ID NO: 8; and/or (ii) at least one homologous protein comprising or consisting of a sequence having at least 90% identity with a sequence SEQ ID NO: 2, SEQ ID NO: 4, SEQ ID NO: 6 or SEQ ID NO: 8; and/or (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8

Preferably said fragment defined in (iii) may comprise 4 to 200 contiguous amino acids of said protein defined in (i) and/or of said homologous protein defined in (ii).

The invention also provides a kit for further diagnosing if an individual is infected by a *Staphylococcus* bacterium. Indeed, preferably, said kit further comprises:

(i) at least one protein of sequence SEQ ID NO: 32, SEQ ID NO: 34, SEQ ID NO: 36; SEQ ID NO: 38; SEQ ID NO: 40; SEQ ID NO: 42 or SEQ ID NO: 44 and/or, (ii) at least one homologous protein comprising a sequence having at least 90% identity with a sequence SEQ ID NO: 32, SEQ ID NO: 34, SEQ ID NO: 36; SEQ ID NO: 38; SEQ ID NO: 40; SEQ ID NO: 42 or SEQ ID NO: 44 and/or, (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 32, SEQ ID NO: 34, SEQ ID NO: 36; SEQ ID NO: 38; SEQ ID NO: 40; SEQ ID NO: 42 and SEQ ID NO: 44.

According to said invention, the proteins 2B6, 7B3, 5G1, 2D6B1, 4A1, 9F2 and 6H4 of *Staphylococcus* (represented respectively by SEQ ID NO: 32, SEQ ID NO: 34, SEQ ID NO: 36; SEQ ID NO: 38; SEQ ID NO: 40; SEQ ID NO: 42, and SEQ ID NO: 44.) provide for efficient detection of anti-*Staphylococci*, antibodies in biological samples.

The invention also provides a kit for further diagnosing if an individual is infected by a bacterium selected from the group consisting *Streptococcus, Enterococcus* and *Peptostreptococcus* genera. Indeed, preferably also, said kit further comprises:

(i) at least one protein of sequence SEQ ID NO: 46, SEQ ID NO: 48, SEQ ID NO: 50 or SEQ ID NO: 52; and/or, (ii) at least one homologous protein comprising a sequence having at least 90% identity with a sequence SEQ ID NO: 46, SEQ ID NO: 48, SEQ ID NO: 50 or SEQ ID NO: 52; and/or, (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 46, SEQ ID NO: 48, SEQ ID NO: 50 or SEQ ID NO: 52.

According to said invention, the proteins 25D6, 25D3, 25H3, and 25C6 of *S. agalactiae* (represented respectively by SEQ ID NO: 46, SEQ ID NO: 48, SEQ ID NO: 50 and SEQ ID NO: 52) provide for efficient detection of anti-*streptococci*, anti-*Enterococci* and anti-*Peptostreptococcus* spp. antibodies in biological samples.

The invention also provides a kit for further diagnosing if an individual is infected by a gram negative bacterium. Indeed, preferably also, said kit further comprises:

(i) at least one protein of sequence SEQ ID NO: 54, or SEQ ID NO: 56; and/or, (ii) at least one homologous protein comprising a sequence having at least 90% identity with a sequence SEQ ID NO: 54, or SEQ ID NO: 56; and/or, (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 54, or SEQ ID NO: 56.

According to said invention, the proteins 14D3 of *Chlamydia pneumoniae* and 2E1 of *Legionella pneumophila* (represented respectively by SEQ ID NO: 54, and SEQ ID NO: 56) provide for efficient detection of anti-gram negative bacteria antibodies in biological samples.

The present invention also relates to an in vitro method, for determining if an individual is infected by a bacterium of the *Propionibacterium* genus, preferably, selected from the group consisting of *P. acnes, P. avidum, P. granulosum* and *P. propionicum*, comprising:

- contacting at least one capture ligand specific of at least one protein of sequence SEQ ID NO: 2, SEQ ID NO: 4, SEQ ID NO: 6 or SEQ ID NO: 8, with a biological sample of the individual;
- determining if said protein is bound to the specific capture ligands;
- deducing therefrom that the individual is infected by a bacterium of the *Propionibacterium* genus, preferably, selected from the group consisting of *P. acnes, P. avidum, P. granulosum* and *P. propionicum.*

Said in vitro method, for determining if an individual is infected by a bacterium of the *Propionibacterium* genus may further comprises:

- comparing the amount of bound capture ligands from the biological sample to an amount of bound capture ligands from one or more control sample(s), and
- determining whether or not the individual is infected by said bacteria of the *Propionibacterium* genus based upon said comparison.

The present invention also relates to an in vitro diagnostic method for determining if an individual is infected by bacteria of the *Propionibacterium* genus, comprising:

- contacting a biological sample of the individual with at least one purified or synthetic protein selected from the group consisting of:
  - (i) at least one protein of sequence SEQ ID NO: 2, SEQ ID NO: 4, SEQ ID NO: 6 or SEQ ID NO: 8; and/or
  - (ii) at least one homologous protein comprising a sequence having at least 90% identity with a sequence SEQ ID NO: 2, SEQ ID NO: 4, SEQ ID NO: 6 or SEQ ID NO: 8; and/or
  - (iii) at least one fragment of protein defined in (i) or homologous protein defined in (ii);
  - provided the homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8, and
- determining the amount of antibodies present in the biological sample that are bound to said at least one protein, preferably, comparing the amount of bound antibodies from the biological sample to an amount of bound antibodies from one or more control sample(s), and determining whether or not the individual is infected by said bacteria of the *Propionibacterium* genus based upon said comparison.

In an embodiment of the invention, the above-defined method comprises contacting specific capture ligands of at least two proteins comprising a sequence selected from the group consisting of SEQ ID NO: 2, SEQ ID NO: 4, SEQ ID NO: 6 and SEQ ID NO: 8.

The present invention also relates to the use, in particular the in vitro use, of one or more specific capture ligands, in particular an antibody, directed against a protein of sequence SEQ ID NO: 2, SEQ ID NO: 4, SEQ ID NO: 6 or SEQ ID NO: 8 for determining if an individual is infected by a bacterium of the *Propionibacterium* genus, preferably, selected from the group consisting of *P. acnes, P. avidum, P. granulosum* and *P. propionicum*. In other words, the present invention also relates to a method for the in vitro diagnosis of an infection by a bacterium of the *Propionibacterium* genus, preferably, selected from the group consisting of *P. acnes, P. avidum, P. granulosum* and *P. propionicum* in an individual, in whom one detects the presence of at least an antigen of the aforesaid bacterium in a biological sample of the individual using one or more capture ligands of, in particular one or more antibodies, directed against one or more proteins comprising a sequence selected from the group consisting of SEQ ID NO: 2, SEQ ID NO: 4, SEQ ID NO: 6 and SEQ ID NO: 8.

The present invention also relates to an antigenic kit for diagnosing an infection by a bacterium of the *Propionibacterium* genus, preferably, selected from the group consisting of *P. acnes, P. avidum, P. granulosum* and *P. propionicum*, comprising one or more capture ligands, in particular an antibody, directed against a protein of sequence SEQ ID NO: 2, SEQ ID NO: 4, SEQ ID NO: 6 or SEQ ID NO: 8.

DETAILED DESCRIPTION OF THE INVENTION

As intended herein, the expressions "*Propionibacterium*" or "P." such as in *P. acnes, P. avidum, P. granulosum* or *P. propionicum*, relates to a bacterium or to bacteria of the *Propionibacterium* genus. Preferably, the *Propionibacterium* of the invention is a *P. acnes*, a *P. avidum*, a *P. granulosum* or a *P. propionicum.*

As intended herein, the expression 'infected' or 'infection' relates to individuals carrying a bacterium of the *Propionibacterium* genus as defined above. Preferably, the infected individuals present one or more sites wherein multiplication of the bacterium is occurring. Infections by a bacterium of the *Propionibacterium* genus can occur as a consequence of the contact of internal tissues with a foreign material contaminated by a bacterium of the *Propionibacterium* genus, in particular in a hospital setting. Accordingly, as intended herein, the infection is a prosthetic infection. "Prosthetic infection" or "prosthetic material related infection" refers to an infection which arises from the implantation of a prosthetic material in the individual.

Preferably, the infection is a biofilm infection. During infections, bacteria such as of *Propionibacterium* genus, may establish themselves on a surface such as a prosthesis and colonized it by forming a biofilm which may not be accessible to the systemic drug or to the immune system as the bacteria are protected by the biofilm or slime. It has also been described that genes expressed in a biofilm forming bacteria differ from those expressed in the corresponding planktonic bacteria, among which genes involved in producing the polysaccharidic matrix. This modification of genes expression is also responsible of a modification of bacteria characteristics and thus of their antigenicity.

As intended herein, the expression "prosthetic material", "prosthesis" or "implant" refers to a foreign material implanted in an individual such as neurosurgical devices, intracardiac devices such as vascular catheters, prosthetic heart valves, cardiac pacemakers, implantable cardioverter defibrillators, vascular grafts; implants, ear implants such as cochlear implants; nose, breast or throat implants, urological implants, endotracheal or tracheostomy tubes, dialysis catheters, CNS shunts, ocular implants, orthopedic implants or prosthetic joint, notably selected from the group consisting of a knee joint, a shoulder joint and a hip joint.

Accordingly, as intended herein, the method according to the invention is implemented in order to determine if an individual suffers from an infection by a bacterium of the *Propionibacterium* genus, the mentioned infection being selected among an infection on prosthesis (in particular articular prosthesis), an osteo-articular infection, a post-operative infection (in particular during the installation of a foreign material such as a prosthesis), a dental infection, a parodontite, a conjunctivitis, an endophtalmy, a cerebral abscess, an empyema under-dural, a lung infection, a peritonitis, an osteomyelitis, a septic arthritis, an endocarditis (in particular on prosthesis), a meningitis (in particular on shunts).

Preferably, the method according to the invention is specially designated to prosthesis infections but not to local infections such as skin infections. The individual can moreover be an individual diabetic, and/or presenting an immunodepression, and/or suffering of a cancer and/or carrying prosthetic material or catheter. Preferably the individual presenting a prosthetic joint selected from the group consisting of a knee joint, a shoulder joint and a hip joint. According to the invention, such a prosthetic joint may be infected by said a bacterium of the *Propionibacterium* genus.

As intended herein, the expression 'biological sample' includes both the sample as taken and the sample which has been subjected to various treatments after sampling, in particular to render it suitable for the use in the processes and methods according to the invention. The 'biological sample' according to the invention can be of any type liable to contain antibodies. However, it is preferred that the biological sample is selected from the group consisting of blood, serum, plasma, mucosa-associated lymphoid tissue (MALT), cephalorachidian fluid, articular liquid, pleural liquid, saliva, and urine.

The terms "control" or "control sample" refer to any sample appropriate to the detection technique employed and which is representative of healthy or infected individual. A control sample may be a positive control which may typically be a biological sample from an individual who has been diagnosed as being infected by a bacterium of the *Propionibacterium* genus. Alternatively, a positive control sample may be a sample comprising or consisting of an antibody directed against a protein comprising or consisting of a sequence SEQ ID NO: 2, SEQ ID NO: 4, SEQ ID NO: 6 or SEQ ID NO: 8. A negative control sample may typically be a biological sample from a normal individual. The normal individual is typically a healthy individual. A healthy individual is one not suffering from an infection by a bacterium of the *Propionibacterium* genus.

As intended herein, the expression 'determining if an individual is infected by a bacterium of the *Propionibacterium* genus' encompasses establishing a diagnosis or diagnosing an infection by a bacterium of the *Propionibacterium* genus in an individual. It also encompasses following-up of individuals having undergone a surgical operation for implanting, cleaning or replacing the prosthesis. It further encompasses following the evolution of infection by a bacterium of the *Propionibacterium* genus, in particular within the framework of a therapeutic treatment. Accordingly, it is preferred that the individual is under treatment by antibiotics.

Determining if antibodies directed against a protein of sequence SEQ ID NO: 2, SEQ ID NO: 4, SEQ ID NO: 6 or SEQ ID NO: 8, are present in a biological sample of the individual can be carried out by various methods well known to one of skill in the art such as immunoassays. However, determining if antibodies directed against a protein of sequence SEQ ID NO: 2, SEQ ID NO: 4, SEQ ID NO: 6 or SEQ ID NO: 8, are present in a biological sample of the individual comprises:

contacting the biological sample with:

(i) at least one protein of sequence SEQ ID NO: 2, SEQ ID NO: 4, SEQ ID NO: 6 or SEQ ID NO: 8; or (ii) at least one homologous protein comprising a sequence having at least 90% identity with a sequence SEQ ID NO: 2, SEQ ID NO: 4, SEQ ID NO: 6 or SEQ ID NO: 8; or (iii) at least one fragment of said protein of sequence SEQ ID NO: 2, SEQ ID NO: 4, SEQ ID NO: 6 or SEQ ID NO: 8 or of said homologous protein;

provided said homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8;

detecting antibodies, preferably IgG, bound to at least one protein of sequence SEQ ID NO: 2, SEQ ID NO: 4, SEQ ID NO: 6 or SEQ ID NO: 8, to said homologous protein or, to said at least one fragment.

Preferably, determining if an individual is infected by bacteria of the *Propionibacterium* genus comprises:

contacting a biological sample of the individual with (i) at least one protein of sequence SEQ ID NO: 2, SEQ ID NO: 4, SEQ ID NO: 6 or SEQ ID NO: 8; and/or (ii) at least one homologous protein comprising a sequence having at least 90% identity with a sequence SEQ ID NO: 2, SEQ ID NO: 4, SEQ ID NO: 6 or SEQ ID NO: 8; and/or (iii) at least one fragment of protein defined in (i) or homologous protein defined in (ii);

provided the homologous protein defined in (ii) or that the fragment defined in (iii) can be bound by at least one antibody directed against a protein of sequence SEQ ID NO: 2, SEQ ID NO: 4, SEQ ID NO: 6 or SEQ ID NO: 8, and allowing antibodies present in the biological sample to specifically bind to said protein, performing an immunoassay to determine the amount of said antibodies from the biological sample that are bound to said protein, preferably, comparing the amount of said bound antibodies from the biological sample to an amount of bound antibodies from one or more control sample(s), and determining whether or not the individual is infected by said bacteria the *Propionibacterium* genus, based upon said comparison.

Preferably, said fragment defined in (iii) may comprise 4 to 200 contiguous amino acids of said protein defined in (i) and/or of said homologous protein defined in (ii).

The protein comprising or consisting of a sequence SEQ ID NO: 2, SEQ ID NO: 4, SEQ ID NO: 6 or SEQ ID NO: 8; the homologous protein thereto, or the fragments thereof, may be a purified protein or a synthetic protein.

In certain embodiments, the protein of the present invention may be purified. The term "purified," as used herein, is intended to refer to a composition, isolatable from other components, wherein the protein is purified to any degree relative to its naturally-obtainable state. An "isolated protein" or a "purified protein" therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying a protein of the present invention, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

As used herein, "Synthetic protein" refers to a protein that is obtained from a non-natural source, e.g., is man-made. Such proteins may be produced using such methods as chemical synthesis or recombinant DNA technology.

The protein comprising or consisting of a sequence SEQ ID NO: 2, SEQ ID NO: 4, SEQ ID NO: 6 or SEQ ID NO: 8; the homologous protein thereto, or the fragments thereof, can present either as polypeptide chains resulting from the in vivo, ex vivo or in vitro polymerization of amino acids selected from the 20 natural amino acids, or as modified polypeptide chains. As intended herein, in vivo or ex vivo polymerization notably encompasses production by in vitro translation or by chemical synthesis. Where the polypeptide is modified, it can result from the use of non-natural amino acids during the in vivo, ex vivo or in vitro polymerization of the polypeptide chain and from post-polymerisation modifications. The polypeptide can be modified one or several times by identical or different modifications. The modifications can be anywhere in the polypeptide chain, and notably in the peptide backbone, in the amino acid lateral groups, or at the N-terminal or C-terminal extremities of the polypeptide chain. Modification notably encompass acylation, in particular acetylation, palmytoylation, glypiation, prenylation and myristoylation, ADP-ribosylation, amidation, covalant linkage of a lipid, such as phosphatidylinositol, flavin, an heme, or a nucleotide, covalent, or non-covalent cross-linking, cyclisation, disulfide bridge oxidation and reduction, methylation and demethylation, pyroglutamate formation, formylation, gamma-carboxylation, glycosylation, hydroxylation, iodation, phosphorylation, selenoylation, sulfatation, racemisation, addition of amino-acids, such as arginylation, or of polypeptides, such as ubiquitinylation (Proteins structure and molecular properties, 2nd ed., T. E. Creighton, W. H. Freeman and Company, New York (1993) and Wold, F., Posttranslational Protein Modifications Prospects and Prospective customers, pgs 1-12 in Covalent posttranslational modification of proteins, B. C. Johnson, ED., Press Academy, New York (1983); Seifter et al. (1990) Meth. Enzymol. 182: 626-646 and Rattan et al. (1992) Protein Synthesis: Posttranslational Modifications and Aging, Ann. NR. Y. Acad. Sci. 663: 48-62).

Besides, where they are obtained by recombining means, the polypeptide chain comprising or consisting of a sequence selected from the group consisting of SEQ ID NO: 2, SEQ ID NO: 4, SEQ ID NO: 6 and SEQ ID NO: 8, the homologous protein thereto, and the fragments thereof, may also comprise sequences useful for protein purification (so-called purification tags), such as polyhistidine tags, and optionally a sequence enabling the cleavage of these tags, such as protease cleavage sites.

Preferably, the protein of sequence SEQ ID NO: 2, SEQ ID NO: 4, SEQ ID NO: 6 or SEQ ID NO: 8, comprises 350, 400, 500, or 1000 amino-acids at the most. More preferably the proteins comprising a sequence selected from the group consisting of SEQ ID NO: 2, SEQ ID NO: 4, SEQ ID NO: 6 and SEQ ID NO: 8, respectively consist in SEQ ID NO: 2 or SEQ ID NO: 21, SEQ ID NO: 4 or SEQ ID NO: 22, SEQ ID NO: 6 or SEQ ID NO: 23, and SEQ ID NO: 8 or SEQ ID NO: 24. Preferably proteins comprising or consisting of SEQ ID NO: 2, SEQ ID NO: 4, SEQ ID NO: 6 and SEQ ID NO: 8 are respectively encoded by nucleic acids comprising or consisting of SEQ ID NO: 1, SEQ ID NO: 3, SEQ ID NO: 5 and SEQ ID NO: 7.

The percentage of identity according to the invention can be calculated by methods well-known to one of skill in the art. The percentage of identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5. The term "homologous protein" means a protein having a percentage of identity with proteins comprising a sequence SEQ ID NO: 2, SEQ ID NO: 4, SEQ ID NO: 6 or SEQ ID NO: 8 according to the invention.

Preferably, the percentage of identity relates to the number of identical amino-acids obtained for an optimal paired alignment (i.e. the alignment maximizing the number of identical amino-acids) of the sequence of a protein homologous to a sequence SEQ ID NO: 2, SEQ ID NO: 4, SEQ ID NO: 6 or SEQ ID NO: 8, divided by the total number of amino-acids in SEQ ID NO: 2, SEQ ID NO: 4, SEQ ID NO: 6 or SEQ ID NO: 8. Alignment can be performed manually or using computer programs such as the EMBOSS-Needle program (Needleman and Wunsch (1970) J. Mol. Biol. 48:443-453). Preferably, the percentage of identity according to the invention is at least 90%, more preferably at least 95%, and even more preferably from at least 97%. Preferably, the fragment contains an epitope. The smaller fragment that may be recognized by an antibody may have 4 to 5 contiguous amino acids. Consequently, according to the invention a 'fragment' may be of 4, 5, 6, 7, 8, 9, 10, 11, 12, 13, 14, 15, 16, 17, 18, 19, 20 contiguous amino acids. Preferably, said fragment may comprise 22 to 200 contiguous amino acids, more preferably 25 to 150 contiguous amino acids, and more preferably 30 to 100 contiguous amino acids. Preferably also, the 'fragment' may comprise 35 to 80 contiguous amino acids, more preferably 40 to 75 contiguous amino acids at the most, and most preferably 45 to 70 contiguous amino acids at the most. Preferably also, the 'fragment' according to the invention consists of a portion of SEQ ID NO: SEQ ID NO: 2, SEQ ID NO: 4, SEQ ID NO: 6 or SEQ ID NO: 8, or of a portion of sequences presenting at least 85%, more preferably at least 90%, and more preferably from at least 95% of SEQ ID NO: 2, SEQ ID NO: 4, SEQ ID NO: 6 and SEQ ID NO: 8 at the most.

As intended herein, the homologous protein as defined above and the at least one fragment as defined above can be bound by at least one antibody directed against a protein of sequence SEQ ID NO: 2, SEQ ID NO: 4, SEQ ID NO: 6 or SEQ ID NO: 8. In other words, the homologous protein as defined above and the at least one fragment as defined above comprises at least one of the epitopes of a protein consisting of SEQ ID NO: 2, SEQ ID NO: 4, SEQ ID NO: 6 and SEQ ID NO: 8. Accordingly, the homologous protein as defined above and the at least one fragment as defined above comprise at least one of the epitopes of a protein comprising SEQ ID NO: 2, SEQ ID NO: 4, SEQ ID NO: 6 or SEQ ID NO: 8. Accordingly, the homologous protein as defined above and the at least one fragment as defined above should preferably be such that they provide at least 70%, more preferably at least 80% and most preferably at least 90%, of the sensitivity provided by the protein comprising or consisting of SEQ ID NO: 2, SEQ ID NO: 4, SEQ ID NO: 6 or SEQ ID NO: 8, measured in the same conditions.

As intended herein, the term 'sensitivity' is defined as the percentage of individuals infected by a bacterium of the *Propionibacterium* genus, which biological samples, such as serum samples, are determined to contain antibodies directed against a protein comprising or consisting of a sequence SEQ ID NO: 2, SEQ ID NO: 4, SEQ ID NO: 6 or SEQ ID NO: 8, detectable according to the invention. The determining of the sensitivity provided by an antigen can be carried out according to various methods well-known to one of skill in the art and notably as illustrated in the following Example 1. Preferably, the antibodies detected in the biological samples according to the invention are IgG.

In addition, as that will appear clearly to one of skill in the art, 'an antibody directed against at least one protein of sequence SEQ ID NO: 2, SEQ ID NO: 4, SEQ ID NO: 6 or SEQ ID NO: 8 means any antibody of the individual able to recognize a protein consisting of a sequence SEQ ID NO: 2, SEQ ID NO: 4, SEQ ID NO: 6 or SEQ ID NO: 8, i.e. a specific antibody of this protein, but which can also recognize:

- a larger protein of sequence SEQ ID NO: 2, SEQ ID NO: 4, SEQ ID NO: 6 or SEQ ID NO: 8; or a homologous protein comprising or consisting of a sequence having at least 90% identity with a sequence SEQ ID NO: 2, SEQ ID NO: 4, SEQ ID NO: 6 or SEQ ID NO: 8;
- a fragment of at least 4 contiguous amino acids, preferably at least 5 contiguous amino acids, preferably also, 6 to 200 contiguous amino acids of homologous protein or of a protein comprising or consisting of a sequence SEQ ID NO: 2, SEQ ID NO: 4, SEQ ID NO: 6 or SEQ ID NO: 8. Preferably said fragment defined in (iii) may comprise 4 to 200 contiguous amino acids of said protein defined in (i) and/or of said homologous protein defined in (ii).

Providing the detection of antibodies directed against a protein of sequence SEQ ID NO: 2, SEQ ID NO: 4, SEQ ID NO: 6 or SEQ ID NO: 8, in the biological samples, or the antigen detection of a bacterium of the *Propionibacterium* genus, preferably selected from the group consisting of *P. acnes, P. avidum, P. granulosum* and *P. propionicum* using a ligand of capture, such as an antibody, directed, preferably specifically directed, against a protein of sequence SEQ ID NO: 2, SEQ ID NO: 4, SEQ ID NO: 6 or SEQ ID NO: 8, can be easily implemented by one of skill in the art.

Being the detection of antibody directed against a protein comprising or consisting of a sequence SEQ ID NO: 2, SEQ ID NO: 4, SEQ ID NO: 6 or SEQ ID NO: 8, in the biological samples, it can be carried out with the assistance (i) of at least one protein of sequence SEQ ID NO: 2, SEQ ID NO: 4, SEQ ID NO: 6 or SEQ ID NO: 8; or (ii) of at least one homologous protein comprising or consisting of a sequence having at least 90% identity with a sequence SEQ ID NO: 2, SEQ ID NO: 4, SEQ ID NO: 6 or SEQ ID NO: 8; or (iii) of at least one fragment of protein defined in (i) or homologous protein defined in (ii), preferably, the fragment comprising at least 4 contiguous amino acids of said protein defined in (i) or homologous protein defined in (ii).

Preferably said fragment defined in (iii) may comprise 5 to 200 contiguous amino acids of said protein defined in (i) and/or of said homologous protein defined in (ii).

In addition, as that will appear clearly to one of skill in the art, 'antibodies directed against at least two proteins selected from the group consisting of SEQ ID NO: 2, SEQ ID NO: 4, SEQ ID NO: 6 and SEQ ID NO: 8 means antibodies of the individual able to recognize a first sequence SEQ ID NO: 2, SEQ ID NO: 4, SEQ ID NO: 6 or SEQ ID NO: 8 and antibodies of the individual able to recognize a second sequence SEQ ID NO: 2, SEQ ID NO: 4, SEQ ID NO: 6 or SEQ ID NO: 8.

As used herein, the term "immunoassay" refers to a test that uses the binding of antibodies to antigens present in a biological sample to identify and measure certain substances or that uses the binding of antibodies present in a biological sample to an antigen to determine if an individual is immunized against said antigen. Immunoassays are used to diagnose disease, and test results can provide information about a disease that may help in planning treatment (for example, when an individual is infected by a bacterium). An immunoassay takes advantage of the specific binding of an antibody to its antigen. Monoclonal antibodies are often used as they usually bind only to one site of a particular molecule, and therefore provide a more specific and accurate test, which is less easily confused by the presence of other molecules. The antibodies used must have a high affinity for the antigen of interest, because a very high proportion of the antigen must bind to the antibody in order to ensure that the assay has adequate sensitivity. Inversely, the antigen used must be very immunoreactive in order to provide the detection of antibodies present in the biological sample to be analyzed and to ensure that the assay has adequate sensitivity and specificity.

Any type of immunoassay format may be used, including, without limitation, enzyme immunoassays (EIA, ELISA), radioimmunoassay (RIA), fluoroimmunoassay (FIA), chemiluminescent immunoassay (CLIA), counting immunoassay (CIA), immunohistochemistry (IHC), LUMINEX® bead-based assay, agglutination, nephelometry, turbidimetry or Western Blot. These and other types of immunoassays are well-known and are described in the literature, for example, in Immunochemistry, Van Oss and Van Regenmortel (Eds), CRC Press, 1994; The Immunoassay Handbook, D. Wild (Ed.), Elsevier Ltd., 2005; and the references disclosed therein.

The preferred assay format for the present invention is the LUMINEX® bead-based assay format. LUMINEX® bead-based assay is a highly sensitive technique for detecting and measuring antigens or antibodies in a solution in which the solution is run over fluorescent microspheres to which immobilized antibodies specific to the substance have been coupled, and if the substance is present, it will bind to the antibody coupled, and its presence is verified and visualized with an application of antibodies that have been tagged or labeled so as to permit detection. LUMINEX® bead-based assays combine the high specificity of antibodies with the high sensitivity of enzyme assays by using antibodies or antigens coupled to R-phycoerythrin orand are very useful tools both for determining antibody concentrations (antibody titer) in sera as well as for detecting the presence of antigen.

There are many different types of LUMINEX® bead-based assays; the most common types include indirect (antibody capture) immunoassay, capture sandwich immunoassay, competitive immunoassay for antigen-coupled microspheres or antibody-coupled microspheres, and combined capture sandwich/competitive immunoassay Performing a LUMINEX® bead-based assay involves at least one antibody with specificity for a particular antigen. The sample with an unknown amount of antigen is coupled on fluorescent microspheres (polystyrene microspheres) either non-specifically (via adsorption to the surface or with addition of N-hydroxysulfosuccinimide and 1-ethyl-3-(3-dimethylaminopropyl) carbodiimide) or specifically (via capture by another antibody specific to the same antigen, in a "sandwich" assay). After the antigen is coupled the detection antibody is added, forming a complex with the antigen. The detection antibody can be covalently linked to an enzyme, or can itself be detected by a secondary antibody which is linked to R-phycoerythrin. Between each step the plate typically is washed with a mild detergent solution to remove any proteins or antibodies that are not specifically bound. After the final wash step the plate is read with a detectable fluorescence to produce a visible signal, which indicates the quantity of antigen in the sample.

In a typical LUMINEX® Lumine bead-based assay, an antibody ("capture antibody") is coupled onto microspheres. Monoclonal antibodies are preferred as capture antibodies due to their greater specificity, but polyclonal antibodies also may be used. When the test sample is added to the microspheres, the antibody on the microspheres will bind the target antigen from the sample, and retain it. When a second antibody ("detection antibody") or antibody pair is added in the next step, it also binds to the target antigen (already bound to the monoclonal antibody on the microspheres), thereby forming an antigen 'sandwich' between the two different antibodies.

This binding reaction can then be measured by fluorescent dye attached to the detection antibody. The label generates a fluorescent signal proportional to the amount of target antigen present in the original sample coupled to the microspheres. the level of fluorescence is measured with the LUMINEX® 100/200, FLEXMAP 3D® or MAGPIX® instrument using LUMINEX® IS or XPONENT software.

Further preferably, in the above-defined serologic method, detecting antibodies can be carried out with specific detecting ligands of the antibodies.

As intended herein, a "ligand" is a compound liable to specifically bind to a target, such as an antibody or an antigen. The ligand can be of any type but preferably, it is an antibody, an aptamer, or a peptide obtained by phage display. To determine whether antibodies or antigens are fixed by a ligand of capture one can use a ligand detection, which can be specific either antibodies or antigens fixed, or of the ligands of capture.

The methods calling upon capture ligands and ligands of detection are well-known to one of skill of the art, and can be performed according to various well-known formats, solid or homogeneous phase, one or two stages, using a method sandwich or by competition. Preferably, the ligand of capture is immobilized on a solid phase, such as the walls of a well of a plate of microtitration or paramagnetic balls.

As intended herein, an "antigen" relates to any substance that elicits an immune response in an animal, including a human, upon administration. Antigen refers also to a substance which is a ligand of an antibody to which it binds. The term "epitope" as used herein means the portion of the antigen which interacts with an antibody. When the antigen is a protein, said portion may be a specific amino acid sequence, a modified amino acid sequence, or a protein secondary or tertiary structure.

An "antibody" as intended herein relates to antibodies belonging to any species, such as human, mouse, rat, rabbit, goat, or *camelidae* species. The antibody can also be a chimeric antibody, i.e. an antibody which comprises parts originating from different species. Preferred chimeric antibodies are so-called "humanized" antibodies, wherein the constant parts (CH and CL) are of human origin and the variable parts (VH and VL) are of another species, such as mouse for instance. The antibody of the invention can be produced by any method known the man skilled in the art, such as by animal immunization, or by recombinant or synthetic methods for instance. Besides, an "antibody" according to the invention also encompasses antibody fragments which comprise at least one of the paratopes of said antibody, such as Fab, F(ab')2, scFv fragments as well as *camelidae* single-chain antibodies. The antibody of the invention can be a polyclonal antibody, in particular a monospecific polyclonal antibody, or a monoclonal antibody.

"Aptamers" are well-known by the one skilled in the art. Aptamers are compounds of a nucleotide, in particular a ribonucleotide or desoxyribonucleotide, or a peptide nature able to bind specifically to a target, in particular a protein target. The aptamers of a nucleotide nature and the production thereof are described, in particular, by Ellington et al. (1990) Nature 346:818-822 and Bock et al. (1992) Nature 355:564-566. The aptamers of a peptide nature and the production thereof are described, in particular, by Hoppe-Seyler et al. (2000) J. Mol. Med. 78:426-430.

"Phage display" denotes a technique for selecting polypeptide ligands expressed on the capsid of a bacteriophage and encoded by a nucleic sequence inserted into the capsid encoding gene. This method is well known by the one skilled in the art and is described, in particular, by Scott and Smith (1990) Science 249:386-390, and Marks et al. (1991) J. Mol. Biol. 222:581-597. Preferably, the polypeptide obtainable by phage display is an scFv-type polypeptide (single-chain variable fragment). This technique is described, in particular, by Winter et al. (1994) Annu. Rev. Immunol. 12:433-455.

The term "specific", when it refers to recognition of a ligand or binding of a ligand to a first target, such as an antigen or an antibody, means that the ligand interacts with the first target without interacting substantially with another target which does not structurally resemble the first target, for example, the ligand. Preferably the antibody directed against a polypeptide of sequence SEQ ID NO: 2, SEQ ID NO: 4, SEQ ID NO: 6 and SEQ ID NO: 8 does not bind to a polypeptide having less than 85%, preferably 90%, sequence identity with SEQ ID NO: 2, SEQ ID NO: 4, SEQ ID NO: 6 and SEQ ID NO: 8, as appropriate.

As defined herein, the term "binds specifically" or similar terms, when used in the context of an antibody binding a target epitope, refers to the antibody having specificity for the target epitope (as opposed to other epitopes). The specificity need not be 100%. In one embodiment, the specificity is about 75% or greater (i.e., 75% specificity for the epitope). This means that about 75% of the antibodies that bind to an epitope will bind to the target epitope and about 25% of the antibodies will bind non-specifically. In another embodiment, the specificity is about 90% or greater.

In the above-defined method, determining if the capture ligands are respectively bound to an antigen can be carried out by using a detection ligand which is specific of said antigen but preferably binds to said antigen by recognition of an another binding site (i.e. epitope) than the recognition site of said capture ligand.

Preferably, the "detection ligand" according to the invention means marking or labeling molecules for detecting the ligand. The term 'marking' or "labeling" refers both to a direct labelling and to an indirect labelling (for example, by means of other ligands, themselves directly labelled, or using reagents of a labelled "affinity pair", such as, but not exclusively, the labelled avidin-biotin pair, etc.). Preferably, the label is a radioisotope, an enzyme or a fluorophore.

As will be clear to one of skill in the art, in the above-defined method, the protein of sequence SEQ ID NO: 2, SEQ ID NO: 4, SEQ ID NO: 6 or SEQ ID NO: 8, the homologous protein or the fragment can be used as a capture antigen.

Methods using capture antigens or ligands and detection ligands are well known to one of skill in the art and can be carried out in accordance with various well-known formats, for example in solid or homogeneous phase, in one or two steps, by a sandwich method or by a competitive method.

Preferably, the capture antigen or ligand is immobilised on a solid phase. By way of non-limiting examples of solid phase, microplates could be used, in particular polystyrene microplates, solid optionally paramagnetic particles or beads, or even polystyrene or polypropylene test tubes, glass, plastic or silicon chips, etc.

Although having distinct significances, the terms comprising, 'containing', and 'consisting of' were used in an interchangeable way in the description of the invention, and can be replaced one by the other.

The invention will be further described in view of the following examples.

Summary of the Sequences Described Herein:

| Sequence description | SEQ ID NO: |
|---|---|
| 26C4 nucleotide sequence | 1 |
| 26C4 protein sequence | 2 |

-continued

| Sequence description | SEQ ID NO: |
|---|---|
| 26F5 nucleotide sequence | 3 |
| 26F5protein sequence | 4 |
| 15C2 nucleotide sequence | 5 |
| 15C2 protein sequence | 6 |
| 26D6 nucleotide sequence | 7 |
| 26D6 protein sequence | 8 |
| 26E6 nucleotide sequence | 9 |
| 26E6 protein sequence | 10 |
| 26D4 nucleotide sequence | 11 |
| 26D4 protein sequence | 12 |
| 19F4 nucleotide sequence | 13 |
| 19F4 protein sequence | 14 |
| 18D4 nucleotide sequence | 15 |
| 18D4 protein sequence | 16 |
| 14C4 nucleotide sequence | 17 |
| 14C4 protein sequence | 18 |
| 17B6 nucleotide sequence | 19 |
| 17B6 protein sequence | 20 |
| 26C4 + His tag protein sequence | 21 |
| 26F5 + His tag protein sequence | 22 |
| 15C2 + His tag protein sequence | 23 |
| 26D6 + His tag protein sequence | 24 |
| 26E6 + His tag protein sequence | 25 |
| 26D4 + His tag protein sequence | 26 |
| 19F4 + His tag protein sequence | 27 |
| 18D4 + His tag protein sequence | 28 |
| 14C4 + His tag protein sequence | 29 |
| 17B6 + His tag protein sequence | 30 |
| 2B6 nucleotide sequence | 31 |
| 2B6 protein sequence | 32 |
| 7B3 nucleotide sequence | 33 |
| 7B3 protein sequence | 34 |
| 5G1 nucleotide sequence | 35 |
| 5G1 protein sequence | 36 |
| 2D6B1 nucleotide sequence | 37 |
| 2D6B1 protein sequence | 38 |
| 4A1 nucleotide sequence | 39 |
| 4A1 protein sequence | 40 |
| 9F2 nucleotide sequence | 41 |
| 9F2 protein sequence | 42 |
| 6H4 nucleotide sequence | 43 |
| 6H4 protein sequence | 44 |
| 25D6 nucleotide sequence | 45 |
| 25D6 protein sequence | 46 |
| 25D3 nucleotide sequence | 47 |
| 25D3 protein sequence | 48 |
| 25H3 nucleotide sequence | 49 |
| 25H3 protein sequence | 50 |
| 25C6 nucleotide sequence | 51 |
| 25C6 protein sequence | 52 |
| 14D3 nucleotide sequence | 53 |
| 14D3 protein sequence | 54 |
| 2E1 nucleotide sequence | 55 |
| 2E1 protein sequence | 56 |

EXAMPLES

Examples 1

Materials and Methods

Antigens 26C4 (SEQ ID NO: 21), 26F5 (SEQ ID NO: 22), 15C2 (SEQ ID NO: 23), 26D6 (SEQ ID NO: 24), 26E6 (SEQ ID NO: 25), 26D4 (SEQ ID NO: 26), 19F4 (SEQ ID NO: 27), 18D4 (SEQ ID NO: 28), 14C4 (SEQ ID NO: 29), and 17B6 (SEQ ID NO:30) were recombinantly produced in *Escherichia coli* and purified according to usual methods, such as described in Lavallie (1995) "Production of recombinant proteins in *Escherichia coli*". Unit 5.1. Current Protocols in Protein Science; Scopes (1995) "Strategies for protein purification" Unit 1.2. Current Protocols in Protein Science.

First screening was performed by high throughput ELISA. ELISA plates were coated overnight with 0.5 μg/mL of purified antigens (proteins 26C4, 26F5, 15C2, 26D4, 19F4). The plates were further saturated 2 hours with PBS-TWEEN® containing 4% serum albumin bovine (SAB). Hundred microliters of each serum sample of patients or controls were added at a 1/100 dilution for 30 minutes. Human peroxydase-labeled anti-IgG antibody was then added for 30 minutes before revelation with tetrabenzimidine (TMB) for approximately 15 minutes. Sulphuric acid (100 μL) were then added in each well to stop the reaction. The 450 nm absorbance of each well was then measured after 5 minutes. Are regarded as 'positive' in ELISA, the serums identified as containing antibodies recognizing specifically proteins (antigens) such as those defined according to the invention.

Pertinent antigens of the invention (proteins 26C4, 26F5, 15C2, 26D6) and previously described antigens (WO 2010/128232) 18D4, 14C4 and 17B6 were then tested with sensitive technology LUMINEX®. Briefly, the antigens were covalently attached to surface carboxyl groups of MAGPLEX® Microspheres (LUMINEX®) using N-hydroxysulfosuccinimide (sulfo-NHS) and 1-ethyl-3-(3-dimethylaminopropyl) carbodiimide hydrochloride (EDC) according the manufacturer's instructions. 50 μg were used for attachment to 5.000,000 microspheres. Detection of serum antibodies was carried out according to the manufacturer's instructions. Briefly, antigen-coupled microspheres were added to the wells of a multiwell plate and contacted with the various sera for a time sufficient to allow antibody-antigen complexes to be formed. After discarding the unreacted serum and washing the plate, a phycoerythrin-labeled anti-IgG antibody was added to the microspheres. Antibody-antigen complexes were further revealed by determining the mean fluorescence intensity (MFI) for each serum with a LUMINEX® analyzer.

The cut-off values for each serologic assay were determined by Receiver Operating Characteristics (ROC) curve analysis as described in the guideline GP10-A of December 1995 from the National Committee for Clinical Laboratory Standards (NCCLS) as the values yielding a maximum efficiency. The efficiency is defined as the ratio of the sum of the true positive samples and the true negative samples obtained with the serologic assays by the total number of samples assayed. True positive and negative samples are samples which are respectively determined as being positive and negative both using the serologic assay of the invention and bacteriological analysis. A sample was then considered positive if the antibody titer exceeded the defined cut-off value. The antigen combination was analyzed by discriminate function analysis before setting a cut-off value by ROC curve analysis as indicated above.

Example 2

Use of polypeptides of the invention for the detection of antibody in serum samples: first screening by high throughput ELISA.

The panel of samples tested is consisting of serum samples of 22 patients suffering from prosthetic joint infections on prosthesis wherein the infection with *P. acnes* was diagnosed positive with culture of 2 or more samplings on the infected prostheses. Control sera were collected from 96 healthy blood donors.

TABLE 1

| Results (ELISA) obtained by testing of the antigens | | | | | |
|---|---|---|---|---|---|
| | Tested antigens | | | | |
| Ratio of positive sera | 26C4 | 26F5 | 26E6 | 26D4 | 19F4 |
| *P. acnes* positive patients (22) | 94% | 83% | 89% | 89% | 6% |
| Healthy blood donors (96) | 6% | 4% | 34% | 33% | 14% |

Table 1 shows the results obtained according to the invention for polypeptides 26C4 (SEQ ID NO: 21), 26F5 (SEQ ID NO: 22), 26E6 (SEQ ID NO: 25), 26D4 (SEQ ID NO: 26), and 19F4 (SEQ ID NO: 27), with secondary antibodies recognizing the immunoglobulins G present in serum samples of patients or control healthy blood donors.

Results show that polypeptides of the invention 26C4 (SEQ ID NO: 21) and 26F5 (SEQ ID NO: 22) can be used for the diagnosis of infections of *P. acnes* on articular prostheses. Other polypeptides also tested, such as 26E6 (SEQ ID NO: 25), 26D4 (SEQ ID NO: 26) or 19F4 (SEQ ID NO: 27) do not allow the diagnosis of such infections with no sufficient sensitivity and/or specificity.

Example 3

Use of polypeptides of the invention for the diagnosis of *Propionibacterium* infections with panels of serums samples and control serum samples: second evaluation by LUMINEX® technology of the selected antigens.

The panel of samples tested is consisting of serum samples of 9 patients suffering from prosthetic joint infections wherein the infection with *P. acnes* was diagnosed positive with culture of 3 or more samplings on the infected prostheses and confirmed by Western blot analysis. Moreover, serums samples from 2 patients positive for a prosthesis infection to *P. granulosum* diagnosed positive with culture were tested. Control sera were collected from (i) 22 healthy prosthesis carriers with no clinical sign of infection since at least 2 years and (ii) 25 patients with prosthesis infections other than *Propionibacterium* infections; i.e. gram-positive coccus (n=1), *Corynebacterium* spp. (n=1), *Enterobacter aerogenes* (n=1), *Enterobacter amnigenus* (n=1), *Enterobacter cloacae* (n=3), *Pseudomonas aeruginosa* (n=2), *Streptococcus anginosus* (n=1), *Staphylococcus aureus* (n=9), *Staphylococcus capitis* (n=1), *Staphylococcus constellatus* (n=2), *Staphylococcus caprae* (n=1), *Streptococcus dysgalactiae* (n=1), *Staphylococcus epidermidis* (n=1).

TABLE 2

| Results (LUMINEX ® technology) obtained by testing of the selected antigens | | | |
|---|---|---|---|
| | Tested antigens | | |
| Ratio of positive sera | 26C4 | 26F5 | 15C2 |
| *P. acnes* positive patients (9) | 78% | 67% | 78% |
| *P. granulosum* positive patients (2) | 100% | 100% | 0% |
| Healthy prosthesis carriers (22) | 9% | 9% | 14% |
| Infected prosthesis patients with other infections than *Propionibacterium* spp. (25) | 16% | 8% | 8% |

The results show a significant antibody response (the probability associated with a test of $X^2$ is lower than 0.05) against the polypeptides identified according to the invention during the infections to *P. acnes* and, that 26C4 and 26F5 are also relevant for the serologic detection of other *Propionibacterium* species such as *P. granulosum* on infected articular prostheses.

Example 4

Diagnosis potency of the combination of 26C4, 26F5, 15C2 and 26D6 polypeptides of the invention for the diagnosis of Proprionibacterium *acnes* infections on prosthesis with panels of serums samples and control serum samples: third evaluation by LUMINEX@ technology. Comparison of antigenic polypeptides according to the invention with previously described antigenic polypeptides18D4, 14C4 and 17B6.

The panel of samples tested is consisting of serum samples of 31 patients suffering from prosthetic joint infections wherein the infection with *P. acnes* was diagnosed positive with culture of 3 or more samplings on the infected prostheses. Control sera were collected from (i) 36 healthy prosthesis carriers with no clinical sign of infection since at least 2 years, (ii) 47 patients with prosthesis infections other than *Propionibacterium* infections; i.e. *Enterobacter amnigenus* (n=1), *Enterobacter cloacae* (n=2), *Pseudomonas aeruginosa* (n=1), *Streptococcus anginosus* (n=1), *Staphylococcus aureus* (n=16), untyped coagulase negative *Staphylococcus* (n=1), *Staphylococcus caprae* (n=1), *Streptococcus dysgalactiae* (n=1), *Staphylococcus epidermidis* (n=15), *Staphylococcus lentus* (n=1) and (iii) 44 healthy blood donors.

| | Tested antigens | | | | | | | | | | |
|---|---|---|---|---|---|---|---|---|---|---|---|
| Ratio of positive sera | 26C4 | 26D6 | 26C4 | 26F5 | 26F5 | 14C4 | 17B6 | 26C4-26F5-15C2-26D6 | 18D4-15C2-26D6-26C4 | 14C4-15C2-26C4-26F5 | 17B6-15C2-26D6-26F5 |
| *P. acnes* positive patients (31) | 55% | 77% | 35% | 71% | 64% | 45% | 52% | 81% | 52% | 45% | 45% |
| Healthy prosthesis carriers (36) | 25% | 33% | 31% | 44% | 47% | 47% | 53% | 28% | 33% | 17% | 25% |
| Healthy blood donors (39) | 36% | 27% | 30% | 2% | 14% | 61% | 27% | 14% | 14% | 30% | 5% |
| Infected prosthesis patients with other infections than *Propionibacterium* genus (47) | 28% | 32% | 17% | 26% | 49% | 43% | 55% | 13% | 23% | 15% | 13% |
| Total of control sera (127) | 30% | 31% | 25% | 23% | 36% | 50% | 45% | 17% | 23% | 20% | 13% |

The results show a significant antibody response (the probability associated with a test of $X^2$ is lower than 0.05) against the polypeptides during the *P. acnes* prosthetic joint infections. The results clearly show that the use of one polypeptide according to the invention (26C4 or 26F5, or 15C2, or 26D6) provides a better specificity for detecting patients suffering from *P Acnes* prosthetic joint infections than other polypeptides (18D4, 14C4 or 17B6). Moreover, the use of two or three peptides according to the invention improves the specificity of detection comparing with 18D4, 14C4 or 17B6 peptides. Best result is provided by the use of the fourth peptides 26C4 26F5, 15C2 and 26D6 according to the invention. Indeed, the 26C4-26F5-15C2-26D6 combination is shown to be of the very best interest since it allows a 6%-13% of increase in specificity and a 4%-46% increase in sensitivity in comparison with antigens alone.

In conclusion, it appears impossible to predict the sensitivity and specificity, in particular an increase of the specificity and of the sensitivity, of a combination of antigens in view of their individual sensitivities and specificities. Besides, each of 26C4 26F5 15C2 26D6 has good detecting abilities and the 26C4-26F5-15C2-26D6 combination presents unexpected diagnosis potency for the diagnosis of *P. acnes* prosthetic joint infections.

What is claimed is:

1. An in vitro method of determining if an individual having an implanted prosthesis is infected by *Propionibacterium*, the method comprising:

contacting, separately, a biological sample of the individual and one or more corresponding control sample(s) with at least one purified or synthetic protein of SEQ ID NO: 2, SEQ ID NO: 4, SEQ ID NO: 6, and SEQ ID NO: 8, wherein the biological sample is selected from the group consisting of blood, serum, plasma, saliva, urine, pleural liquid, cephalorachidian fluid, articular liquid, and mucosa-associated lymphoid tissue, determining, separately, an amount of antibodies bound specifically to said at least one protein present in the biological sample and in the one or more control (s) samples, comparing the amount of the bound antibodies in the biological sample to the amount of the bound antibodies in the one or more control sample(s), and determining whether or not the individual is infected by said *Propionibacterium* based upon said comparison.

2. The method of claim 1, wherein said *Propionibacterium* is selected from the group consisting of *P. acnes, P. avidum, P. granulosum*, and *P. propionicum.*

3. The method of claim 1, wherein the antibodies are IgG.

4. The method of claim 1, wherein the implanted prosthesis is selected form the group consisting of neurosurgical devices, intracardiac devices, ear implants, nose implants, breast implants, throat implants, urological implants, endotracheal tubes, tracheostomy tubes, dialysis catheters, CNS shunts, ocular implants, orthopedic implants, and prosthetic joints.

5. The method of claim 4, wherein the implanted prosthesis is a prosthetic joint selected from the group consisting of a knee joint, a shoulder joint, and a hip joint.

6. The method of claim 1, wherein the wherein the individual is under antibiotic treatment.

7. An in vitro method of determining if an individual having an implanted prosthesis is infected by *Propionibacterium*, the method comprising:

(a) contacting, separately, a capture ligand specific to the protein of at least one of SEQ ID NO: 2, SEQ ID NO: 4, SEQ ID NO: 6, and SEQ ID NO: 8 with a biological sample of the individual, and with one or more corresponding control sample(s), wherein the biological sample is selected from the group consisting of blood, serum, plasma, saliva, urine, cephalorachidian fluid, pleural liquid, articular liquid, and mucosa-associated lymphoid tissue;

(b) determining if said protein is bound specifically to the specific capture ligand and (c) deducing therefrom whether the individual is infected by the *Propionibacterium.*

8. The method of claim 7, wherein said method further comprises:

determining, separately, an amount of the capture ligand bound specifically to said protein in the biological sample and in the one or more control sample(s), comparing the amount of the bound capture ligand in the biological sample to the amount of the bound capture ligand in the one or more control sample(s), and determining whether or not the individual is infected by said *Propionibacterium* based upon said comparison.

* * * * *